United States Patent
Butler et al.

(10) Patent No.: US 7,312,375 B2
(45) Date of Patent: Dec. 25, 2007

(54) PLANT REPRODUCTION POLYNUCLEOTIDES AND METHODS OF USE

(75) Inventors: Karlene H. Butler, Newark, DE (US); Olga Danilevskaya, Johnston, IA (US); Guo-Hua Miao, Johnston, IA (US); Michele Morgante, Udine (IT); Hajime Sakai, Newark, DE (US); Carl R. Simmons, Des Moines, IA (US); Zude Weng, Vernon Hills, IL (US); Omolayo O. Famodu, Newark, DE (US); Sabine Hantke, Koein (DE)

(73) Assignee: Pioneer Hi-Bred International, Inc., Johnston, IA (US)

( * ) Notice: Subject to any disclaimer, the term of this patent is extended or adjusted under 35 U.S.C. 154(b) by 193 days.

(21) Appl. No.: 10/967,851

(22) Filed: Oct. 18, 2004

(65) Prior Publication Data

US 2005/0216974 A1   Sep. 29, 2005

Related U.S. Application Data

(60) Division of application No. 09/967,552, filed on Sep. 28, 2001, now Pat. No. 6,887,988, which is a continuation-in-part of application No. PCT/US00/23735, filed on Aug. 30, 2000.

(60) Provisional application No. 60/151,575, filed on Aug. 31, 1999.

(51) Int. Cl.
*C12N 15/29* (2006.01)
*C12N 15/82* (2006.01)
*C12N 5/04* (2006.01)
*A01H 5/00* (2006.01)
*A01H 5/10* (2006.01)

(52) U.S. Cl. ................ 800/278; 536/24.1; 435/320.1; 435/419; 800/320; 800/320.1; 800/298; 800/281

(58) Field of Classification Search ............... 536/24.1; 435/320.1, 419; 800/298, 287, 278, 320.1
See application file for complete search history.

(56) References Cited

U.S. PATENT DOCUMENTS

| 6,229,064 B1 | 5/2001 | Fischer et al. | |
|---|---|---|---|
| 6,239,327 B1 | 5/2001 | Grossniklaus et al. | |
| 6,486,302 B1 * | 11/2002 | Briggs et al. | ............ 530/376 |

FOREIGN PATENT DOCUMENTS

| WO | WO 01/16325 | 3/2001 |
|---|---|---|
| WO | WO 01/64891 | 9/2001 |

OTHER PUBLICATIONS

Benfey et al (1990, Science 250:959-966).*
Benfey et al (1989, EMBO J, 8(8):2195-2202.*
Busch et al (1999, Science 285:585-587).*
Lohmann et al (2001, Cell 105 :793-803).*
Fourgoux-Nicol et al (1999, Plant Molecular Biology 40 :857-872).*
Chaudhury, et al.: "Fertilization-independent seed development in *Arabidopsis thaliana*"; *Proc. Natl. Acad. Sci. USA*; Apr. 1997; vol. 94, pp. 4223-4228.
Grossniklaus, et al.: "Material control of embryogenesis by MEDEA, a polycomb group gene in *Arabidopsis*"; *Science*; Apr. 17, 1998; vol. 280, pp. 446-450.
Luo, et al.; "Expression and parent-of-origin effects for FIS2, MEA and FIE in the endosperm and embryo of developing *Arabidopsis* seeds"; *Proc. Natl. Acad. Sci. USA*; Sep. 12, 1990; vol. 19; pp. 10637-10642.
Ohad, et al.; "A mutation that allows endosperm development without fertilization"; *Proc. Natl. Acad. Sci. USA*; May 1996; vol. 93, pp. 5319-5324.
Ohad, et al.; "Mutations in FIE, a WD polycomb group gene, allow endosperm development without fertilization", *The Plant Cell*; Mar. 1999; vol. 11, pp. 407-416.
Pirrotta, V.; "Polycombing the genome: PoG IxG, and Chromatin silencing", *Cell*; May 1, 1998; vol. 93, pp. 333-336.
Vielle-Calzada, et al.; "Maintenance of genomic Imprinting at the *Arabidopsis medea* locus requires zygotic DDM1 activity"; *Genes & Development*; 1999 by Cold Spring Harbor Laboratory Press; pp. 2971-2982.
Accession No. AF129516; "*Arabidopsis thaliana* fertilization-independent endosperm protein (FIE) mRNA complete cos"; Apr. 6, 1999.
Accession No. AAD23584; "Fertilization-independent endosperm protein [*Arabidopsis thaliana*]"; Mar. 26, 1999.
Accession No. D85597; "Oryzta australiensis retrotransposon RIRE1 complete sequence"; Sep. 27, 1997.
Walbot, V.; "605065H09. x1 605 Endosperm cDNA library from Schmidt lab Zea mays cDNA, mRNA sequence"; EMBL Sequence Database; Jun. 9, 1999, XP002158115 Heidelberg DE.
Saski, T.; "Rice cDNA, partial sequence"; EMBL Sequence Database; Aug. 6, 1997; XP002158156; Heidelberg DE.
Blewitt, et al.; "BNLGH6867 Six-day cotton fiber *Gossyplum hirsutum* cDNA 5' similar to (AF003604) extra sex combs (Schistocerca Americana), mRNA sequence"; EMBL Sequence Database: Jun. 12, 1999; XP002168157; Heidelberg DE.
Cordonnier-Pratt, et al.; "DG1_87 G07.b1_A002 Dark grown 1 (DG1) Sorgum bicolor cDNA, mRNA sequence"; EMBL Sequence Database; Jul. 28, 2000; XP002156158; Heidelberg DE.

* cited by examiner

*Primary Examiner*—Stuart F. Baum

(57) ABSTRACT

This invention relates to an isolated nucleic acid fragment encoding a reproduction protein. The invention also relates to the construction of a chimeric gene encoding all or a portion of the reproduction protein, in sense or antisense orientation, wherein expression of the chimeric gene results in production of altered levels of the reproduction protein in a transformed host cell. The invention also provides isolated transcriptional regulatory elements and polynucleotides associated therewith.

14 Claims, 1 Drawing Sheet

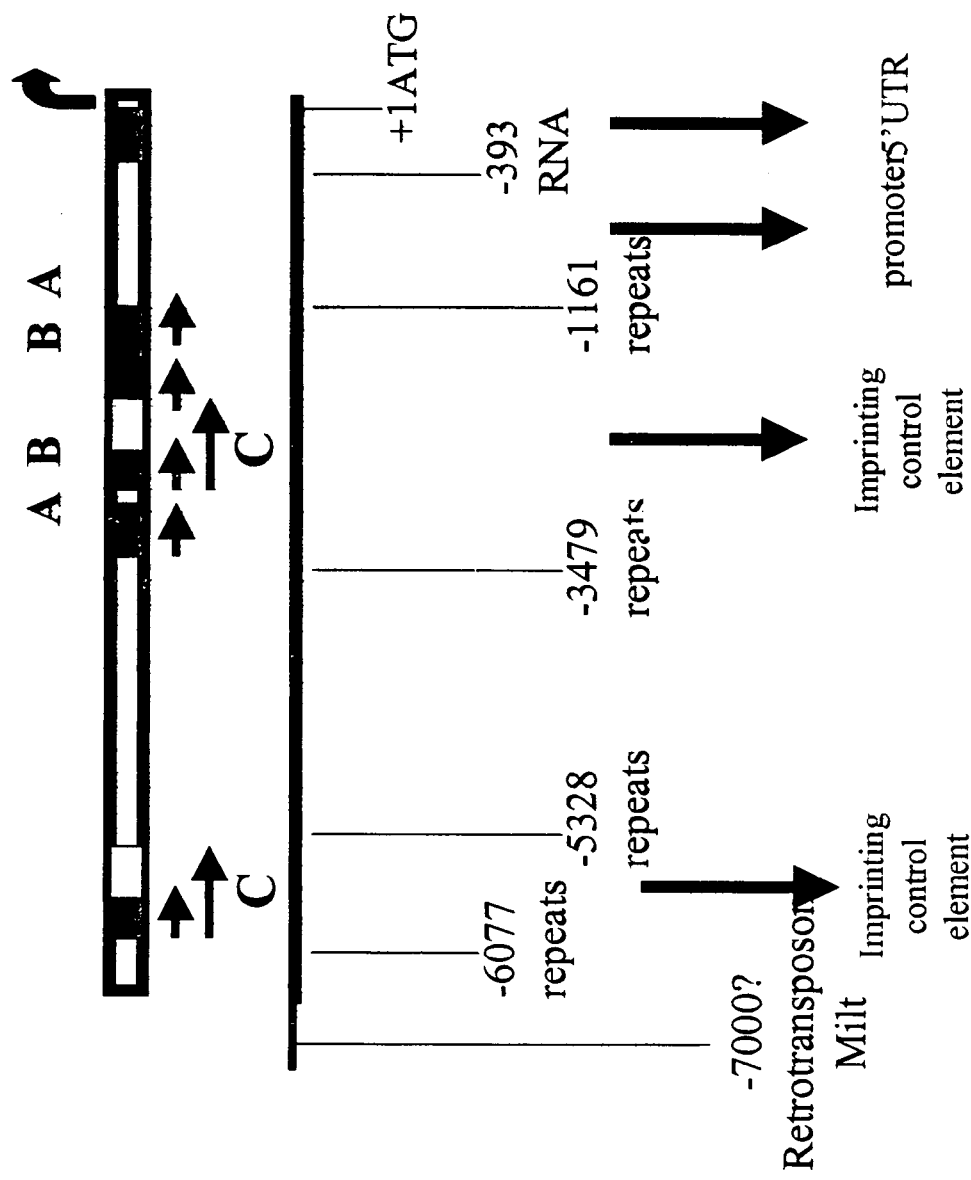
Figure 1. Pattern of direct repeats in ZmFIE-B 5' upstream region

SEQUENCE LISTING

<160> NUMBER OF SEQ ID NOS: 82

<210> SEQ ID NO 1
<211> LENGTH: 1643
<212> TYPE: DNA
<213> ORGANISM: Zea mays
<220> FEATURE:
<221> NAME/KEY: CDS
<222> LOCATION: (193)...(1332)

<400> SEQUENCE: 1

```
gcacgaggcc ggaagaagtc gccgcgtgag gtcagtgtcc ccgttgctgc cgcctctaac      60
ccgaagccta ggccgctgcc ggtgcataac aaggagaatc aggcggaggg gaaagtagca     120
gaggaggggg cagcaactga ggaggggag aagtaccggg cggaaccgga aatcttgccg      180
ctgccgccgg cc atg gcg aag ctg ggc ccg ggg cag ggg ctc ggg tgc gag    231
              Met Ala Lys Leu Gly Pro Gly Gln Gly Leu Gly Cys Glu
                1               5                   10 gcg gcg gag ggg tcg ctc gtg ccc agc cgg aag cgg gag tac aag ccc       279
Ala Ala Glu Gly Ser Leu Val Pro Ser Arg Lys Arg Glu Tyr Lys Pro
     15                  20                  25 tgc ggc aag cac act gag ggg aag cgc ccg cta tat gct atc ggg ttc       327
Cys Gly Lys His Thr Glu Gly Lys Arg Pro Leu Tyr Ala Ile Gly Phe
 30                  35                  40                  45 aac ttc atg gac gcg cgc tac tac gac gtc ttc gcc acc gtc ggc ggc       375
Asn Phe Met Asp Ala Arg Tyr Tyr Asp Val Phe Ala Thr Val Gly Gly
                 50                  55                  60 aac cgc gtg aca act tac cgc tgc ctt gag aat ggt agt ttc gct ctt       423
```

```
                                                                                    -continued Asn Arg Val Thr Thr Tyr Arg Cys Leu Glu Asn Gly Ser Phe Ala Leu
            65                  70                  75 cta caa gct tac gtt gat gag gat aag gat gag tcg ttc tat act cta        471
Leu Gln Ala Tyr Val Asp Glu Asp Lys Asp Glu Ser Phe Tyr Thr Leu
        80                  85                  90 agc tgg gct cgt gac cat gtt gat ggc tca cca ctg ctg gtg gca gca        519
Ser Trp Ala Arg Asp His Val Asp Gly Ser Pro Leu Leu Val Ala Ala
    95                  100                 105 gga agc aat ggg atc att cgg gtc atc aat tgt gct aca gaa aag tta        567
Gly Ser Asn Gly Ile Ile Arg Val Ile Asn Cys Ala Thr Glu Lys Leu
110                 115                 120                 125 gct aag agc ttt gtt ggc cat ggc gac tca ata aat gag ata aga act        615
Ala Lys Ser Phe Val Gly His Gly Asp Ser Ile Asn Glu Ile Arg Thr
                130                 135                 140 caa ccg ttg aag cct tcg ctc atc att tct gca agc aag gat gaa tct        663
Gln Pro Leu Lys Pro Ser Leu Ile Ile Ser Ala Ser Lys Asp Glu Ser
            145                 150                 155 gtt agg cta tgg aat gtc cat aca ggg atc tgt atc ttg ata ttt gct        711
Val Arg Leu Trp Asn Val His Thr Gly Ile Cys Ile Leu Ile Phe Ala
        160                 165                 170 gga gct gga ggt cat cgc aat gaa gta ttg agt gtt gac ttc cat cct        759
Gly Ala Gly Gly His Arg Asn Glu Val Leu Ser Val Asp Phe His Pro
    175                 180                 185 agt gat att gaa cgt ttt gca agt tgt ggc atg gac aac act gtg aaa        807
Ser Asp Ile Glu Arg Phe Ala Ser Cys Gly Met Asp Asn Thr Val Lys
190                 195                 200                 205 atc tgg tca atg aaa gaa ttt tgg cta tat gtt gac aaa tca tat tca        855
Ile Trp Ser Met Lys Glu Phe Trp Leu Tyr Val Asp Lys Ser Tyr Ser
                210                 215                 220 tgg act gac ctt cca tca aag ttt cca aca aaa tat gtc cag ttt cca        903
Trp Thr Asp Leu Pro Ser Lys Phe Pro Thr Lys Tyr Val Gln Phe Pro
            225                 230                 235 gtc ttg att gct gca gta cac tct aac tat gtt gat tgt aca aga tgg        951
Val Leu Ile Ala Ala Val His Ser Asn Tyr Val Asp Cys Thr Arg Trp
        240                 245                 250 ctt ggt gac ttc atc cta tca aag agt gtt gac aat gaa att gtg ctt        999
Leu Gly Asp Phe Ile Leu Ser Lys Ser Val Asp Asn Glu Ile Val Leu
    255                 260                 265 tgg gaa ccg aag aca aaa gaa cag agt cct ggg gag gga agc atc gat        1047
Trp Glu Pro Lys Thr Lys Glu Gln Ser Pro Gly Glu Gly Ser Ile Asp
270                 275                 280                 285 atc ctt cag aag tat cct gtc cca gaa tgt gac att tgg ttt atc aaa        1095
Ile Leu Gln Lys Tyr Pro Val Pro Glu Cys Asp Ile Trp Phe Ile Lys
                290                 295                 300 ttt tca tgt gat ttt cac ttc aat cag ttg gcg ata ggc aac cgt gaa        1143
Phe Ser Cys Asp Phe His Phe Asn Gln Leu Ala Ile Gly Asn Arg Glu
            305                 310                 315 ggc aaa atc tac gtg tgg gaa gta cag tcc agc cct cct gtc ctc att        1191
Gly Lys Ile Tyr Val Trp Glu Val Gln Ser Ser Pro Pro Val Leu Ile
        320                 325                 330 gct cgg ctg tat aat cag cag tgt aaa tcg ccg ata aga caa act gca        1239
Ala Arg Leu Tyr Asn Gln Gln Cys Lys Ser Pro Ile Arg Gln Thr Ala
    335                 340                 345 gtg tcc ttc gat gga agc aca atc ctt gga gct ggt gaa gac ggc acc        1287
Val Ser Phe Asp Gly Ser Thr Ile Leu Gly Ala Gly Glu Asp Gly Thr
350                 355                 360                 365 atc tgg cgg tgg gat gaa gtg gac cat ccg agc tcc aga aac tga            1332
Ile Trp Arg Trp Asp Glu Val Asp His Pro Ser Ser Arg Asn *
                370                 375
```

```
agaagtgttg ccgctcaatg ctggactgat ggttacgctc ggttgggggtt gcgatggttg   1392 aatccgttgg tggaaagtgc cacctggtgt tttttctagt caaaatggtt ggtgttaaca   1452
gaatattgaa tgcttcgaat gttgaaagtt gggatgcttg tgctggtact ctgctccgtg   1512
gacgagtgaa cttaggtgcc gtttggttca catatttgta acgtaatggg taacagataa   1572
cgttaaatca tgtttgtttt atttcaaccg taatcagata ccacattaaa attaaaaaaa   1632
aaaaaaaaaa a                                                        1643
```

<210> SEQ ID NO 2
<211> LENGTH: 379
<212> TYPE: PRT
<213> ORGANISM: Zea mays

<400> SEQUENCE: 2

```
Met Ala Lys Leu Gly Pro Gly Gln Gly Leu Gly Cys Glu Ala Ala Glu
 1               5                  10                  15

Gly Ser Leu Val Pro Ser Arg Lys Arg Glu Tyr Lys Pro Cys Gly Lys
            20                  25                  30

His Thr Glu Gly Lys Arg Pro Leu Tyr Ala Ile Gly Phe Asn Phe Met
        35                  40                  45

Asp Ala Arg Tyr Tyr Asp Val Phe Ala Thr Val Gly Gly Asn Arg Val
    50                  55                  60

Thr Thr Tyr Arg Cys Leu Glu Asn Gly Ser Phe Ala Leu Leu Gln Ala
65                  70                  75                  80

Tyr Val Asp Glu Asp Lys Asp Glu Ser Phe Tyr Thr Leu Ser Trp Ala
                85                  90                  95

Arg Asp His Val Asp Gly Ser Pro Leu Leu Val Ala Ala Gly Ser Asn
            100                 105                 110

Gly Ile Ile Arg Val Ile Asn Cys Ala Thr Glu Lys Leu Ala Lys Ser
        115                 120                 125

Phe Val Gly His Gly Asp Ser Ile Asn Glu Ile Arg Thr Gln Pro Leu
    130                 135                 140

Lys Pro Ser Leu Ile Ile Ser Ala Ser Lys Asp Glu Ser Val Arg Leu
145                 150                 155                 160

Trp Asn Val His Thr Gly Ile Cys Ile Leu Ile Phe Ala Gly Ala Gly
                165                 170                 175

Gly His Arg Asn Glu Val Leu Ser Val Asp Phe His Pro Ser Asp Ile
            180                 185                 190

Glu Arg Phe Ala Ser Cys Gly Met Asp Asn Thr Val Lys Ile Trp Ser
        195                 200                 205

Met Lys Glu Phe Trp Leu Tyr Val Asp Lys Ser Tyr Ser Trp Thr Asp
    210                 215                 220

Leu Pro Ser Lys Phe Pro Thr Lys Tyr Val Gln Phe Pro Val Leu Ile
225                 230                 235                 240

Ala Ala Val His Ser Asn Tyr Val Asp Cys Thr Arg Trp Leu Gly Asp
                245                 250                 255

Phe Ile Leu Ser Lys Ser Val Asp Asn Glu Ile Val Leu Trp Glu Pro
            260                 265                 270

Lys Thr Lys Glu Gln Ser Pro Gly Glu Gly Ser Ile Asp Ile Leu Gln
        275                 280                 285

Lys Tyr Pro Val Pro Glu Cys Asp Ile Trp Phe Ile Lys Phe Ser Cys
    290                 295                 300

Asp Phe His Phe Asn Gln Leu Ala Ile Gly Asn Arg Glu Gly Lys Ile
305                 310                 315                 320
```

```
Tyr Val Trp Glu Val Gln Ser Ser Pro Val Leu Ile Ala Arg Leu
                325                 330                 335

Tyr Asn Gln Gln Cys Lys Ser Pro Ile Arg Gln Thr Ala Val Ser Phe
            340                 345                 350

Asp Gly Ser Thr Ile Leu Gly Ala Gly Glu Asp Gly Thr Ile Trp Arg
        355                 360                 365

Trp Asp Glu Val Asp His Pro Ser Ser Arg Asn
    370                 375

<210> SEQ ID NO 3
<211> LENGTH: 1794
<212> TYPE: DNA
<213> ORGANISM: Zea mays
<220> FEATURE:
<221> NAME/KEY: CDS
<222> LOCATION: (176)...(1561)

<400> SEQUENCE: 3
```

| | | |
|---|---|---|
| gttaaacaca aaatgtgcat cgccgccgcc accatataga accacttatc atgaaccgcc | 60 |
| gccatcacat ccactgcctc aactagtgtt accacctatg ttcattgtt gtgtctgctt | 120 |
| cttgtagcac tgttggtcta caaacattca tatttctctc aacatctggc acagc atg<br>                                                                                                                                                                Met<br>                                                                                                                                                                1 | 178 |
| ccg cct tcc aaa gca cgc cga aag agg tca ctt cgt gat atc act gcc<br>Pro Pro Ser Lys Ala Arg Arg Lys Arg Ser Leu Arg Asp Ile Thr Ala<br>              5                      10                      15 | 226 |
| acc gtt gcc act ggg act gtt gcc aac tcg aaa cct ggc tca tca tcg<br>Thr Val Ala Thr Gly Thr Val Ala Asn Ser Lys Pro Gly Ser Ser Ser<br>        20                      25                      30 | 274 |
| acg aac gag ggg aag caa cag gac aag aaa aag gag ggt cca cag gaa<br>Thr Asn Glu Gly Lys Gln Gln Asp Lys Lys Lys Glu Gly Pro Gln Glu<br> 35                      40                      45 | 322 |
| ccg gac atc cca cca tta ccg ccg gtg gtg gtg aat ata gtc cca cga<br>Pro Asp Ile Pro Pro Leu Pro Pro Val Val Val Asn Ile Val Pro Arg<br>50                      55                      60                      65 | 370 |
| caa gga tta gga tgt gaa gta gtg gaa ggg cta ctc gtg cct agt cgg<br>Gln Gly Leu Gly Cys Glu Val Val Glu Gly Leu Leu Val Pro Ser Arg<br>              70                      75                      80 | 418 |
| aag cga gag tac aag ccc aat agc aag tat act gtg gga aat cac ccg<br>Lys Arg Glu Tyr Lys Pro Asn Ser Lys Tyr Thr Val Gly Asn His Pro<br>        85                      90                      95 | 466 |
| atc tat gcc atc ggg ttc aat ttc att gac atg cgc tac tat gat gtc<br>Ile Tyr Ala Ile Gly Phe Asn Phe Ile Asp Met Arg Tyr Tyr Asp Val<br>           100                      105                    110 | 514 |
| ttt gcc atc gcc agt tgc aat agt gtg ata att tac cga tgc ctt gag<br>Phe Ala Ile Ala Ser Cys Asn Ser Val Ile Ile Tyr Arg Cys Leu Glu<br>115                      120                      125 | 562 |
| aat ggt ggt ttt ggt ctt cta caa aat tat gtt gat gag gat aag gat<br>Asn Gly Gly Phe Gly Leu Leu Gln Asn Tyr Val Asp Glu Asp Lys Asp<br>130                      135                      140                      145 | 610 |
| gag tca ttc tac act cta agc tgg acc atc gat caa gtt gat agc tca<br>Glu Ser Phe Tyr Thr Leu Ser Trp Thr Ile Asp Gln Val Asp Ser Ser<br>                150                      155                      160 | 658 |
| ccg ctg ttg gtg gcc gca gga agc aat cgg atc att cgg gtc atc aat<br>Pro Leu Leu Val Ala Ala Gly Ser Asn Arg Ile Ile Arg Val Ile Asn<br>           165                      170                    175 | 706 |
| tgt gct acc gaa aag tta gat aag agc tta gtt ggc cat ggt ggt tca<br>Cys Ala Thr Glu Lys Leu Asp Lys Ser Leu Val Gly His Gly Gly Ser<br>180                      185                      190 | 754 |

```
ata cat gag ata agg act cat gcc tcg aag cca tca ctc atc att tct      802
Ile His Glu Ile Arg Thr His Ala Ser Lys Pro Ser Leu Ile Ile Ser
    195                 200                 205 gcc agc aag gat gaa tct att agg cta tgg aat gtc cat act ggg att      850
Ala Ser Lys Asp Glu Ser Ile Arg Leu Trp Asn Val His Thr Gly Ile
210                 215                 220                 225 tgc atc tta gtc ttt gca ggg gct gga ggc cat cga cat gat gtg ttg      898
Cys Ile Leu Val Phe Ala Gly Ala Gly Gly His Arg His Asp Val Leu
                230                 235                 240 agt gtt gac ttc cac cct acc gag gtt ggg att ttt gca agt tgt ggc      946
Ser Val Asp Phe His Pro Thr Glu Val Gly Ile Phe Ala Ser Cys Gly
            245                 250                 255 atg gac aat act gtg aaa att tgg tca atg aaa gaa ttt tgg ata tat      994
Met Asp Asn Thr Val Lys Ile Trp Ser Met Lys Glu Phe Trp Ile Tyr
        260                 265                 270 gtt gaa aaa tca tat tca tgg act ggc cat cca tca aag ttt cca acg     1042
Val Glu Lys Ser Tyr Ser Trp Thr Gly His Pro Ser Lys Phe Pro Thr
    275                 280                 285 agg aat atc cag ttt ccg gtc ttg act gct gca gta cac tct gac tat     1090
Arg Asn Ile Gln Phe Pro Val Leu Thr Ala Ala Val His Ser Asp Tyr
290                 295                 300                 305 gtt gat tgt aca aga tgg ctt ggt gac ttc atc cta tca aag agt gta     1138
Val Asp Cys Thr Arg Trp Leu Gly Asp Phe Ile Leu Ser Lys Ser Val
                310                 315                 320 aag aat gca gtt ttg ctt tgg gaa cca aaa cca gac aag cgt agg cct     1186
Lys Asn Ala Val Leu Leu Trp Glu Pro Lys Pro Asp Lys Arg Arg Pro
            325                 330                 335 ggg gag ggg agt gtt gat gtt ctt cag aag tac ccg gtg cca aag tgt     1234
Gly Glu Gly Ser Val Asp Val Leu Gln Lys Tyr Pro Val Pro Lys Cys
        340                 345                 350 tca tta tgg ttt atg aaa ttt tca tgt gat ttt tac tcc aac cag atg     1282
Ser Leu Trp Phe Met Lys Phe Ser Cys Asp Phe Tyr Ser Asn Gln Met
    355                 360                 365 gca ata ggc aac aat aaa ggc gag atc tat gtc tgg gaa gtg cag tcc     1330
Ala Ile Gly Asn Asn Lys Gly Glu Ile Tyr Val Trp Glu Val Gln Ser
370                 375                 380                 385 agc ccg ccc gtc tta att gac cgg ctg tgc aac cag gaa tgc aag tcg     1378
Ser Pro Pro Val Leu Ile Asp Arg Leu Cys Asn Gln Glu Cys Lys Ser
                390                 395                 400 ccg ata agg cag acc gca gtg tca ttc gac gga agc acg atc ctt gga     1426
Pro Ile Arg Gln Thr Ala Val Ser Phe Asp Gly Ser Thr Ile Leu Gly
            405                 410                 415 gcc gcc gac gac ggc gcg atc tgg cgg tgg gac gaa gtg gac cct gct     1474
Ala Ala Asp Asp Gly Ala Ile Trp Arg Trp Asp Glu Val Asp Pro Ala
        420                 425                 430 gct tcc agc tcc aaa cct gat caa gct gct gcg ccc gcc gcc ggt gtc     1522
Ala Ser Ser Ser Lys Pro Asp Gln Ala Ala Ala Pro Ala Ala Gly Val
    435                 440                 445 ggt gcc ggt gcc ggt gcc gac gcc gac gcc gac gcc tga gcgagaggac      1571
Gly Ala Gly Ala Gly Ala Asp Ala Asp Ala Asp Ala  *
450                 455                 460 cgtcgccgcc cgccggttca catcgatcgt actccgtgct ggttgattag ctttacccat   1631
tggtatgttt tggttcagag tcgccagatc tagtgtgtgg ctgaacgttg aatgttagga   1691
tgctgctgtt tgttatgctc tgagtcttga gttcactttg ttaatttgca ccgtggatga   1751
gatgaataac ttgacgttgc aaaaaaaaaa aaaaaaaraa aaa                     1794

<210> SEQ ID NO 4
```

```
<211> LENGTH: 461
<212> TYPE: PRT
<213> ORGANISM: Zea mays

<400> SEQUENCE: 4

Met Pro Pro Ser Lys Ala Arg Arg Lys Arg Ser Leu Arg Asp Ile Thr
 1               5                  10                  15

Ala Thr Val Ala Thr Gly Thr Val Ala Asn Ser Lys Pro Gly Ser Ser
            20                  25                  30

Ser Thr Asn Glu Gly Lys Gln Gln Asp Lys Lys Glu Gly Pro Gln
        35                  40                  45

Glu Pro Asp Ile Pro Pro Leu Pro Val Val Asn Ile Val Pro
    50                  55                  60

Arg Gln Gly Leu Gly Cys Glu Val Val Glu Gly Leu Leu Val Pro Ser
65                  70                  75                  80

Arg Lys Arg Glu Tyr Lys Pro Asn Ser Lys Tyr Thr Val Gly Asn His
                85                  90                  95

Pro Ile Tyr Ala Ile Gly Phe Asn Phe Ile Asp Met Arg Tyr Tyr Asp
            100                 105                 110

Val Phe Ala Ile Ala Ser Cys Asn Ser Val Ile Ile Tyr Arg Cys Leu
            115                 120                 125

Glu Asn Gly Gly Phe Gly Leu Leu Gln Asn Tyr Val Asp Glu Asp Lys
        130                 135                 140

Asp Glu Ser Phe Tyr Thr Leu Ser Trp Thr Ile Asp Gln Val Asp Ser
145                 150                 155                 160

Ser Pro Leu Leu Val Ala Ala Gly Ser Asn Arg Ile Ile Arg Val Ile
                165                 170                 175

Asn Cys Ala Thr Glu Lys Leu Asp Lys Ser Leu Val Gly His Gly Gly
            180                 185                 190

Ser Ile His Glu Ile Arg Thr His Ala Ser Lys Pro Ser Leu Ile Ile
        195                 200                 205

Ser Ala Ser Lys Asp Glu Ser Ile Arg Leu Trp Asn Val His Thr Gly
    210                 215                 220

Ile Cys Ile Leu Val Phe Ala Gly Ala Gly His Arg His Asp Val
225                 230                 235                 240

Leu Ser Val Asp Phe His Pro Thr Glu Val Gly Ile Phe Ala Ser Cys
                245                 250                 255

Gly Met Asp Asn Thr Val Lys Ile Trp Ser Met Lys Glu Phe Trp Ile
            260                 265                 270

Tyr Val Glu Lys Ser Tyr Ser Trp Thr Gly His Pro Ser Lys Phe Pro
        275                 280                 285

Thr Arg Asn Ile Gln Phe Pro Val Leu Thr Ala Val His Ser Asp
    290                 295                 300

Tyr Val Asp Cys Thr Arg Trp Leu Gly Asp Phe Ile Leu Ser Lys Ser
305                 310                 315                 320

Val Lys Asn Ala Val Leu Leu Trp Glu Pro Lys Pro Asp Lys Arg Arg
                325                 330                 335

Pro Gly Glu Gly Ser Val Asp Val Leu Gln Lys Tyr Pro Val Pro Lys
            340                 345                 350

Cys Ser Leu Trp Phe Met Lys Phe Ser Cys Asp Phe Tyr Ser Asn Gln
        355                 360                 365

Met Ala Ile Gly Asn Asn Lys Gly Glu Ile Tyr Val Trp Glu Val Gln
    370                 375                 380

Ser Ser Pro Pro Val Leu Ile Asp Arg Leu Cys Asn Gln Glu Cys Lys
```

-continued

```
             385                 390                 395                 400
Ser Pro Ile Arg Gln Thr Ala Val Ser Phe Asp Gly Ser Thr Ile Leu
                405                 410                 415
Gly Ala Asp Asp Gly Ala Ile Trp Arg Trp Asp Glu Val Asp Pro
        420                 425                 430
Ala Ala Ser Ser Lys Pro Asp Gln Ala Ala Pro Ala Ala Gly
            435                 440                 445
Val Gly Ala Gly Ala Asp Ala Asp Ala
        450                 455             460

<210> SEQ ID NO 5
<211> LENGTH: 1749
<212> TYPE: DNA
<213> ORGANISM: Zea mays
<220> FEATURE:
<221> NAME/KEY: CDS
<222> LOCATION: (131)...(1516)

<400> SEQUENCE: 5
gcacgaggaa ccgccgccat cacatccact gcctcaacta gtgttaccac ctatggttca      60
ttgttgtgtc tgcttcttgt agcactgttg gtctacaaac attcatattt ctctcaacat     120
ctggcacagc atg ccg cct tcc aaa gca cgc cga aag agg tca ctt cgt       169
           Met Pro Pro Ser Lys Ala Arg Arg Lys Arg Ser Leu Arg
             1               5                  10 gat atc act gcc acc gtt gcc act ggg act gtt gcc aac tcg aaa cct      217
Asp Ile Thr Ala Thr Val Ala Thr Gly Thr Val Ala Asn Ser Lys Pro
 15                  20                  25 ggc tca tca tcg acg aac gag ggg aag caa cag gac aag aaa aag gag      265
Gly Ser Ser Ser Thr Asn Glu Gly Lys Gln Gln Asp Lys Lys Lys Glu
 30                  35                  40                  45 ggt cca cag gaa ccg gac atc cca cca tta ccg ccg gtg gtg gtg aat      313
Gly Pro Gln Glu Pro Asp Ile Pro Pro Leu Pro Pro Val Val Val Asn
                50                  55                  60 ata gtc cca cga caa gga tta gga tgt gaa gta gtg gaa ggg cta ctc      361
Ile Val Pro Arg Gln Gly Leu Gly Cys Glu Val Val Glu Gly Leu Leu
     65                  70                  75 gtg cct agt cgg aag cga gag tac aag ccc aat agc aag tat act gtg      409
Val Pro Ser Arg Lys Arg Glu Tyr Lys Pro Asn Ser Lys Tyr Thr Val
         80                  85                  90 gga aat cac ccg atc tat gcc atc ggg ttc aat ttc att gac atg cgc      457
Gly Asn His Pro Ile Tyr Ala Ile Gly Phe Asn Phe Ile Asp Met Arg
             95                 100                 105 tac tat gat gtc ttt gcc atc gcc agt tgc aat agt gtg ata att tac      505
Tyr Tyr Asp Val Phe Ala Ile Ala Ser Cys Asn Ser Val Ile Ile Tyr
110                 115                 120                 125 cga tgc ctt gag aat ggt ggt ttt ggt ctt cta caa aat tat gtt gat      553
Arg Cys Leu Glu Asn Gly Gly Phe Gly Leu Leu Gln Asn Tyr Val Asp
                130                 135                 140 gag gat aag gat gag tca ttc tac act cta agc tgg acc atc gat caa      601
Glu Asp Lys Asp Glu Ser Phe Tyr Thr Leu Ser Trp Thr Ile Asp Gln
            145                 150                 155 gtt gat agc tca ccg ctg ttg gtg gcc gca gga agc aat cgg atc att      649
Val Asp Ser Ser Pro Leu Leu Val Ala Ala Gly Ser Asn Arg Ile Ile
        160                 165                 170 cgg gtc atc aat tgt gct acc gaa aag tta gat aag agc tta gtt ggc      697
Arg Val Ile Asn Cys Ala Thr Glu Lys Leu Asp Lys Ser Leu Val Gly
    175                 180                 185 cat ggt ggt tca ata cat gag ata agg act cat gcc tcg aag cca tca      745
His Gly Gly Ser Ile His Glu Ile Arg Thr His Ala Ser Lys Pro Ser
```

```
                190                  195                   200                   205
ctc atc att tct gcc agc aag gat gaa tct att agg cta tgg aat gtc    793
Leu Ile Ile Ser Ala Ser Lys Asp Glu Ser Ile Arg Leu Trp Asn Val
                210                   215                   220 cat act ggg att tgc atc tta gtc ttt gca ggg gct gga ggc cat cga    841
His Thr Gly Ile Cys Ile Leu Val Phe Ala Gly Ala Gly Gly His Arg
            225                   230                   235 cat gat gtg ttg agt gtt gac ttc cac cct acc gag gtt ggg att ttt    889
His Asp Val Leu Ser Val Asp Phe His Pro Thr Glu Val Gly Ile Phe
        240                   245                   250 gca agt tgt ggc atg gac aat act gtg aaa att tgg tca atg aaa gaa    937
Ala Ser Cys Gly Met Asp Asn Thr Val Lys Ile Trp Ser Met Lys Glu
    255                   260                   265 ttt tgg ata tat gtt gaa aaa tca tat tca tgg act ggc cat cca tca    985
Phe Trp Ile Tyr Val Glu Lys Ser Tyr Ser Trp Thr Gly His Pro Ser
270                   275                   280                   285 aag ttt cca acg agg aat atc cag ttt ccg gtc ttg act gct gca gta    1033
Lys Phe Pro Thr Arg Asn Ile Gln Phe Pro Val Leu Thr Ala Ala Val
                290                   295                   300 cac tct gac tat gtt gat tgt aca aga tgg ctt ggt gac ttc atc cta    1081
His Ser Asp Tyr Val Asp Cys Thr Arg Trp Leu Gly Asp Phe Ile Leu
            305                   310                   315 tca aag agt gta aag aat gca gtt ttg ctt tgg gaa cca aaa cca gac    1129
Ser Lys Ser Val Lys Asn Ala Val Leu Leu Trp Glu Pro Lys Pro Asp
        320                   325                   330 aag cgt agg cct ggg gag ggg agt gtt gat gtt ctt cag aag tac ccg    1177
Lys Arg Arg Pro Gly Glu Gly Ser Val Asp Val Leu Gln Lys Tyr Pro
    335                   340                   345 gtg cca aag tgt tca tta tgg ttt atg aaa ttt tca tgt gat ttt tac    1225
Val Pro Lys Cys Ser Leu Trp Phe Met Lys Phe Ser Cys Asp Phe Tyr
350                   355                   360                   365 tcc aac cag atg gca ata ggc aac aat aaa ggc gag atc tat gtc tgg    1273
Ser Asn Gln Met Ala Ile Gly Asn Asn Lys Gly Glu Ile Tyr Val Trp
                370                   375                   380 gaa gtg cag tcc agc ccg ccc gtc tta att gac cgg ctg tgc aac cag    1321
Glu Val Gln Ser Ser Pro Pro Val Leu Ile Asp Arg Leu Cys Asn Gln
            385                   390                   395 gaa tgc aag tcg ccg ata agg cag acc gca gtg tca ttc gac gga agc    1369
Glu Cys Lys Ser Pro Ile Arg Gln Thr Ala Val Ser Phe Asp Gly Ser
        400                   405                   410 acg atc ctt gga gcc gcc gac gac ggc gcg atc tgg cgg tgg gac gaa    1417
Thr Ile Leu Gly Ala Ala Asp Asp Gly Ala Ile Trp Arg Trp Asp Glu
    415                   420                   425 gtg gac cct gct gct tcc agc tcc aaa cct gat caa gct gct gcg ccc    1465
Val Asp Pro Ala Ala Ser Ser Ser Lys Pro Asp Gln Ala Ala Ala Pro
430                   435                   440                   445 gcc gcc ggt gtc ggt gcc ggt gcc ggt gcc gac gcc gac gcc gac gcc    1513
Ala Ala Gly Val Gly Ala Gly Ala Gly Ala Asp Ala Asp Ala Asp Ala
                450                   455                   460 tga gcgagaggac cgtcgccgcc cgccggttca catcgatcgt actccgtgct        1566
 * ggttgattag ctttacccat tggtatgttt tggttcagag tcgccagatc tagtgtgtgg   1626
ctgaacgttg aatgttagga tgctgctgtt tgttatgctc tgagtcttga gttcactttg   1686
ttaatttgca ccgtggatga gatgaataac ttgacgttgc aaaaaaaaaa aaaaaaaaa    1746 aaa                                                                 1749

<210> SEQ ID NO 6
```

<211> LENGTH: 461
<212> TYPE: PRT
<213> ORGANISM: Zea mays

<400> SEQUENCE: 6

```
Met Pro Pro Ser Lys Ala Arg Arg Lys Arg Ser Leu Arg Asp Ile Thr
 1               5                  10                  15

Ala Thr Val Ala Thr Gly Thr Val Ala Asn Ser Lys Pro Gly Ser Ser
            20                  25                  30

Ser Thr Asn Glu Gly Lys Gln Gln Asp Lys Lys Glu Gly Pro Gln
        35                  40                  45

Glu Pro Asp Ile Pro Pro Leu Pro Val Val Asn Ile Val Pro
    50                  55                  60

Arg Gln Gly Leu Gly Cys Glu Val Val Glu Gly Leu Leu Val Pro Ser
 65              70                  75                  80

Arg Lys Arg Glu Tyr Lys Pro Asn Ser Lys Tyr Thr Val Gly Asn His
                85                  90                  95

Pro Ile Tyr Ala Ile Gly Phe Asn Phe Ile Asp Met Arg Tyr Tyr Asp
            100                 105                 110

Val Phe Ala Ile Ala Ser Cys Asn Ser Val Ile Ile Tyr Arg Cys Leu
            115                 120                 125

Glu Asn Gly Gly Phe Gly Leu Leu Gln Asn Tyr Val Asp Glu Asp Lys
130                 135                 140

Asp Glu Ser Phe Tyr Thr Leu Ser Trp Thr Ile Asp Gln Val Asp Ser
145                 150                 155                 160

Ser Pro Leu Leu Val Ala Ala Gly Ser Asn Arg Ile Ile Arg Val Ile
                165                 170                 175

Asn Cys Ala Thr Glu Lys Leu Asp Lys Ser Leu Val Gly His Gly Gly
            180                 185                 190

Ser Ile His Glu Ile Arg Thr His Ala Ser Lys Pro Ser Leu Ile Ile
        195                 200                 205

Ser Ala Ser Lys Asp Glu Ser Ile Arg Leu Trp Asn Val His Thr Gly
    210                 215                 220

Ile Cys Ile Leu Val Phe Ala Gly Ala Gly His Arg His Asp Val
225                 230                 235                 240

Leu Ser Val Asp Phe His Pro Thr Glu Val Gly Ile Phe Ala Ser Cys
                245                 250                 255

Gly Met Asp Asn Thr Val Lys Ile Trp Ser Met Lys Glu Phe Trp Ile
            260                 265                 270

Tyr Val Glu Lys Ser Tyr Ser Trp Thr Gly His Pro Ser Lys Phe Pro
        275                 280                 285

Thr Arg Asn Ile Gln Phe Pro Val Leu Thr Ala Ala Val His Ser Asp
    290                 295                 300

Tyr Val Asp Cys Thr Arg Trp Leu Gly Asp Phe Ile Leu Ser Lys Ser
305                 310                 315                 320

Val Lys Asn Ala Val Leu Leu Trp Glu Pro Lys Pro Asp Lys Arg Arg
                325                 330                 335

Pro Gly Glu Gly Ser Val Asp Val Leu Gln Lys Tyr Pro Val Pro Lys
            340                 345                 350

Cys Ser Leu Trp Phe Met Lys Phe Ser Cys Asp Phe Tyr Ser Asn Gln
        355                 360                 365

Met Ala Ile Gly Asn Asn Lys Gly Glu Ile Tyr Val Trp Glu Val Gln
    370                 375                 380

Ser Ser Pro Pro Val Leu Ile Asp Arg Leu Cys Asn Gln Glu Cys Lys
```

```
                385              390              395              400
           Ser Pro Ile Arg Gln Thr Ala Val Ser Phe Asp Gly Ser Thr Ile Leu
                        405              410              415

Gly Ala Ala Asp Asp Gly Ala Ile Trp Arg Trp Asp Glu Val Asp Pro
                        420              425              430

Ala Ala Ser Ser Ser Lys Pro Asp Gln Ala Ala Pro Ala Ala Gly
                        435              440              445

Val Gly Ala Gly Ala Gly Asp Ala Asp Ala Asp Ala
                        450              455              460

<210> SEQ ID NO 7
<211> LENGTH: 743
<212> TYPE: DNA
<213> ORGANISM: Zea mays
<220> FEATURE:
<221> NAME/KEY: CDS
<222> LOCATION: (1)...(459)

<400> SEQUENCE: 7 aag ttt cca aca aaa tat gtc cag ttt cca gtc ttg att gct gca gta      48
Lys Phe Pro Thr Lys Tyr Val Gln Phe Pro Val Leu Ile Ala Ala Val
  1               5                  10                  15 cac tct aac tat gtt gat tgt aca aga tgg ctt ggt gac ttc atc cta      96
His Ser Asn Tyr Val Asp Cys Thr Arg Trp Leu Gly Asp Phe Ile Leu
              20                  25                  30 tca aag agt gtt gac aat gaa att gtg ctt tgg gaa ccg aag aca aaa     144
Ser Lys Ser Val Asp Asn Glu Ile Val Leu Trp Glu Pro Lys Thr Lys
         35                  40                  45 gaa cag agt cct ggg gag gga agc atc gat atc ctt cag aag tat cct     192
Glu Gln Ser Pro Gly Glu Gly Ser Ile Asp Ile Leu Gln Lys Tyr Pro
     50                  55                  60 gtc cca gaa tgt gac att tgg ttt atc aaa ttt tca tgt gat ttt cac     240
Val Pro Glu Cys Asp Ile Trp Phe Ile Lys Phe Ser Cys Asp Phe His
 65                  70                  75                  80 ttc aat cag ttg gcg ata ggc aac cgt gaa ggc aaa atc tac gtg tgg     288
Phe Asn Gln Leu Ala Ile Gly Asn Arg Glu Gly Lys Ile Tyr Val Trp
                 85                  90                  95 gaa gta cag tcc agc cct cct gtc ctc att gct cgg ctg tat aat cag     336
Glu Val Gln Ser Ser Pro Pro Val Leu Ile Ala Arg Leu Tyr Asn Gln
            100                 105                 110 cag tgt aaa tcg ccg ata aga caa act gca gtg tcc ttc gat gga agc     384
Gln Cys Lys Ser Pro Ile Arg Gln Thr Ala Val Ser Phe Asp Gly Ser
        115                 120                 125 aca atc ctt gga gct ggt gaa gac ggc acc atc tgg cgg tgg gat gaa     432
Thr Ile Leu Gly Ala Gly Glu Asp Gly Thr Ile Trp Arg Trp Asp Glu
    130                 135                 140 gtg gac cat ccg agc tcc aga agc tga agaagtgttg ccgctcaatg           479
Val Asp His Pro Ser Ser Arg Ser *
145                 150 ctggactgat ggttacgctc ggttggggtt gtgatggttg aatccgttgg cggaaagtgc   539
cacctggtgt tttttctagt caaaatggtt ggtgttaaca gaatattgaa tgcttcgaat   599
gttgaaagtt gggatgcttg tgctggtact ctgctccgcg gacgagtgaa cttagtttgt   659
tgcaactttg ggaaccgttg tcatctgttt gttctgcatt tctaaaaaga gagcaaattt   719
caggataaaa aaaaaaaaaa aaaa                                          743

<210> SEQ ID NO 8
<211> LENGTH: 152
<212> TYPE: PRT
```

<213> ORGANISM: Zea mays

<400> SEQUENCE: 8

```
Lys Phe Pro Thr Lys Tyr Val Gln Phe Pro Val Leu Ile Ala Ala Val
1               5                   10                  15

His Ser Asn Tyr Val Asp Cys Thr Arg Trp Leu Gly Asp Phe Ile Leu
            20                  25                  30

Ser Lys Ser Val Asp Asn Glu Ile Val Leu Trp Glu Pro Lys Thr Lys
        35                  40                  45

Glu Gln Ser Pro Gly Glu Gly Ser Ile Asp Ile Leu Gln Lys Tyr Pro
    50                  55                  60

Val Pro Glu Cys Asp Ile Trp Phe Ile Lys Phe Ser Cys Asp Phe His
65              70                  75                  80

Phe Asn Gln Leu Ala Ile Gly Asn Arg Glu Gly Lys Ile Tyr Val Trp
                85                  90                  95

Glu Val Gln Ser Ser Pro Pro Val Leu Ile Ala Arg Leu Tyr Asn Gln
            100                 105                 110

Gln Cys Lys Ser Pro Ile Arg Gln Thr Ala Val Ser Phe Asp Gly Ser
        115                 120                 125

Thr Ile Leu Gly Ala Gly Glu Asp Gly Thr Ile Trp Arg Trp Asp Glu
    130                 135                 140

Val Asp His Pro Ser Ser Arg Ser
145                 150
```

<210> SEQ ID NO 9
<211> LENGTH: 1626
<212> TYPE: DNA
<213> ORGANISM: Eucalyptus grandis
<220> FEATURE:
<221> NAME/KEY: CDS
<222> LOCATION: (123)...(1241)

<400> SEQUENCE: 9

```
gcaccagctc gttcgccgtt cggcgtcttc accggcggcg cgcgccgcac tgcgtaccca      60
ccggctgtcg cgttctcgcg gatcgaactc gaggaaaagg catcggcggc ggatcggggc     120 aa atg gcg aag atc gcg ccc ggg tgc gaa ccg gtg gcg ggg acg ctg       167
   Met Ala Lys Ile Ala Pro Gly Cys Glu Pro Val Ala Gly Thr Leu
   1               5                   10                  15 acc ccg tcg aag aag agg gag tac agg gtc acc aac agg ctc cag gag     215
Thr Pro Ser Lys Lys Arg Glu Tyr Arg Val Thr Asn Arg Leu Gln Glu
            20                  25                  30 ggg aag cgt ccc ctc tat gcc gtc gtc ttc aac ttc atc gac tcc cgc     263
Gly Lys Arg Pro Leu Tyr Ala Val Val Phe Asn Phe Ile Asp Ser Arg
        35                  40                  45 tac ttc aac gta ttc gcc acc gtc ggc ggc aac cgg gtt act gtt tat     311
Tyr Phe Asn Val Phe Ala Thr Val Gly Gly Asn Arg Val Thr Val Tyr
    50                  55                  60 cag tgt ctc gaa ggg gga gta ata gct gtg ttg cag tca tac att gat     359
Gln Cys Leu Glu Gly Gly Val Ile Ala Val Leu Gln Ser Tyr Ile Asp
65              70                  75 gaa gat aag gac gag tcg ttt tac acg gtc agc tgg gcg tgc aac att     407
Glu Asp Lys Asp Glu Ser Phe Tyr Thr Val Ser Trp Ala Cys Asn Ile
80              85                  90                  95 gat aga acc cca ttt gtg gtg gcg gga gga atc aat ggt atc atc cgt     455
Asp Arg Thr Pro Phe Val Val Ala Gly Gly Ile Asn Gly Ile Ile Arg
                100                 105                 110 gta att gat gct ggc aat gag aag ata cac agg agt ttt gta ggc cat     503
Val Ile Asp Ala Gly Asn Glu Lys Ile His Arg Ser Phe Val Gly His
```

```
                    115                 120                 125
ggg gat tca ata aat gaa atc agg act caa cca ttg aac cca tcc ctc      551
Gly Asp Ser Ile Asn Glu Ile Arg Thr Gln Pro Leu Asn Pro Ser Leu
        130                 135                 140 atc gtg tct gct agc aaa gat gaa tcc gtt agg ctc tgg aac gtt cat      599
Ile Val Ser Ala Ser Lys Asp Glu Ser Val Arg Leu Trp Asn Val His
    145                 150                 155 acg gga att tgt atc ctg ata ttt gct gga gct ggg ggt cat cgc aat      647
Thr Gly Ile Cys Ile Leu Ile Phe Ala Gly Ala Gly Gly His Arg Asn
160                 165                 170                 175 gaa gtt ttg agt gtg gac ttc cat cct tcc gac aag tac cgt att gca      695
Glu Val Leu Ser Val Asp Phe His Pro Ser Asp Lys Tyr Arg Ile Ala
                180                 185                 190 agt tgt ggt atg gac aat acg gtt aaa atc tgg tca atg aaa gag ttc      743
Ser Cys Gly Met Asp Asn Thr Val Lys Ile Trp Ser Met Lys Glu Phe
            195                 200                 205 tgg aca tat gtg gag aag tca ttt aca tgg aca gat ctt cca tcg aag      791
Trp Thr Tyr Val Glu Lys Ser Phe Thr Trp Thr Asp Leu Pro Ser Lys
        210                 215                 220 ttt ccc acc aaa tac gtg cag ttt cca gtt ttc ata gct cca gtt cat      839
Phe Pro Thr Lys Tyr Val Gln Phe Pro Val Phe Ile Ala Pro Val His
    225                 230                 235 tca aac tat gtt gac tgc aac agg tgg ctt ggt gat ttt gtt ctg tca      887
Ser Asn Tyr Val Asp Cys Asn Arg Trp Leu Gly Asp Phe Val Leu Ser
240                 245                 250                 255 aag agt gtt gac aac gag att gtg ctt tgg gaa ccc aaa atg aag gaa      935
Lys Ser Val Asp Asn Glu Ile Val Leu Trp Glu Pro Lys Met Lys Glu
                260                 265                 270 caa tct ccg gga gag gga tcg gtg gat atc ctt cag aaa tat cca gtt      983
Gln Ser Pro Gly Glu Gly Ser Val Asp Ile Leu Gln Lys Tyr Pro Val
            275                 280                 285 cca gag tgt gac att tgg ttc atc aaa ttt tcc tgt gac ttt cat tat     1031
Pro Glu Cys Asp Ile Trp Phe Ile Lys Phe Ser Cys Asp Phe His Tyr
        290                 295                 300 cac tca att gct ata gga aat agg gaa ggg aag atc tac gta tgg gag     1079
His Ser Ile Ala Ile Gly Asn Arg Glu Gly Lys Ile Tyr Val Trp Glu
    305                 310                 315 ctg cag agt agc cct cct gtt cta att gca aag ttg tct cat tcc caa     1127
Leu Gln Ser Ser Pro Pro Val Leu Ile Ala Lys Leu Ser His Ser Gln
320                 325                 330                 335 tca aaa tcc cca atc aga cag acc gcc atg tca ttt gat ggg agc aca     1175
Ser Lys Ser Pro Ile Arg Gln Thr Ala Met Ser Phe Asp Gly Ser Thr
                340                 345                 350 atc ctg agc tgc tgt gag gat ggt act ata tgg cgc tgg gat gca att     1223
Ile Leu Ser Cys Cys Glu Asp Gly Thr Ile Trp Arg Trp Asp Ala Ile
            355                 360                 365 acg gca tca aca tcc taa gccttccatg gcagatggac tggagaactc            1271
Thr Ala Ser Thr Ser  *
        370 cgtttgtaat taggaatccc tcttgtgtgg gcatgttccc caccatgtat cagctaaatg   1331 ggagctgctt caacctctta tctcgatgga gactcgaata gcatcaccgc acaggtgcaa   1391 gcggacaact gcttttggt aacgaagaaa gcaagtggat gatttggttg tgcatcagtc    1451 tgaacgattt atgaagttac tttttggtgt caaatgtact ctccgtgaat catttcactt   1511 cgcaaactgg gatttgtacc ttagaaacat ccatttttaat ctaccttaac ttcccagaaa  1571 aaaaaaaaaa aaaaaaaaaa aaaaaaaaaa aaaaaaaaaa aaaaa                  1626
```

<210> SEQ ID NO 10
<211> LENGTH: 372
<212> TYPE: PRT
<213> ORGANISM: Eucalyptus grandis

<400> SEQUENCE: 10

Met Ala Lys Ile Ala Pro Gly Cys Glu Pro Val Ala Gly Thr Leu Thr
1               5                   10                  15

Pro Ser Lys Lys Arg Glu Tyr Arg Val Thr Asn Arg Leu Gln Glu Gly
            20                  25                  30

Lys Arg Pro Leu Tyr Ala Val Val Phe Asn Phe Ile Asp Ser Arg Tyr
        35                  40                  45

Phe Asn Val Phe Ala Thr Val Gly Gly Asn Arg Val Thr Val Tyr Gln
    50                  55                  60

Cys Leu Glu Gly Gly Val Ile Ala Val Leu Gln Ser Tyr Ile Asp Glu
65                  70                  75                  80

Asp Lys Asp Glu Ser Phe Tyr Thr Val Ser Trp Ala Cys Asn Ile Asp
                85                  90                  95

Arg Thr Pro Phe Val Val Ala Gly Ile Asn Gly Ile Ile Arg Val
            100                 105                 110

Ile Asp Ala Gly Asn Glu Lys Ile His Arg Ser Phe Val Gly His Gly
        115                 120                 125

Asp Ser Ile Asn Glu Ile Arg Thr Gln Pro Leu Asn Pro Ser Leu Ile
    130                 135                 140

Val Ser Ala Ser Lys Asp Glu Ser Val Arg Leu Trp Asn Val His Thr
145                 150                 155                 160

Gly Ile Cys Ile Leu Ile Phe Ala Gly Ala Gly His Arg Asn Glu
                165                 170                 175

Val Leu Ser Val Asp Phe His Pro Ser Asp Lys Tyr Arg Ile Ala Ser
            180                 185                 190

Cys Gly Met Asp Asn Thr Val Lys Ile Trp Ser Met Lys Glu Phe Trp
        195                 200                 205

Thr Tyr Val Glu Lys Ser Phe Thr Trp Thr Asp Leu Pro Ser Lys Phe
    210                 215                 220

Pro Thr Lys Tyr Val Gln Phe Pro Val Phe Ile Ala Pro Val His Ser
225                 230                 235                 240

Asn Tyr Val Asp Cys Asn Arg Trp Leu Gly Asp Phe Val Leu Ser Lys
                245                 250                 255

Ser Val Asp Asn Glu Ile Val Leu Trp Glu Pro Lys Met Lys Glu Gln
            260                 265                 270

Ser Pro Gly Glu Gly Ser Val Asp Ile Leu Gln Lys Tyr Pro Val Pro
        275                 280                 285

Glu Cys Asp Ile Trp Phe Ile Lys Phe Ser Cys Asp Phe His Tyr His
    290                 295                 300

Ser Ile Ala Ile Gly Asn Arg Glu Gly Lys Ile Tyr Val Trp Glu Leu
305                 310                 315                 320

Gln Ser Ser Pro Pro Val Leu Ile Ala Lys Leu Ser His Ser Gln Ser
                325                 330                 335

Lys Ser Pro Ile Arg Gln Thr Ala Met Ser Phe Asp Gly Ser Thr Ile
            340                 345                 350

Leu Ser Cys Cys Glu Asp Gly Thr Ile Trp Arg Trp Asp Ala Ile Thr
        355                 360                 365

Ala Ser Thr Ser
    370

```
<210> SEQ ID NO 11
<211> LENGTH: 619
<212> TYPE: DNA
<213> ORGANISM: Helianthus sp.
<220> FEATURE:
<221> NAME/KEY: CDS
<222> LOCATION: (3)...(380)

<400> SEQUENCE: 11 cc acg cgt ccg ctt ggt gat ttc ata cta tct aag agt gta gac aat        47
   Thr Arg Pro Leu Gly Asp Phe Ile Leu Ser Lys Ser Val Asp Asn
     1               5                  10                  15 gag ttc ata ttg tgg gag ccg aag atg aaa gag cag tct cca gga gag       95
Glu Phe Ile Leu Trp Glu Pro Lys Met Lys Glu Gln Ser Pro Gly Glu
             20                  25                  30 ggc acg gtg gat att ctt cag aaa tat cct gta cct gat tgt gac atc      143
Gly Thr Val Asp Ile Leu Gln Lys Tyr Pro Val Pro Asp Cys Asp Ile
 35                  40                  45 tgg ttt ata aag ctt tcc tgt gat ttc cat tac aat gca gca gct att      191
Trp Phe Ile Lys Leu Ser Cys Asp Phe His Tyr Asn Ala Ala Ala Ile
     50                  55                  60 ggt aac aga gaa gga aaa atc tat gta tgg gaa ttg cag act agc ccg      239
Gly Asn Arg Glu Gly Lys Ile Tyr Val Trp Glu Leu Gln Thr Ser Pro
 65                  70                  75 cct tct ctt att gca agg tta tct cat att cag tcc aaa tcg cca atc      287
Pro Ser Leu Ile Ala Arg Leu Ser His Ile Gln Ser Lys Ser Pro Ile
 80                  85                  90                  95 agg caa act gct atg tca ttt gat gga agc aca att ctg agt tgc tgt      335
Arg Gln Thr Ala Met Ser Phe Asp Gly Ser Thr Ile Leu Ser Cys Cys
                 100                 105                 110 gaa gat ggc acc atc tgg cgt tgg gat act gtt gca acg tcg tag          380
Glu Asp Gly Thr Ile Trp Arg Trp Asp Thr Val Ala Thr Ser   *
             115                 120                 125 cttgtgttgg tttgaaacaa gtcatgttgt gtaccatgta tattccttca gcaatttcgt    440
ttgttttccg tggtgatgat gaggcatttt aatttgttct ttattaaact atgatagtag    500
gatgtattcg tttagtgact ggccaacttg atatatgttt gtcggtgtta agcttttaaa    560
aaaaaaaaaa aaaaaaaaaa aaaaaaaaaa aaaaaaaaaa aaaaaaaaaa aaaaaaaaa     619

<210> SEQ ID NO 12
<211> LENGTH: 125
<212> TYPE: PRT
<213> ORGANISM: Helianthus sp.

<400> SEQUENCE: 12

Thr Arg Pro Leu Gly Asp Phe Ile Leu Ser Lys Ser Val Asp Asn Glu
  1               5                  10                  15
Phe Ile Leu Trp Glu Pro Lys Met Lys Glu Gln Ser Pro Gly Glu Gly
             20                  25                  30
Thr Val Asp Ile Leu Gln Lys Tyr Pro Val Pro Asp Cys Asp Ile Trp
         35                  40                  45
Phe Ile Lys Leu Ser Cys Asp Phe His Tyr Asn Ala Ala Ala Ile Gly
     50                  55                  60
Asn Arg Glu Gly Lys Ile Tyr Val Trp Glu Leu Gln Thr Ser Pro Pro
 65                  70                  75                  80
Ser Leu Ile Ala Arg Leu Ser His Ile Gln Ser Lys Ser Pro Ile Arg
                 85                  90                  95
Gln Thr Ala Met Ser Phe Asp Gly Ser Thr Ile Leu Ser Cys Cys Glu
             100                 105                 110
Asp Gly Thr Ile Trp Arg Trp Asp Thr Val Ala Thr Ser
         115                 120                 125

<210> SEQ ID NO 13
<211> LENGTH: 1428
```

-continued

```
<212> TYPE: DNA
<213> ORGANISM: Catalpa speciosa
<220> FEATURE:
<221> NAME/KEY: CDS
<222> LOCATION: (42)...(1154)

<400> SEQUENCE: 13
```

| | | | | | | | | | | | | | | | | |
|---|---|---|---|---|---|---|---|---|---|---|---|---|---|---|---|---|
| gcacgagggc | atacaggcgg | tgctaatctg | caggtaagga | g | atg | gca | aaa | att | ccg | | | | | | | 56 |
| | | | | | Met | Ala | Lys | Ile | Pro | | | | | | | |
| | | | | | 1 | | | | 5 | | | | | | | |

| ttg | ggt | tgt | gag | ccc | atg | gtg | ggt | tcc | tta | acg | ccg | tcg | aag | aaa | cgg | 104 |
|---|---|---|---|---|---|---|---|---|---|---|---|---|---|---|---|---|
| Leu | Gly | Cys | Glu | Pro | Met | Val | Gly | Ser | Leu | Thr | Pro | Ser | Lys | Lys | Arg | |
| | | | 10 | | | | | 15 | | | | | 20 | | | |

| gag | tat | agg | gtc | acc | aac | agg | ctc | cag | gaa | ggc | aaa | cgc | ccc | att | tac | 152 |
|---|---|---|---|---|---|---|---|---|---|---|---|---|---|---|---|---|
| Glu | Tyr | Arg | Val | Thr | Asn | Arg | Leu | Gln | Glu | Gly | Lys | Arg | Pro | Ile | Tyr | |
| | | 25 | | | | | 30 | | | | | 35 | | | | |

| gcc | gtc | gtt | ttc | aac | ttc | att | gac | tcc | cgt | tac | ttc | aac | gct | ttc | gcc | 200 |
|---|---|---|---|---|---|---|---|---|---|---|---|---|---|---|---|---|
| Ala | Val | Val | Phe | Asn | Phe | Ile | Asp | Ser | Arg | Tyr | Phe | Asn | Ala | Phe | Ala | |
| | | 40 | | | | | 45 | | | | | 50 | | | | |

| act | gcc | ggt | ggc | aat | cgc | gtg | act | gta | tac | cag | tgc | cta | gaa | ggt | ggt | 248 |
|---|---|---|---|---|---|---|---|---|---|---|---|---|---|---|---|---|
| Thr | Ala | Gly | Gly | Asn | Arg | Val | Thr | Val | Tyr | Gln | Cys | Leu | Glu | Gly | Gly | |
| | 55 | | | | | 60 | | | | | 65 | | | | | |

| gtt | ata | gct | gta | cta | cag | tcc | tac | att | gat | gaa | gat | aaa | gat | gaa | tct | 296 |
|---|---|---|---|---|---|---|---|---|---|---|---|---|---|---|---|---|
| Val | Ile | Ala | Val | Leu | Gln | Ser | Tyr | Ile | Asp | Glu | Asp | Lys | Asp | Glu | Ser | |
| 70 | | | | | 75 | | | | | 80 | | | | | 85 | |

| ttc | tac | act | gta | agt | tgg | gct | tgc | aat | att | gat | gga | act | cca | ttc | ttg | 344 |
|---|---|---|---|---|---|---|---|---|---|---|---|---|---|---|---|---|
| Phe | Tyr | Thr | Val | Ser | Trp | Ala | Cys | Asn | Ile | Asp | Gly | Thr | Pro | Phe | Leu | |
| | | | | 90 | | | | | 95 | | | | | 100 | | |

| gtg | gct | gga | gga | ctt | aat | gga | att | att | cga | gtt | att | gat | act | ggc | aat | 392 |
|---|---|---|---|---|---|---|---|---|---|---|---|---|---|---|---|---|
| Val | Ala | Gly | Gly | Leu | Asn | Gly | Ile | Ile | Arg | Val | Ile | Asp | Thr | Gly | Asn | |
| | | | 105 | | | | | 110 | | | | | 115 | | | |

| gag | aag | ata | tac | aag | agt | ttt | gtg | ggt | cat | ggg | gat | tca | ata | aac | gaa | 440 |
|---|---|---|---|---|---|---|---|---|---|---|---|---|---|---|---|---|
| Glu | Lys | Ile | Tyr | Lys | Ser | Phe | Val | Gly | His | Gly | Asp | Ser | Ile | Asn | Glu | |
| | | 120 | | | | | 125 | | | | | 130 | | | | |

| att | cga | act | cag | ccg | ctg | aaa | cca | tca | ctt | gtt | gtg | tca | gca | agc | aaa | 488 |
|---|---|---|---|---|---|---|---|---|---|---|---|---|---|---|---|---|
| Ile | Arg | Thr | Gln | Pro | Leu | Lys | Pro | Ser | Leu | Val | Val | Ser | Ala | Ser | Lys | |
| | 135 | | | | | 140 | | | | | 145 | | | | | |

| gat | gaa | tct | gta | cgc | ctg | tgg | aat | att | cat | act | ggg | ata | tgc | att | ttg | 536 |
|---|---|---|---|---|---|---|---|---|---|---|---|---|---|---|---|---|
| Asp | Glu | Ser | Val | Arg | Leu | Trp | Asn | Ile | His | Thr | Gly | Ile | Cys | Ile | Leu | |
| 150 | | | | | 155 | | | | | 160 | | | | | 165 | |

| ata | ttt | tct | ggt | gct | ggt | ggt | cat | cgc | aat | gaa | gtt | ctt | agt | gtg | gac | 584 |
|---|---|---|---|---|---|---|---|---|---|---|---|---|---|---|---|---|
| Ile | Phe | Ser | Gly | Ala | Gly | Gly | His | Arg | Asn | Glu | Val | Leu | Ser | Val | Asp | |
| | | | | 170 | | | | | 175 | | | | | 180 | | |

| ttc | cat | cct | tct | gac | atc | tac | cgt | att | gca | agc | tgt | gga | atg | gat | aac | 632 |
|---|---|---|---|---|---|---|---|---|---|---|---|---|---|---|---|---|
| Phe | His | Pro | Ser | Asp | Ile | Tyr | Arg | Ile | Ala | Ser | Cys | Gly | Met | Asp | Asn | |
| | | | 185 | | | | | 190 | | | | | 195 | | | |

| act | gtc | aag | atc | tgg | tca | atg | aaa | gaa | ttt | tgg | aca | tat | gta | gag | aaa | 680 |
|---|---|---|---|---|---|---|---|---|---|---|---|---|---|---|---|---|
| Thr | Val | Lys | Ile | Trp | Ser | Met | Lys | Glu | Phe | Trp | Thr | Tyr | Val | Glu | Lys | |
| | | 200 | | | | | 205 | | | | | 210 | | | | |

| tct | ttt | act | tgg | act | gat | ctt | cct | tct | aag | ttc | ccc | aca | aaa | tat | gtg | 728 |
|---|---|---|---|---|---|---|---|---|---|---|---|---|---|---|---|---|
| Ser | Phe | Thr | Trp | Thr | Asp | Leu | Pro | Ser | Lys | Phe | Pro | Thr | Lys | Tyr | Val | |
| | 215 | | | | | 220 | | | | | 225 | | | | | |

| cag | ttc | cca | ata | ttt | att | gct | tca | gtg | cat | acg | aac | tat | gtt | gat | tgc | 776 |
|---|---|---|---|---|---|---|---|---|---|---|---|---|---|---|---|---|
| Gln | Phe | Pro | Ile | Phe | Ile | Ala | Ser | Val | His | Thr | Asn | Tyr | Val | Asp | Cys | |
| 230 | | | | | 235 | | | | | 240 | | | | | 245 | |

| aac | cgg | tgg | att | ggt | gat | ttt | atg | ctc | tcc | aag | agc | gtt | gat | aat | gaa | 824 |
|---|---|---|---|---|---|---|---|---|---|---|---|---|---|---|---|---|
| Asn | Arg | Trp | Ile | Gly | Asp | Phe | Met | Leu | Ser | Lys | Ser | Val | Asp | Asn | Glu | |
| | | | | 250 | | | | | 255 | | | | | 260 | | |

| ctc | gta | tta | tgg | gaa | cca | aaa | atg | aaa | gaa | cag | tct | cct | gga | gag | ggt | 872 |
|---|---|---|---|---|---|---|---|---|---|---|---|---|---|---|---|---|
| Leu | Val | Leu | Trp | Glu | Pro | Lys | Met | Lys | Glu | Gln | Ser | Pro | Gly | Glu | Gly | |
| | | | 265 | | | | | 270 | | | | | 275 | | | |

```
aca gtc gac att ctt caa aag tat cct gtt ccc gaa tgc gat att tgg      920
Thr Val Asp Ile Leu Gln Lys Tyr Pro Val Pro Glu Cys Asp Ile Trp
        280                 285                 290 ttt atc aaa ttt tcc tgc gat ttc cat tac aag aca gca gca gta ggg      968
Phe Ile Lys Phe Ser Cys Asp Phe His Tyr Lys Thr Ala Ala Val Gly
    295                 300                 305 aac agg gaa gga aag ata tat gta tgg gaa gtg caa gcc aac ccc ccg     1016
Asn Arg Glu Gly Lys Ile Tyr Val Trp Glu Val Gln Ala Asn Pro Pro
310                 315                 320                 325 gtt ctc att gca aga tta tct cat att cag tcg aaa tct cca att aga     1064
Val Leu Ile Ala Arg Leu Ser His Ile Gln Ser Lys Ser Pro Ile Arg
                330                 335                 340 ttg act gcc atg tcc tat gat ggg agc acg att ctc tgc tgt tgt gaa     1112
Leu Thr Ala Met Ser Tyr Asp Gly Ser Thr Ile Leu Cys Cys Cys Glu
            345                 350                 355 gat gga acg ata tgg cga tgg gat gtg gta gca agt tct tga             1154
Asp Gly Thr Ile Trp Arg Trp Asp Val Val Ala Ser Ser *
        360                 365                 370 gcttctctaa cacccgtttg atggttatac ttataccatg attgatcaca aagctgtaat   1214
tgtactcaca caagctgcag cagaaaagca ctgggtgctg ccctttttaac ttatttcacc  1274 agaatattgg ttgtcattgt aaaacgtatc aattgtcatt cagttcttcg tttattcgta   1334
ccttccatca tttctatggt ctcttttctt gttgatgttt cacagctcac caaacatgaa   1394
aaggtaacag cgggtatagt tgtgtttcca tctc                               1428

<210> SEQ ID NO 14
<211> LENGTH: 370
<212> TYPE: PRT
<213> ORGANISM: Catalpa speciosa

<400> SEQUENCE: 14

Met Ala Lys Ile Pro Leu Gly Cys Glu Pro Met Val Gly Ser Leu Thr
1               5                   10                  15

Pro Ser Lys Lys Arg Glu Tyr Arg Val Thr Asn Arg Leu Gln Glu Gly
            20                  25                  30

Lys Arg Pro Ile Tyr Ala Val Val Phe Asn Phe Ile Asp Ser Arg Tyr
        35                  40                  45

Phe Asn Ala Phe Ala Thr Ala Gly Gly Asn Arg Val Thr Val Tyr Gln
    50                  55                  60

Cys Leu Glu Gly Gly Val Ile Ala Val Leu Gln Ser Tyr Ile Asp Glu
65                  70                  75                  80

Asp Lys Asp Glu Ser Phe Tyr Thr Val Ser Trp Ala Cys Asn Ile Asp
                85                  90                  95

Gly Thr Pro Phe Leu Val Ala Gly Gly Leu Asn Gly Ile Ile Arg Val
            100                 105                 110

Ile Asp Thr Gly Asn Glu Lys Ile Tyr Lys Ser Phe Val Gly His Gly
        115                 120                 125

Asp Ser Ile Asn Glu Ile Arg Thr Gln Pro Leu Lys Pro Ser Leu Val
    130                 135                 140

Val Ser Ala Ser Lys Asp Glu Ser Val Arg Leu Trp Asn Ile His Thr
145                 150                 155                 160

Gly Ile Cys Ile Leu Ile Phe Ser Gly Ala Gly His Arg Asn Glu
                165                 170                 175

Val Leu Ser Val Asp Phe His Pro Ser Asp Ile Tyr Arg Ile Ala Ser
            180                 185                 190
```

```
Cys Gly Met Asp Asn Thr Val Lys Ile Trp Ser Met Lys Glu Phe Trp
        195                 200                 205
Thr Tyr Val Glu Lys Ser Phe Thr Trp Thr Asp Leu Pro Ser Lys Phe
    210                 215                 220
Pro Thr Lys Tyr Val Gln Phe Pro Ile Phe Ile Ala Ser Val His Thr
225                 230                 235                 240
Asn Tyr Val Asp Cys Asn Arg Trp Ile Gly Asp Phe Met Leu Ser Lys
                245                 250                 255
Ser Val Asp Asn Glu Leu Val Leu Trp Glu Pro Lys Met Lys Glu Gln
                260                 265                 270
Ser Pro Gly Glu Gly Thr Val Asp Ile Leu Gln Lys Tyr Pro Val Pro
            275                 280                 285
Glu Cys Asp Ile Trp Phe Ile Lys Phe Ser Cys Asp Phe His Tyr Lys
        290                 295                 300
Thr Ala Ala Val Gly Asn Arg Glu Gly Lys Ile Tyr Val Trp Glu Val
305                 310                 315                 320
Gln Ala Asn Pro Pro Val Leu Ile Ala Arg Leu Ser His Ile Gln Ser
                325                 330                 335
Lys Ser Pro Ile Arg Leu Thr Ala Met Ser Tyr Asp Gly Ser Thr Ile
                340                 345                 350
Leu Cys Cys Cys Glu Asp Gly Thr Ile Trp Arg Trp Asp Val Val Ala
        355                 360                 365
Ser Ser
    370

<210> SEQ ID NO 15
<211> LENGTH: 637
<212> TYPE: DNA
<213> ORGANISM: Zea mays
<220> FEATURE:
<221> NAME/KEY: CDS
<222> LOCATION: (2)...(454)

<400> SEQUENCE: 15 t cca aca aaa tat gtc cag ttt cca gtc ttg att gct gca gta cac tct      49
  Pro Thr Lys Tyr Val Gln Phe Pro Val Leu Ile Ala Ala Val His Ser
    1               5                  10                  15 aac tat gtt gat tgt aca aga tgg ctt ggt gac ttc atc cta tca aag       97
Asn Tyr Val Asp Cys Thr Arg Trp Leu Gly Asp Phe Ile Leu Ser Lys
             20                  25                  30 agt gtt gac aat gaa att gtg ctt tgg gaa ccg aag aca aaa gaa cag      145
Ser Val Asp Asn Glu Ile Val Leu Trp Glu Pro Lys Thr Lys Glu Gln
         35                  40                  45 agt cct ggg gag gga agc atc gat atc ctt cag aag tat cct gtc cca      193
Ser Pro Gly Glu Gly Ser Ile Asp Ile Leu Gln Lys Tyr Pro Val Pro
     50                  55                  60 gaa tgt gac att tgg ttt atc aaa ttt tca tgt gat ttt cac ttc aat      241
Glu Cys Asp Ile Trp Phe Ile Lys Phe Ser Cys Asp Phe His Phe Asn
 65                  70                  75                  80 cag ttg gcg ata ggc aac cgt gaa ggc aaa atc tac gtg tgg gaa gta      289
Gln Leu Ala Ile Gly Asn Arg Glu Gly Lys Ile Tyr Val Trp Glu Val
                 85                  90                  95 cag tcc agc cct cct gtc ctc att gct cgg ctg tat aat cag cag tgt      337
Gln Ser Ser Pro Pro Val Leu Ile Ala Arg Leu Tyr Asn Gln Gln Cys
            100                 105                 110 aaa tcg ccg ata aga caa act gca gtg tcc ttc gat gga agc aca atc      385
Lys Ser Pro Ile Arg Gln Thr Ala Val Ser Phe Asp Gly Ser Thr Ile
        115                 120                 125
```

```
ctt gga gct ggt gaa gac ggc acc atc tgg cgg tgg gat gaa gtg gac    433
Leu Gly Ala Gly Glu Asp Gly Thr Ile Trp Arg Trp Asp Glu Val Asp
    130                 135                 140 cat ccg agc tcc aga aac tga agaagtgttg ccgctcaatg ctggactgat       484
His Pro Ser Ser Arg Asn *
145                 150 ggttacgctc ggttggggtt gcgatggttg aatccgttgg tggaaagtgc cacctggtgt  544
tttttctagt caaaatggtt ggtgttaaca gaatattgaa tgcttcgaat gttgaaagtt  604
gggatgcttg tgcttaaaaa aaaaaaaaaa aaa                                637

<210> SEQ ID NO 16
<211> LENGTH: 150
<212> TYPE: PRT
<213> ORGANISM: Zea mays

<400> SEQUENCE: 16

Pro Thr Lys Tyr Val Gln Phe Pro Val Leu Ile Ala Ala Val His Ser
  1               5                  10                  15

Asn Tyr Val Asp Cys Thr Arg Trp Leu Gly Asp Phe Ile Leu Ser Lys
                 20                  25                  30

Ser Val Asp Asn Glu Ile Val Leu Trp Glu Pro Lys Thr Lys Glu Gln
             35                  40                  45

Ser Pro Gly Glu Gly Ser Ile Asp Ile Leu Gln Lys Tyr Pro Val Pro
         50                  55                  60

Glu Cys Asp Ile Trp Phe Ile Lys Phe Ser Cys Asp Phe His Phe Asn
 65                  70                  75                  80

Gln Leu Ala Ile Gly Asn Arg Glu Gly Lys Ile Tyr Val Trp Glu Val
                 85                  90                  95

Gln Ser Ser Pro Pro Val Leu Ile Ala Arg Leu Tyr Asn Gln Gln Cys
            100                 105                 110

Lys Ser Pro Ile Arg Gln Thr Ala Val Ser Phe Asp Gly Ser Thr Ile
        115                 120                 125

Leu Gly Ala Gly Glu Asp Gly Thr Ile Trp Arg Trp Asp Glu Val Asp
    130                 135                 140

His Pro Ser Ser Arg Asn
145                 150

<210> SEQ ID NO 17
<211> LENGTH: 1486
<212> TYPE: DNA
<213> ORGANISM: Zea mays

<400> SEQUENCE: 17
ccytctagat gcatgctcga gcggccgcca gtgtgatgga tatctgcaga attcgccctt   60
gccgctctag aactagtgga tcccccgggc ctgcaggaat tcggcacgag ccggaagcgg  120
gagtacaagc ctgcggcaag cacactgagg ggaagcgccc gctatatgct atcgggttca  180
acttcatgga cgcgcgctac tacgacgtct tcgccaccgt cggcggcaac cgcgtgacaa  240
cttatcgctg ccttgagaat ggtagtttcg ctcttctaca agcttacgtt gatgaggata  300
aggatgagtc gttctatact ctaagctggg ctcgtgacca tgttgatggc tcaccactgc  360
tggtggcagc aggaagcaat gggatcattc ggtcatcaa ttgtgctaca gaaaagttag  420
ctaagagctt tgttggccat ggcgactcaa taaatgagat aagaactcaa ccgttgaagc  480
cttcgctcat catttctgca agcaaggatg aatctgttag ctatggaat gtccatacag  540 ggatctgtat cttgatattt gctggagctg gaggtcatcg caatgaagta ttgagtgttg  600
```

```
acttccatcc tagtgatatt gaacgttttg caagttgtgg catggacaac actgtgaaaa      660
tctggtcaat gaaagaattt tggctatatg ttgacaaatc atattcatgg actgaccttc      720
catcaaagtt tccaacaaaa tatgtccagt ttccagtctt gattgctgca gtacactcta      780
actatgttga ttgtacaaga tggcttggtg acttcatcct atcaaagagt gttgacaatg      840
aaattgtgct ttgggaaccg aagacaaaag aacagatcct gggggaggga agcatcgata      900
tccttcagaa gtatcctgtc ccagaatgtg acatttggtt tatcaaattt tcatgtgatt      960
ttcacttcaa tcagttggcg ataggcaacc gtgaaggcaa atctacgtg tgggaagtac     1020 agtcagccct cctgtcctca ttgctcggct gtataatcag cagtgtaaat cgccgataag     1080
acaaactgca gtgtccttcg atggaagcac aatccttgga gctggtgaag acggcaccat     1140
ctggcggtgg gatgaagtgg accatccgag ctccagaaac tgaagaagtg ttgccgctca     1200
atgctggact gatggttacg ctcggttggg gttgcgatgg ttgaatccgt tggtggaaag     1260
tgccacctgg tgttttttct agtcaaaatg gttggtgtta acagaatatt gaatgcttcg     1320
aatgttgaaa gttgggatgc ttgtgctggt actctgctcc gtggacgagt gaacttaggt     1380
gccgtttggt tcacatattt gtaacgtaat gggtaacaga taacgttaaa tcatgtttgt     1440
tttatttcaa ccgtaatcag ataccacatt aaaattaaaa aaaaaa                    1486
```

<210> SEQ ID NO 18
<211> LENGTH: 391
<212> TYPE: PRT
<213> ORGANISM: Zea mays

<400> SEQUENCE: 18

```
Met His Ala Arg Ala Ala Ala Ser Val Met Asp Ile Cys Arg Ile Arg
  1               5                  10                  15

Pro Cys Arg Ser Arg Thr Ser Gly Ser Pro Gly Pro Ala Gly Ile Arg
             20                  25                  30

His Glu Pro Glu Ala Gly Val Gln Ala Cys Gly Lys His Thr Glu Gly
         35                  40                  45

Lys Arg Pro Leu Tyr Ala Ile Gly Phe Asn Phe Met Asp Ala Arg Tyr
     50                  55                  60

Tyr Asp Val Phe Ala Thr Val Gly Gly Asn Arg Val Thr Thr Tyr Arg
 65                  70                  75                  80

Cys Leu Glu Asn Gly Ser Phe Ala Leu Leu Gln Ala Tyr Val Asp Glu
                 85                  90                  95

Asp Lys Asp Glu Ser Phe Tyr Thr Leu Ser Trp Ala Arg Asp His Val
            100                 105                 110

Asp Gly Ser Pro Leu Leu Val Ala Ala Gly Ser Asn Gly Ile Ile Arg
        115                 120                 125

Val Ile Asn Cys Ala Thr Glu Lys Leu Ala Lys Ser Phe Val Gly His
    130                 135                 140

Gly Asp Ser Ile Asn Glu Ile Arg Thr Gln Pro Leu Lys Pro Ser Leu
145                 150                 155                 160

Ile Ile Ser Ala Ser Lys Asp Glu Ser Val Arg Leu Trp Asn Val His
                165                 170                 175

Thr Gly Ile Cys Ile Leu Ile Phe Ala Gly Ala Gly Gly His Arg Asn
            180                 185                 190

Glu Val Leu Ser Val Asp Phe His Pro Ser Asp Ile Glu Arg Phe Ala
        195                 200                 205

Ser Cys Gly Met Asp Asn Thr Val Lys Ile Trp Ser Met Lys Glu Phe
```

```
                210                 215                 220
Trp Leu Tyr Val Asp Lys Ser Tyr Ser Trp Thr Asp Leu Pro Ser Lys
225                 230                 235                 240

Phe Pro Thr Lys Tyr Val Gln Phe Pro Val Leu Ile Ala Ala Val His
            245                 250                 255

Ser Asn Tyr Val Asp Cys Thr Arg Trp Leu Gly Asp Phe Ile Leu Ser
        260                 265                 270

Lys Ser Val Asp Asn Glu Ile Val Leu Trp Glu Pro Lys Thr Lys Glu
    275                 280                 285

Gln Ile Leu Gly Glu Gly Ser Ile Asp Ile Leu Gln Lys Tyr Pro Val
290                 295                 300

Pro Glu Cys Asp Ile Trp Phe Ile Lys Phe Ser Cys Asp Phe His Phe
305                 310                 315                 320

Asn Gln Leu Ala Ile Gly Asn Arg Glu Gly Lys Ile Tyr Val Trp Glu
            325                 330                 335

Val Gln Ser Ser Pro Pro Val Leu Ile Ala Arg Leu Tyr Asn Gln Gln
        340                 345                 350

Cys Lys Ser Pro Ile Arg Gln Thr Ala Val Ser Phe Asp Gly Ser Thr
    355                 360                 365

Ile Leu Gly Ala Gly Glu Asp Gly Thr Ile Trp Arg Trp Asp Glu Val
370                 375                 380

Asp His Pro Ser Ser Arg Asn
385                 390

<210> SEQ ID NO 19
<211> LENGTH: 1104
<212> TYPE: DNA
<213> ORGANISM: Zea mays
<220> FEATURE:
<221> NAME/KEY: CDS
<222> LOCATION: (62)...(823)

<400> SEQUENCE: 19
ccacgcgtcc ggaagcaatg ggatcattcg ggtcatcaat tgtgctacag aaaagttagc      60 t aag agc ttt gtt ggc cat ggc gac tca ata aat gag ata aga act caa    109
  Lys Ser Phe Val Gly His Gly Asp Ser Ile Asn Glu Ile Arg Thr Gln
    1               5                  10                  15 ccg ttg aag cct tcg ctc atc att tct gca agc aag gat gaa tct gtt    157
Pro Leu Lys Pro Ser Leu Ile Ile Ser Ala Ser Lys Asp Glu Ser Val
                20                  25                  30 agg cta tgg aat gtc cat aca ggg atc tgt atc ttg ata ttt gct gga    205
Arg Leu Trp Asn Val His Thr Gly Ile Cys Ile Leu Ile Phe Ala Gly
         35                  40                  45 gct gga ggt cat cgc aat gaa gta ttg agt gtt gac ttc cat cct agt    253
Ala Gly Gly His Arg Asn Glu Val Leu Ser Val Asp Phe His Pro Ser
     50                  55                  60 gat att gaa cgt ttt gca agt tgt ggc atg gac aac act gtg aaa atc    301
Asp Ile Glu Arg Phe Ala Ser Cys Gly Met Asp Asn Thr Val Lys Ile
 65                  70                  75                  80 tgg tca atg aaa gaa ttt tgg cta tat gtt gac aaa tca tat tca tgg    349
Trp Ser Met Lys Glu Phe Trp Leu Tyr Val Asp Lys Ser Tyr Ser Trp
                 85                  90                  95 act gac ctt cca tca aag ttt cca aca aaa tat gtc cag ttt cca gtc    397
Thr Asp Leu Pro Ser Lys Phe Pro Thr Lys Tyr Val Gln Phe Pro Val
            100                 105                 110 ttg att gct gca gta cac tct aac tat gtt gat tgt aca aga tgg ctt    445
Leu Ile Ala Ala Val His Ser Asn Tyr Val Asp Cys Thr Arg Trp Leu
        115                 120                 125
```

```
ggt gac ttc atc cta tca aag agt gtt gac aat gaa att gtg ctt tgg      493
Gly Asp Phe Ile Leu Ser Lys Ser Val Asp Asn Glu Ile Val Leu Trp
    130                 135                 140 gaa ccg aag aca aaa gaa cag agt cct ggg gag gga agc atc gat atc      541
Glu Pro Lys Thr Lys Glu Gln Ser Pro Gly Glu Gly Ser Ile Asp Ile
145                 150                 155                 160 ctt cag aag tat cct gtc cca gaa tgt gac att tgg ttt atc aaa ttt      589
Leu Gln Lys Tyr Pro Val Pro Glu Cys Asp Ile Trp Phe Ile Lys Phe
                165                 170                 175 tca tgt gat ttt cac ttc aat cag ttg gcg ata ggc aac cgt gaa ggc      637
Ser Cys Asp Phe His Phe Asn Gln Leu Ala Ile Gly Asn Arg Glu Gly
            180                 185                 190 aaa atc tac gtg tgg gaa gta cag tcc agc cct cct gtc ctc att gct      685
Lys Ile Tyr Val Trp Glu Val Gln Ser Ser Pro Pro Val Leu Ile Ala
        195                 200                 205 cgg ctg tat aat cag cag tgt aaa tcg ccg ata aga caa act gca gtg      733
Arg Leu Tyr Asn Gln Gln Cys Lys Ser Pro Ile Arg Gln Thr Ala Val
    210                 215                 220 tcc ttc gat gga agc aca atc ctt gga gct ggt gaa gac ggc acc atc      781
Ser Phe Asp Gly Ser Thr Ile Leu Gly Ala Gly Glu Asp Gly Thr Ile
225                 230                 235                 240 tgg cgg tgg gat gaa gtg gac cat ccg agc tcc aga aac tga              823
Trp Arg Trp Asp Glu Val Asp His Pro Ser Ser Arg Asn *
                245                 250 agaagtgttg ccgctcaatg ctggactgat ggttacgctc ggttgggggtt gcgatggttg    883 aatccgttgg tggaaagtgc cacctggtgt tttttctagt caaaatggtt ggtgttaaca    943
gaatattgaa tgcttcgaat gttgaaagtt gggatgcttg tgctggtact ctgctccgtg   1003
gacgagtgaa cttaggtgcc gtttggttca catatttgta acgtaatggg taacagataa   1063
cgttaaatca tgtttgtttt atttcaaaaa aaaaaaaaa g                        1104
```

<210> SEQ ID NO 20
<211> LENGTH: 253
<212> TYPE: PRT
<213> ORGANISM: Zea mays

<400> SEQUENCE: 20

```
Lys Ser Phe Val Gly His Gly Asp Ser Ile Asn Glu Ile Arg Thr Gln
1               5                   10                  15

Pro Leu Lys Pro Ser Leu Ile Ile Ser Ala Ser Lys Asp Glu Ser Val
            20                  25                  30

Arg Leu Trp Asn Val His Thr Gly Ile Cys Ile Leu Ile Phe Ala Gly
        35                  40                  45

Ala Gly His Arg Asn Glu Val Leu Ser Val Asp Phe His Pro Ser
    50                  55                  60

Asp Ile Glu Arg Phe Ala Ser Cys Gly Met Asp Asn Thr Val Lys Ile
65                  70                  75                  80

Trp Ser Met Lys Glu Phe Trp Leu Tyr Val Asp Lys Ser Tyr Ser Trp
                85                  90                  95

Thr Asp Leu Pro Ser Lys Phe Pro Thr Lys Tyr Val Gln Phe Pro Val
            100                 105                 110

Leu Ile Ala Ala Val His Ser Asn Tyr Val Asp Cys Thr Arg Trp Leu
        115                 120                 125

Gly Asp Phe Ile Leu Ser Lys Ser Val Asp Asn Glu Ile Val Leu Trp
    130                 135                 140

Glu Pro Lys Thr Lys Glu Gln Ser Pro Gly Glu Gly Ser Ile Asp Ile
```

```
                145                 150                 155                 160
Leu Gln Lys Tyr Pro Val Pro Glu Cys Asp Ile Trp Phe Ile Lys Phe
                    165                 170                 175

Ser Cys Asp Phe His Phe Asn Gln Leu Ala Ile Gly Asn Arg Glu Gly
                180                 185                 190

Lys Ile Tyr Val Trp Glu Val Gln Ser Ser Pro Val Leu Ile Ala
            195                 200                 205

Arg Leu Tyr Asn Gln Gln Cys Lys Ser Pro Ile Arg Gln Thr Ala Val
        210                 215                 220

Ser Phe Asp Gly Ser Thr Ile Leu Gly Ala Gly Glu Asp Gly Thr Ile
225                 230                 235                 240

Trp Arg Trp Asp Glu Val Asp His Pro Ser Ser Arg Asn
                245                 250

<210> SEQ ID NO 21
<211> LENGTH: 476
<212> TYPE: DNA
<213> ORGANISM: Zea mays
<220> FEATURE:
<221> NAME/KEY: CDS
<222> LOCATION: (1)...(189)

<400> SEQUENCE: 21 ggc aaa atc tac gtg tgg gaa gta cag tcc agc cct cct gtc ctc att     48
Gly Lys Ile Tyr Val Trp Glu Val Gln Ser Ser Pro Pro Val Leu Ile
 1               5                  10                  15 gct cgg ctg tat aat cag cag tgt aaa tcg ccg ata aga caa act gca     96
Ala Arg Leu Tyr Asn Gln Gln Cys Lys Ser Pro Ile Arg Gln Thr Ala
                20                  25                  30 gtg tcc ttc gat gga agc aca atc ctt gga gct ggt gaa gac ggc acc    144
Val Ser Phe Asp Gly Ser Thr Ile Leu Gly Ala Gly Glu Asp Gly Thr
            35                  40                  45 atc tgg cgg tgg gat gaa gtg gac cat ccg agc tcc aga aac tga        189
Ile Trp Arg Trp Asp Glu Val Asp His Pro Ser Ser Arg Asn  *
        50                  55                  60 agaagtgttg ccgctcaatg ctggactgat ggttacgctc ggttgggggtt gcgatggttg  249 aatccgttgg tggaaagtgc cacctggtgt tttttctagt caaaatggtt ggtgttaaca  309
gaatattgaa tgcttcgaat gttgaaagtt gggatgcttg tgctggtact ctgctccgtg  369
gacgagtgaa cttaggtgcc gtttggttca catatttgta acgtaatggg taacagataa  429
cgttaaatca tgtttgtttt atttcaaccg taaaaaaaaa aaaaaaa                 476

<210> SEQ ID NO 22
<211> LENGTH: 62
<212> TYPE: PRT
<213> ORGANISM: Zea mays

<400> SEQUENCE: 22

Gly Lys Ile Tyr Val Trp Glu Val Gln Ser Ser Pro Pro Val Leu Ile
 1               5                  10                  15

Ala Arg Leu Tyr Asn Gln Gln Cys Lys Ser Pro Ile Arg Gln Thr Ala
                20                  25                  30

Val Ser Phe Asp Gly Ser Thr Ile Leu Gly Ala Gly Glu Asp Gly Thr
            35                  40                  45

Ile Trp Arg Trp Asp Glu Val Asp His Pro Ser Ser Arg Asn
        50                  55                  60

<210> SEQ ID NO 23
```

```
<211> LENGTH: 1751
<212> TYPE: DNA
<213> ORGANISM: Zea mays
<220> FEATURE:
<221> NAME/KEY: CDS
<222> LOCATION: (168)...(1163)

<400> SEQUENCE: 23
caaaatgtgc atcgccgccg ccaccatata gaaccactta tcatgaaccg ccgccatcac     60
atccactgcc tcaactagtg ttaccaccta tggttcattg ttgtgtctgc ttcttgtagc    120
actgttggtc tacaaacatt catatttctc tcaacatctg gcacagc atg ccg cct      176
                                                   Met Pro Pro
                                                     1 tcc aaa gca cgc cga aag agg tca ctt cgt gat atc act gcc acc gtt      224
Ser Lys Ala Arg Arg Lys Arg Ser Leu Arg Asp Ile Thr Ala Thr Val
  5                  10                  15 gcc act ggg act gtt gcc aac tcg aaa cct ggc tca tca tcg acg aac      272
Ala Thr Gly Thr Val Ala Asn Ser Lys Pro Gly Ser Ser Ser Thr Asn
 20                  25                  30                  35 gag ggg aag caa cag gac aag aaa aag gag ggt cca cag gaa ccg gac      320
Glu Gly Lys Gln Gln Asp Lys Lys Lys Glu Gly Pro Gln Glu Pro Asp
             40                  45                  50 atc cca cca tta ccg ccg gtg gtg gtg aat ata gtc cca cga caa gga      368
Ile Pro Pro Leu Pro Pro Val Val Val Asn Ile Val Pro Arg Gln Gly
 55                  60                  65 tta gga tgt gaa gta gtg gaa ggg cta ctc gtg cct agt cgg aag cga      416
Leu Gly Cys Glu Val Val Glu Gly Leu Leu Val Pro Ser Arg Lys Arg
         70                  75                  80 gag tac aag ccc aat agc aag tat act gtg gga aat cac ccg atc tat      464
Glu Tyr Lys Pro Asn Ser Lys Tyr Thr Val Gly Asn His Pro Ile Tyr
 85                  90                  95 gcc atc ggg ttc aat ttc att gac atg cgc tac tat gat gtc ttt gcc      512
Ala Ile Gly Phe Asn Phe Ile Asp Met Arg Tyr Tyr Asp Val Phe Ala
100                 105                 110                 115 atc gcc agt tgc aat agt gtg ata att tac cga tgc ctt gag aat ggt      560
Ile Ala Ser Cys Asn Ser Val Ile Ile Tyr Arg Cys Leu Glu Asn Gly
                120                 125                 130 ggt ttt ggt ctt cta caa aat tat gtt gat gag gat aag gat gag tca      608
Gly Phe Gly Leu Leu Gln Asn Tyr Val Asp Glu Asp Lys Asp Glu Ser
            135                 140                 145 ttc tac act cta agc tgg acc atc gat caa gtt gat agc tca ccg ctg      656
Phe Tyr Thr Leu Ser Trp Thr Ile Asp Gln Val Asp Ser Ser Pro Leu
        150                 155                 160 ttg gtg gcc gca gga agc aat cgg atc att cgg gtc atc aat tgt gct      704
Leu Val Ala Ala Gly Ser Asn Arg Ile Ile Arg Val Ile Asn Cys Ala
165                 170                 175 acc gaa aag tta gat aag agc tta gtt ggc cat ggt ggt tca ata cat      752
Thr Glu Lys Leu Asp Lys Ser Leu Val Gly His Gly Gly Ser Ile His
180                 185                 190                 195 gag ata agg act cat gcc tcg aag cca tca ctc atc att tct gcc agc      800
Glu Ile Arg Thr His Ala Ser Lys Pro Ser Leu Ile Ile Ser Ala Ser
                200                 205                 210 aag gac ttc cac cct acc gag gtt ggg att ttt gca agt tgt ggc atg      848
Lys Asp Phe His Pro Thr Glu Val Gly Ile Phe Ala Ser Cys Gly Met
            215                 220                 225 gac aat act gtg aaa att tgg tca atg aaa gaa ttt tgg ata tat gtt      896
Asp Asn Thr Val Lys Ile Trp Ser Met Lys Glu Phe Trp Ile Tyr Val
        230                 235                 240 gaa aaa tca tat tca tgg act ggc cat cca tca aag ttt cca acg agg      944
Glu Lys Ser Tyr Ser Trp Thr Gly His Pro Ser Lys Phe Pro Thr Arg
```

```
                     245                 250                 255
aat atc cag ttt ccg gtc ttg act gct gca gta cac tct gac tat gtt         992
Asn Ile Gln Phe Pro Val Leu Thr Ala Ala Val His Ser Asp Tyr Val
260                 265                 270                 275 gat tgt aca aga tgg ctt ggt gac ttc atc cta tca aag agt gta aag        1040
Asp Cys Thr Arg Trp Leu Gly Asp Phe Ile Leu Ser Lys Ser Val Lys
                280                 285                 290 aat gca gtt ttg ctt tgg gaa cca aaa cca gac aag cgt agg cct ggg        1088
Asn Ala Val Leu Leu Trp Glu Pro Lys Pro Asp Lys Arg Arg Pro Gly
            295                 300                 305 gag ggg agt gtt gat gtt ctt cag aag tac ccg gtg cca aag tgt tca        1136
Glu Gly Ser Val Asp Val Leu Gln Lys Tyr Pro Val Pro Lys Cys Ser
        310                 315                 320 ttt atg gtt tat gaa att ttc atg tga tttttactcc aaccagatgg              1183
Phe Met Val Tyr Glu Ile Phe Met  *
325                 330 caataggcaa caataaaggc gagatctatg tctgggaagt gcagtccagc ccgcccgtct      1243
taattgaccg gctgtgcaac caggaatgca agtcgccgat aaggcagacc gcagtgtcat      1303
tcgacggaag cacgatcctt ggagccgccg acgacggcgc gatctggcgg tgggacgaag      1363
tggaccctgc tgcttccagc tccaaacctg atcaagctgc tgcgcccgcc gccggtgtcg      1423
gtgccggtgc cggtgccgac gccgacgccg acgcctgagc gagaggaccg tcgccgcccg      1483
ccggttcaca tcgatcgtac tccgtgctgg ttgattagct ttacccattg gtatgttttg      1543
gttcagagtc gccagatcta gtgtgtggct gaacgttgaa tgttaggatg ctgctgtttg      1603
ttatgctctg agtcttgagt tcactttgtt aatttgcacc gtggatgaga tgaataactt      1663
gacgttgcaa ctttgcatcc catatatgcc gtaaatctgc cgtctgttgt ttgtaaaaaa      1723
aaaaaaaaaa aaaaaaaaa aaaaaaaa                                          1751

<210> SEQ ID NO 24
<211> LENGTH: 331
<212> TYPE: PRT
<213> ORGANISM: Zea mays

<400> SEQUENCE: 24

Met Pro Pro Ser Lys Ala Arg Lys Arg Ser Leu Arg Asp Ile Thr
1               5                   10                  15

Ala Thr Val Ala Thr Gly Thr Val Ala Asn Ser Lys Pro Gly Ser Ser
                20                  25                  30

Ser Thr Asn Glu Gly Lys Gln Gln Asp Lys Lys Glu Gly Pro Gln
        35                  40                  45

Glu Pro Asp Ile Pro Pro Leu Pro Val Val Asn Ile Val Pro
50                  55                  60

Arg Gln Gly Leu Gly Cys Glu Val Val Glu Gly Leu Leu Val Pro Ser
65                  70                  75                  80

Arg Lys Arg Glu Tyr Lys Pro Asn Ser Lys Tyr Thr Val Gly Asn His
                85                  90                  95

Pro Ile Tyr Ala Ile Gly Phe Asn Phe Ile Asp Met Arg Tyr Tyr Asp
                100                 105                 110

Val Phe Ala Ile Ala Ser Cys Asn Ser Val Ile Ile Tyr Arg Cys Leu
            115                 120                 125

Glu Asn Gly Gly Phe Gly Leu Leu Gln Asn Tyr Val Asp Glu Asp Lys
        130                 135                 140

Asp Glu Ser Phe Tyr Thr Leu Ser Trp Thr Ile Asp Gln Val Asp Ser
145                 150                 155                 160
```

```
Ser Pro Leu Leu Val Ala Ala Gly Ser Asn Arg Ile Ile Arg Val Ile
                165                 170                 175

Asn Cys Ala Thr Glu Lys Leu Asp Lys Ser Leu Val Gly His Gly Gly
            180                 185                 190

Ser Ile His Glu Ile Arg Thr His Ala Ser Lys Pro Ser Leu Ile Ile
        195                 200                 205

Ser Ala Ser Lys Asp Phe His Pro Thr Glu Val Gly Ile Phe Ala Ser
    210                 215                 220

Cys Gly Met Asp Asn Thr Val Lys Ile Trp Ser Met Lys Glu Phe Trp
225                 230                 235                 240

Ile Tyr Val Glu Lys Ser Tyr Ser Trp Thr Gly His Pro Ser Lys Phe
                245                 250                 255

Pro Thr Arg Asn Ile Gln Phe Pro Val Leu Thr Ala Ala Val His Ser
            260                 265                 270

Asp Tyr Val Asp Cys Thr Arg Trp Leu Gly Asp Phe Ile Leu Ser Lys
        275                 280                 285

Ser Val Lys Asn Ala Val Leu Leu Trp Glu Pro Lys Pro Asp Lys Arg
    290                 295                 300

Arg Pro Gly Glu Gly Ser Val Asp Val Leu Gln Lys Tyr Pro Val Pro
305                 310                 315                 320

Lys Cys Ser Phe Met Val Tyr Glu Ile Phe Met
                325                 330

<210> SEQ ID NO 25
<211> LENGTH: 1803
<212> TYPE: DNA
<213> ORGANISM: Zea mays
<220> FEATURE:
<221> NAME/KEY: CDS
<222> LOCATION: (490)...(1629)
<220> FEATURE:
<221> NAME/KEY: misc_feature
<222> LOCATION: 1729, 1752, 1760, 1765
<223> OTHER INFORMATION: n = A, T, C, or G

<400> SEQUENCE: 25
gcacgaggct tttgccccgc accgctttcc tacgcttgcc caaacccaca aaaccctggc     60
cgatcgcgcc gcggaaatgc ctttccggcc gccgcgagcc cgcgacacta gtaacggtct    120
acaccactag aatgactgaa gaatttgaat tccagcaaaa ttcaagcttt tgttttaagc    180
caagattttg agatttcgat ttgaagtgtg gaagtcctta caattttgcc aattcctata    240
tttgatctct gctgtgctgc gttaaatccc taaactttca cagcgcggcg ccgggcccag    300
ccacgccgga agaagtcgcc gcgtgaggtc agtgtcccg ttgctgccgc ctctaacccg     360
aagcctaggc cgctgccggt gcataacaag gagaatcagg cggaggggaa agtagcagag    420 gaggggcag caactgagga gggggagaag taccgggcgg aaccggaaat cttgccgctg     480 ccgccggcc atg gcg aag ctg ggc ccg ggg cag ggg ctc ggg tgc gag gcg   531
           Met Ala Lys Leu Gly Pro Gly Gln Gly Leu Gly Cys Glu Ala
             1               5                  10 gcg gag ggg tcg ctc gtg ccc agc cgg aag cgg gag tac aag ccc tgc     579
Ala Glu Gly Ser Leu Val Pro Ser Arg Lys Arg Glu Tyr Lys Pro Cys
 15                  20                  25                  30 ggc aag cac act gag ggg aag cgc ccg cta tat gct atc ggg ttc aac     627
Gly Lys His Thr Glu Gly Lys Arg Pro Leu Tyr Ala Ile Gly Phe Asn
             35                  40                  45 ttc atg gac gcg cgc tac tac gac gtc ttc gcc acc gtc ggc ggc aac     675
Phe Met Asp Ala Arg Tyr Tyr Asp Val Phe Ala Thr Val Gly Gly Asn
         50                  55                  60
```

-continued

```
                  50                  55                  60
cgc gtg aca act tac cgc tgc ctt gag aat ggt agt ttc gct ctt cta      723
Arg Val Thr Thr Tyr Arg Cys Leu Glu Asn Gly Ser Phe Ala Leu Leu
                  65                  70                  75 caa gct tac gtt gat gag gat aag gat gag tcg ttc tat act cta agc      771
Gln Ala Tyr Val Asp Glu Asp Lys Asp Glu Ser Phe Tyr Thr Leu Ser
             80                  85                  90 tgg gct cgt gac cat gtt gat ggc tca cca ctg ctg gtg gca gca gga      819
Trp Ala Arg Asp His Val Asp Gly Ser Pro Leu Leu Val Ala Ala Gly
 95                 100                 105                 110 agc aat ggg atc att cgg gtc atc aat tgt gct aca gaa aag tta gct      867
Ser Asn Gly Ile Ile Arg Val Ile Asn Cys Ala Thr Glu Lys Leu Ala
                 115                 120                 125 aag agc ttt gtt ggc cat ggc gac tca ata aat gag ata aga act caa      915
Lys Ser Phe Val Gly His Gly Asp Ser Ile Asn Glu Ile Arg Thr Gln
             130                 135                 140 ccg ttg aag cct tcg ctc atc att tct gca agc aag gat gaa tct gtt      963
Pro Leu Lys Pro Ser Leu Ile Ile Ser Ala Ser Lys Asp Glu Ser Val
            145                 150                 155 agg cta tgg aat gtc cat aca ggg atc tgt atc ttg ata ttt gct gga     1011
Arg Leu Trp Asn Val His Thr Gly Ile Cys Ile Leu Ile Phe Ala Gly
    160                 165                 170 gct gga ggt cat cgc aat gaa gta ttg agt gtt gac ttc cat cct agt     1059
Ala Gly Gly His Arg Asn Glu Val Leu Ser Val Asp Phe His Pro Ser
175                 180                 185                 190 gat att gaa cgt ttt gca agt tgt ggc atg gac aac act gtg aaa atc     1107
Asp Ile Glu Arg Phe Ala Ser Cys Gly Met Asp Asn Thr Val Lys Ile
                 195                 200                 205 tgg tca atg aaa gaa ttt tgg cta tat gtt gac aaa tca tat tca tgg     1155
Trp Ser Met Lys Glu Phe Trp Leu Tyr Val Asp Lys Ser Tyr Ser Trp
             210                 215                 220 act gac ctt cca tca aag ttt cca aca aaa tat gtc cag ttt cca gtc     1203
Thr Asp Leu Pro Ser Lys Phe Pro Thr Lys Tyr Val Gln Phe Pro Val
 225                 230                 235 ttg att gct gca gta cac tct aac tat gtt gat tgt aca aga tgg ctt     1251
Leu Ile Ala Ala Val His Ser Asn Tyr Val Asp Cys Thr Arg Trp Leu
 240                 245                 250 ggt gac ttc atc cta tca aag agt gtt gac aat gaa ttg tgc ttt tgg     1299
Gly Asp Phe Ile Leu Ser Lys Ser Val Asp Asn Glu Leu Cys Phe Trp
255                 260                 265                 270 gaa ccg aag aca aaa gaa cag agt cct ggg gag gga agc atc gat atc     1347
Glu Pro Lys Thr Lys Glu Gln Ser Pro Gly Glu Gly Ser Ile Asp Ile
                 275                 280                 285 ctt cag aag tat cct gtc cca gaa tgt gac att tgg ttt atc aaa ttt     1395
Leu Gln Lys Tyr Pro Val Pro Glu Cys Asp Ile Trp Phe Ile Lys Phe
             290                 295                 300 tca tgt gat ttt cac ttc aat cag ttg gcg ata ggc aac cgt gaa ggc     1443
Ser Cys Asp Phe His Phe Asn Gln Leu Ala Ile Gly Asn Arg Glu Gly
 305                 310                 315 aaa atc tac gtg tgg gaa gta cag tcc agc cct cct gtc ctc att gct     1491
Lys Ile Tyr Val Trp Glu Val Gln Ser Ser Pro Pro Val Leu Ile Ala
 320                 325                 330 cgg ctg tat aat cag cag tgt aaa tcg cca ata aga caa act gca gtg     1539
Arg Leu Tyr Asn Gln Gln Cys Lys Ser Pro Ile Arg Gln Thr Ala Val
335                 340                 345                 350 tcc ttc gat gga agc aca atc ctt gga gct ggt gaa gac ggc acc atc     1587
Ser Phe Asp Gly Ser Thr Ile Leu Gly Ala Gly Glu Asp Gly Thr Ile
                 355                 360                 365 tgg cgg tgg gat gaa gtg gac cat ccg agc tcc aga aac tga             1629
```

Trp Arg Trp Asp Glu Val Asp His Pro Ser Ser Arg Asn *
                370                 375 agaagtgttg ccgctcaatg ctggactgat ggttacgctc ggttgggtt gcgatggttg    1689 aatccgttgg tggaaagtgc cacctgggtg ttttttctan tcaaaatggg ttggtgttaa    1749
canaatattg naatgnttcc aaatgttgaa aaatttggga tgcttgtgcc tggt    1803

<210> SEQ ID NO 26
<211> LENGTH: 379
<212> TYPE: PRT
<213> ORGANISM: Zea mays
<220> FEATURE:
<221> NAME/KEY: VARIANT
<222> LOCATION: (1)...(594)
<223> OTHER INFORMATION: Xaa = Any Amino Acid

<400> SEQUENCE: 26

Met Ala Lys Leu Gly Pro Gly Gln Gly Leu Gly Cys Glu Ala Ala Glu
 1               5                  10                  15

Gly Ser Leu Val Pro Ser Arg Lys Arg Glu Tyr Lys Pro Cys Gly Lys
             20                  25                  30

His Thr Glu Gly Lys Arg Pro Leu Tyr Ala Ile Gly Phe Asn Phe Met
         35                  40                  45

Asp Ala Arg Tyr Tyr Asp Val Phe Ala Thr Val Gly Gly Asn Arg Val
     50                  55                  60

Thr Thr Tyr Arg Cys Leu Glu Asn Gly Ser Phe Ala Leu Leu Gln Ala
 65                  70                  75                  80

Tyr Val Asp Glu Asp Lys Asp Glu Ser Phe Tyr Thr Leu Ser Trp Ala
                 85                  90                  95

Arg Asp His Val Asp Gly Ser Pro Leu Leu Val Ala Ala Gly Ser Asn
            100                 105                 110

Gly Ile Ile Arg Val Ile Asn Cys Ala Thr Glu Lys Leu Ala Lys Ser
        115                 120                 125

Phe Val Gly His Gly Asp Ser Ile Asn Glu Ile Arg Thr Gln Pro Leu
    130                 135                 140

Lys Pro Ser Leu Ile Ile Ser Ala Ser Lys Asp Glu Ser Val Arg Leu
145                 150                 155                 160

Trp Asn Val His Thr Gly Ile Cys Ile Leu Ile Phe Ala Gly Ala Gly
                165                 170                 175

Gly His Arg Asn Glu Val Leu Ser Val Asp Phe His Pro Ser Asp Ile
            180                 185                 190

Glu Arg Phe Ala Ser Cys Gly Met Asp Asn Thr Val Lys Ile Trp Ser
        195                 200                 205

Met Lys Glu Phe Trp Leu Tyr Val Asp Lys Ser Tyr Ser Trp Thr Asp
    210                 215                 220

Leu Pro Ser Lys Phe Pro Thr Lys Tyr Val Gln Phe Pro Val Leu Ile
225                 230                 235                 240

Ala Ala Val His Ser Asn Tyr Val Asp Cys Thr Arg Trp Leu Gly Asp
                245                 250                 255

Phe Ile Leu Ser Lys Ser Val Asp Asn Glu Leu Cys Phe Trp Glu Pro
            260                 265                 270

Lys Thr Lys Glu Gln Ser Pro Gly Glu Gly Ser Ile Asp Ile Leu Gln
        275                 280                 285

Lys Tyr Pro Val Pro Glu Cys Asp Ile Trp Phe Ile Lys Phe Ser Cys
    290                 295                 300

Asp Phe His Phe Asn Gln Leu Ala Ile Gly Asn Arg Glu Gly Lys Ile

```
                305                 310                 315                 320
Tyr Val Trp Glu Val Gln Ser Ser Pro Val Leu Ile Ala Arg Leu
                    325                 330                 335

Tyr Asn Gln Gln Cys Lys Ser Pro Ile Arg Gln Thr Ala Val Ser Phe
                340                 345                 350

Asp Gly Ser Thr Ile Leu Gly Ala Gly Glu Asp Gly Thr Ile Trp Arg
                355                 360                 365

Trp Asp Glu Val Asp His Pro Ser Ser Arg Asn
            370                 375

<210> SEQ ID NO 27
<211> LENGTH: 1629
<212> TYPE: DNA
<213> ORGANISM: Zea mays
<220> FEATURE:
<221> NAME/KEY: CDS
<222> LOCATION: (17)...(1402)

<400> SEQUENCE: 27
caacatctgg cacagc atg ccg cct tcc aaa gca cgc cga aag agg tca ctt        52
                Met Pro Pro Ser Lys Ala Arg Arg Lys Arg Ser Leu
                  1               5                  10 cgt gat atc act gcc acc gtt gcc act ggg act gtt gcc aac tcg aaa        100
Arg Asp Ile Thr Ala Thr Val Ala Thr Gly Thr Val Ala Asn Ser Lys
        15                  20                  25 cct ggc tca tca tcg acg aac gag ggg aag caa cag gac aag aaa aag        148
Pro Gly Ser Ser Ser Thr Asn Glu Gly Lys Gln Gln Asp Lys Lys Lys
 30                  35                  40 gag ggt cca cag gaa ccg gac atc cca cca tta ccg ccg gtg gtg gtg        196
Glu Gly Pro Gln Glu Pro Asp Ile Pro Pro Leu Pro Pro Val Val Val
 45                  50                  55                  60 aat ata gtc cca cga caa gga tta gga tgt gaa gta gtg gaa ggg cta        244
Asn Ile Val Pro Arg Gln Gly Leu Gly Cys Glu Val Val Glu Gly Leu
                 65                  70                  75 ctc gtg cct agt cgg aag cga gag tac aag ccc aat agc aag tat act        292
Leu Val Pro Ser Arg Lys Arg Glu Tyr Lys Pro Asn Ser Lys Tyr Thr
             80                  85                  90 gtg gga aat cac ccg atc tat gcc atc ggg ttc aat ttc att gac atg        340
Val Gly Asn His Pro Ile Tyr Ala Ile Gly Phe Asn Phe Ile Asp Met
         95                 100                 105 cgc tac tat gat gtc ttt gcc atc gcc agt tgc aat agt gtg ata att        388
Arg Tyr Tyr Asp Val Phe Ala Ile Ala Ser Cys Asn Ser Val Ile Ile
    110                 115                 120 tac cga tgc ctt gag aat ggt ggt ttt ggt ctt cta caa aat tat gtt        436
Tyr Arg Cys Leu Glu Asn Gly Gly Phe Gly Leu Leu Gln Asn Tyr Val
125                 130                 135                 140 gat gag gat aag gat gag tca ttc tac act cta agc tgg acc atc gat        484
Asp Glu Asp Lys Asp Glu Ser Phe Tyr Thr Leu Ser Trp Thr Ile Asp
                145                 150                 155 caa gtt gat agc tca ccg ctg ttg gtg gcc gca gga agc aat cgg atc        532
Gln Val Asp Ser Ser Pro Leu Leu Val Ala Ala Gly Ser Asn Arg Ile
            160                 165                 170 att cgg gtc atc aat tgt gct acc gaa aag tta gat aag agc tta gtt        580
Ile Arg Val Ile Asn Cys Ala Thr Glu Lys Leu Asp Lys Ser Leu Val
        175                 180                 185 ggc cat ggt ggt tca ata cat gag ata agg act cat gcc tcg aag cca        628
Gly His Gly Gly Ser Ile His Glu Ile Arg Thr His Ala Ser Lys Pro
    190                 195                 200 tca ctc atc att tct gcc agc aag gat gaa tct att agg cta tgg aat        676
Ser Leu Ile Ile Ser Ala Ser Lys Asp Glu Ser Ile Arg Leu Trp Asn
```

```
                205                 210                 215                 220
gtc cat act ggg att tgc atc tta gtc ttt gca ggg gct gga ggc cat        724
Val His Thr Gly Ile Cys Ile Leu Val Phe Ala Gly Ala Gly Gly His
                225                 230                 235 cga cat gat gtg ttg agt gtt gac ttc cac cct acc gag gtt ggg att        772
Arg His Asp Val Leu Ser Val Asp Phe His Pro Thr Glu Val Gly Ile
            240                 245                 250 ttt gca agt tgt ggc atg gac aat act gtg aaa att tgg tca atg aaa        820
Phe Ala Ser Cys Gly Met Asp Asn Thr Val Lys Ile Trp Ser Met Lys
        255                 260                 265 gaa ttt tgg ata tat gtt gaa aaa tca tat tca tgg act ggc cat cca        868
Glu Phe Trp Ile Tyr Val Glu Lys Ser Tyr Ser Trp Thr Gly His Pro
    270                 275                 280 tca aag ttt cca acg agg aat atc cag ttt ccg gtc ttg act gct gca        916
Ser Lys Phe Pro Thr Arg Asn Ile Gln Phe Pro Val Leu Thr Ala Ala
285                 290                 295                 300 gta cac tct gac tat gtt gat tgt aca aga tgg ctt ggt gac ttc atc        964
Val His Ser Asp Tyr Val Asp Cys Thr Arg Trp Leu Gly Asp Phe Ile
                305                 310                 315 cta tca aag agt gta aag aat gca gtt ttg ctt tgg gaa cca aaa cca       1012
Leu Ser Lys Ser Val Lys Asn Ala Val Leu Leu Trp Glu Pro Lys Pro
            320                 325                 330 gac aag cgt agg cct ggg gag ggg agt gtt gat gtt ctt cag aag tac       1060
Asp Lys Arg Arg Pro Gly Glu Gly Ser Val Asp Val Leu Gln Lys Tyr
        335                 340                 345 ccg gtg cca aag tgt tca tta tgg ttt atg aaa ttt tca tgt gat ttt       1108
Pro Val Pro Lys Cys Ser Leu Trp Phe Met Lys Phe Ser Cys Asp Phe
    350                 355                 360 tac tcc aac cag atg gca ata ggc aac aat aaa ggc gag atc tat gtc       1156
Tyr Ser Asn Gln Met Ala Ile Gly Asn Asn Lys Gly Glu Ile Tyr Val
365                 370                 375                 380 tgg gaa gtg cag tcc agc ccg ccc gtc tta att gac cgg ctg tgc aac       1204
Trp Glu Val Gln Ser Ser Pro Pro Val Leu Ile Asp Arg Leu Cys Asn
                385                 390                 395 cag gaa tgc aag tcg ccg ata agg cag acc gca gtg tca ttc gac gga       1252
Gln Glu Cys Lys Ser Pro Ile Arg Gln Thr Ala Val Ser Phe Asp Gly
            400                 405                 410 agc acg atc ctt gga gcc gcc gac gac ggc gcg atc tgg cgg tgg gac       1300
Ser Thr Ile Leu Gly Ala Ala Asp Asp Gly Ala Ile Trp Arg Trp Asp
        415                 420                 425 gaa gtg gac cct gct gct tcc agc tcc aaa cct gat caa gct gct gcg       1348
Glu Val Asp Pro Ala Ala Ser Ser Ser Lys Pro Asp Gln Ala Ala Ala
    430                 435                 440 ccc gcc gcc ggt gtc ggt gcc ggt gcc ggt gcc gac gcc gac gcc gac       1396
Pro Ala Ala Gly Val Gly Ala Gly Ala Gly Ala Asp Ala Asp Ala Asp
445                 450                 455                 460 gcc tga gcgagggac cgtcgccgcc cgccggttca catcgatcgt actccgtgct         1452
Ala * ggttgattag ctttacccat tggtatgttt tggttcagag tcgccagatc tagtgtgtgg     1512
ctgaacgttg aatgttagga tgctgctgtt tgttatgctc tgagtcttga gttcactttg     1572
ttaatttgca ccgtggatga gatgaataac ttgacgttgc aaaaaaaaaa aaaaaaa       1629

<210> SEQ ID NO 28
<211> LENGTH: 461
<212> TYPE: PRT
<213> ORGANISM: Zea mays

<400> SEQUENCE: 28
```

-continued

```
Met Pro Pro Ser Lys Ala Arg Arg Lys Arg Ser Leu Arg Asp Ile Thr
 1               5                  10                  15

Ala Thr Val Ala Thr Gly Thr Val Ala Asn Ser Lys Pro Gly Ser Ser
            20                  25                  30

Ser Thr Asn Glu Gly Lys Gln Gln Asp Lys Lys Lys Glu Gly Pro Gln
                35                  40                  45

Glu Pro Asp Ile Pro Pro Leu Pro Pro Val Val Asn Ile Val Pro
 50                  55                  60

Arg Gln Gly Leu Gly Cys Glu Val Val Glu Gly Leu Leu Val Pro Ser
 65                  70                  75                  80

Arg Lys Arg Glu Tyr Lys Pro Asn Ser Lys Tyr Thr Val Gly Asn His
                85                  90                  95

Pro Ile Tyr Ala Ile Gly Phe Asn Phe Ile Asp Met Arg Tyr Tyr Asp
                100                 105                 110

Val Phe Ala Ile Ala Ser Cys Asn Ser Val Ile Ile Tyr Arg Cys Leu
            115                 120                 125

Glu Asn Gly Gly Phe Gly Leu Leu Gln Asn Tyr Val Asp Glu Asp Lys
    130                 135                 140

Asp Glu Ser Phe Tyr Thr Leu Ser Trp Thr Ile Asp Gln Val Asp Ser
145                 150                 155                 160

Ser Pro Leu Leu Val Ala Ala Gly Ser Asn Arg Ile Ile Arg Val Ile
                165                 170                 175

Asn Cys Ala Thr Glu Lys Leu Asp Lys Ser Leu Val Gly His Gly Gly
            180                 185                 190

Ser Ile His Glu Ile Arg Thr His Ala Ser Lys Pro Ser Leu Ile Ile
        195                 200                 205

Ser Ala Ser Lys Asp Glu Ser Ile Arg Leu Trp Asn Val His Thr Gly
    210                 215                 220

Ile Cys Ile Leu Val Phe Ala Gly Ala Gly Gly His Arg His Asp Val
225                 230                 235                 240

Leu Ser Val Asp Phe His Pro Thr Glu Val Gly Ile Phe Ala Ser Cys
                245                 250                 255

Gly Met Asp Asn Thr Val Lys Ile Trp Ser Met Lys Glu Phe Trp Ile
            260                 265                 270

Tyr Val Glu Lys Ser Tyr Ser Trp Thr Gly His Pro Ser Lys Phe Pro
        275                 280                 285

Thr Arg Asn Ile Gln Phe Pro Val Leu Thr Ala Ala Val His Ser Asp
    290                 295                 300

Tyr Val Asp Cys Thr Arg Trp Leu Gly Asp Phe Ile Leu Ser Lys Ser
305                 310                 315                 320

Val Lys Asn Ala Val Leu Leu Trp Glu Pro Lys Pro Asp Lys Arg Arg
                325                 330                 335

Pro Gly Glu Gly Ser Val Asp Val Leu Gln Lys Tyr Pro Val Pro Lys
            340                 345                 350

Cys Ser Leu Trp Phe Met Lys Phe Ser Cys Asp Phe Tyr Ser Asn Gln
        355                 360                 365

Met Ala Ile Gly Asn Asn Lys Gly Glu Ile Tyr Val Trp Glu Val Gln
    370                 375                 380

Ser Ser Pro Pro Val Leu Ile Asp Arg Leu Cys Asn Gln Glu Cys Lys
385                 390                 395                 400

Ser Pro Ile Arg Gln Thr Ala Val Ser Phe Asp Gly Ser Thr Ile Leu
                405                 410                 415

Gly Ala Ala Asp Asp Gly Ala Ile Trp Arg Trp Asp Glu Val Asp Pro
```

```
                420             425             430
Ala Ala Ser Ser Ser Lys Pro Asp Gln Ala Ala Pro Ala Ala Gly
        435                 440                 445
Val Gly Ala Gly Ala Gly Ala Asp Ala Asp Ala Asp Ala
    450                 455                 460

<210> SEQ ID NO 29
<211> LENGTH: 1700
<212> TYPE: DNA
<213> ORGANISM: Zea mays
<220> FEATURE:
<221> NAME/KEY: CDS
<222> LOCATION: (394)...(1533)

<400> SEQUENCE: 29
gccgccgcga gcccgcgaca ctagtaacgg tctacaccac tagaatgact gaagaattga       60
attccagcaa attcaagctt ttgttttagc caagatttga gattcgattt gaagtgtgga      120
agtccttaca atttgccaat cctatatttg atctctgctg tgctgcgtta aatccctaaa      180
cttcacagcg cggcgccggc ccagccacgc cggaagaagt cgccgcgtga ggtcagtgtc      240
cccgttgctg ccgcctctaa cccgaagcct aggccgctgc cggtgcataa caaggagaat      300
caggcggagg ggaaagtagc agaggagggg gcagcaactg aggaggggga gaagtaccgg      360
gcggaaccgg aaatcttgcc gctgccgccg gcc atg gcg aag ctg ggc ccg ggg       414
                                    Met Ala Lys Leu Gly Pro Gly
                                      1               5 cag ggg ctc ggg tgc gag gcg gcg gag ggg tcg ctc gtg ccc agc cgg        462
Gln Gly Leu Gly Cys Glu Ala Ala Glu Gly Ser Leu Val Pro Ser Arg
         10                  15                  20 aag cgg gag tac aag ccc tgc ggc aag cac act gag ggg aag cgc ccg        510
Lys Arg Glu Tyr Lys Pro Cys Gly Lys His Thr Glu Gly Lys Arg Pro
     25                  30                  35 cta tat gct atc ggg ttc aac ttc atg gac gcg cgc tac tac gac gtc        558
Leu Tyr Ala Ile Gly Phe Asn Phe Met Asp Ala Arg Tyr Tyr Asp Val
 40                  45                  50                  55 ttc gcc acc gtc ggc ggc aac cgc gtg aca act tac cgc tgc ctt gag        606
Phe Ala Thr Val Gly Gly Asn Arg Val Thr Thr Tyr Arg Cys Leu Glu
                 60                  65                  70 aat ggt agt ttc gct ctt cta caa gct tac gtt gat gag gat aag gat        654
Asn Gly Ser Phe Ala Leu Leu Gln Ala Tyr Val Asp Glu Asp Lys Asp
             75                  80                  85 gag tcg ttc tat act cta agc tgg gct cgt gac cat gtt gat ggc tca        702
Glu Ser Phe Tyr Thr Leu Ser Trp Ala Arg Asp His Val Asp Gly Ser
         90                  95                 100 cca ctg ctg gtg gca gca gga agc aat ggg atc att cgg gtc atc aat        750
Pro Leu Leu Val Ala Ala Gly Ser Asn Gly Ile Ile Arg Val Ile Asn
    105                 110                 115 tgt gct aca gaa aag tta gct aag agc ttt gtt ggc cat ggc gac tca        798
Cys Ala Thr Glu Lys Leu Ala Lys Ser Phe Val Gly His Gly Asp Ser
120                 125                 130                 135 ata aat gag ata aga act caa ccg ttg aag cct tcg ctc atc att tct        846
Ile Asn Glu Ile Arg Thr Gln Pro Leu Lys Pro Ser Leu Ile Ile Ser
                140                 145                 150 gca agc aag gat gaa tct gtt agg cta tgg aat gtc cat aca ggg atc        894
Ala Ser Lys Asp Glu Ser Val Arg Leu Trp Asn Val His Thr Gly Ile
            155                 160                 165 tgt atc ttg ata ttt gct gga gct gga ggt cat cgc aat gaa gta ttg        942
Cys Ile Leu Ile Phe Ala Gly Ala Gly Gly His Arg Asn Glu Val Leu
        170                 175                 180
```

-continued

```
agt gtt gac ttc cat cct agt gat att gaa cgt ttt gca agt tgt ggc      990
Ser Val Asp Phe His Pro Ser Asp Ile Glu Arg Phe Ala Ser Cys Gly
    185                 190                 195 atg gac aac act gtg aaa atc tgg tca atg aaa gaa ttt tgg cta tat     1038
Met Asp Asn Thr Val Lys Ile Trp Ser Met Lys Glu Phe Trp Leu Tyr
200                 205                 210                 215 gtt gac aaa tca tat tca tgg act gac ctt cca tca aag ttt cca aca     1086
Val Asp Lys Ser Tyr Ser Trp Thr Asp Leu Pro Ser Lys Phe Pro Thr
                220                 225                 230 aaa tat gtc cag ttt cca gtc ttg att gct gca gta cac tct aac tat     1134
Lys Tyr Val Gln Phe Pro Val Leu Ile Ala Ala Val His Ser Asn Tyr
                    235                 240                 245 gtt gat tgt aca aga tgg ctt ggt gac ttc atc cta tca aag agt gtt     1182
Val Asp Cys Thr Arg Trp Leu Gly Asp Phe Ile Leu Ser Lys Ser Val
                250                 255                 260 gac aat gaa att gtg ctt tgg gaa ccg aag aca aaa gaa cag agt cct     1230
Asp Asn Glu Ile Val Leu Trp Glu Pro Lys Thr Lys Glu Gln Ser Pro
265                 270                 275 ggg gag gga agc atc gat atc ctt cag aag tat cct gtc cca gaa tgt     1278
Gly Glu Gly Ser Ile Asp Ile Leu Gln Lys Tyr Pro Val Pro Glu Cys
280                 285                 290                 295 gac att tgg ttt atc aaa ttt tca tgt gat ttt cac ttc aat cag ttg     1326
Asp Ile Trp Phe Ile Lys Phe Ser Cys Asp Phe His Phe Asn Gln Leu
                300                 305                 310 gcg ata ggc aac cgt gaa ggc aaa atc tac gtg tgg gaa gta cag tcc     1374
Ala Ile Gly Asn Arg Glu Gly Lys Ile Tyr Val Trp Glu Val Gln Ser
                315                 320                 325 agc cct cct gtc ctc att gct cgg ctg tat aat cag cag tgt aaa tcg     1422
Ser Pro Pro Val Leu Ile Ala Arg Leu Tyr Asn Gln Gln Cys Lys Ser
                330                 335                 340 ccg ata aga caa act gca gtg tcc ttc gat gga agc aca atc ctt gga     1470
Pro Ile Arg Gln Thr Ala Val Ser Phe Asp Gly Ser Thr Ile Leu Gly
345                 350                 355 gct ggt gaa gac ggc acc atc tgg cgg tgg gat gaa gtg gac cat ccg     1518
Ala Gly Glu Asp Gly Thr Ile Trp Arg Trp Asp Glu Val Asp His Pro
360                 365                 370                 375 agc tcc aga aac tga agaagtgttg ccgctcaatg ctggactgat ggttacgctc     1573
Ser Ser Arg Asn * ggttggggtt gcgatggttg aatccgttgg tggaaagtgc cacctggtgt tttttctagt   1633
caaaatggtt ggtgttaaca gaatattgaa tgcttcgaat gttgaaagtt gggaaaaaaa   1693
aaaaaaa                                                             1700

<210> SEQ ID NO 30
<211> LENGTH: 379
<212> TYPE: PRT
<213> ORGANISM: Zea mays

<400> SEQUENCE: 30

Met Ala Lys Leu Gly Pro Gly Gln Gly Leu Gly Cys Glu Ala Ala Glu
1               5                   10                  15

Gly Ser Leu Val Pro Ser Arg Lys Arg Glu Tyr Lys Pro Cys Gly Lys
                20                  25                  30

His Thr Glu Gly Lys Arg Pro Leu Tyr Ala Ile Gly Phe Asn Phe Met
            35                  40                  45

Asp Ala Arg Tyr Tyr Asp Val Phe Ala Thr Val Gly Gly Asn Arg Val
        50                  55                  60

Thr Thr Tyr Arg Cys Leu Glu Asn Gly Ser Phe Ala Leu Leu Gln Ala
65                  70                  75                  80
```

```
Tyr Val Asp Glu Asp Lys Asp Glu Ser Phe Tyr Thr Leu Ser Trp Ala
                 85                  90                  95

Arg Asp His Val Asp Gly Ser Pro Leu Leu Val Ala Ala Gly Ser Asn
            100                 105                 110

Gly Ile Ile Arg Val Ile Asn Cys Ala Thr Glu Lys Leu Ala Lys Ser
            115                 120                 125

Phe Val Gly His Gly Asp Ser Ile Asn Glu Ile Arg Thr Gln Pro Leu
            130                 135                 140

Lys Pro Ser Leu Ile Ile Ser Ala Ser Lys Asp Glu Ser Val Arg Leu
145                 150                 155                 160

Trp Asn Val His Thr Gly Ile Cys Ile Leu Ile Phe Ala Gly Ala Gly
                165                 170                 175

Gly His Arg Asn Glu Val Leu Ser Val Asp Phe His Pro Ser Asp Ile
                180                 185                 190

Glu Arg Phe Ala Ser Cys Gly Met Asp Asn Thr Val Lys Ile Trp Ser
            195                 200                 205

Met Lys Glu Phe Trp Leu Tyr Val Asp Lys Ser Tyr Ser Trp Thr Asp
210                 215                 220

Leu Pro Ser Lys Phe Pro Thr Lys Tyr Val Gln Phe Pro Val Leu Ile
225                 230                 235                 240

Ala Ala Val His Ser Asn Tyr Val Asp Cys Thr Arg Trp Leu Gly Asp
                245                 250                 255

Phe Ile Leu Ser Lys Ser Val Asp Asn Glu Ile Val Leu Trp Glu Pro
            260                 265                 270

Lys Thr Lys Glu Gln Ser Pro Gly Glu Gly Ser Ile Asp Ile Leu Gln
            275                 280                 285

Lys Tyr Pro Val Pro Glu Cys Asp Ile Trp Phe Ile Lys Phe Ser Cys
            290                 295                 300

Asp Phe His Phe Asn Gln Leu Ala Ile Gly Asn Arg Glu Gly Lys Ile
305                 310                 315                 320

Tyr Val Trp Glu Val Gln Ser Ser Pro Pro Val Leu Ile Ala Arg Leu
                325                 330                 335

Tyr Asn Gln Gln Cys Lys Ser Pro Ile Arg Gln Thr Ala Val Ser Phe
            340                 345                 350

Asp Gly Ser Thr Ile Leu Gly Ala Gly Glu Asp Gly Thr Ile Trp Arg
            355                 360                 365

Trp Asp Glu Val Asp His Pro Ser Ser Arg Asn
370                 375
```

<210> SEQ ID NO 31
<211> LENGTH: 595
<212> TYPE: DNA
<213> ORGANISM: Zea mays
<220> FEATURE:
<221> NAME/KEY: CDS
<222> LOCATION: (1)...(360)

<400> SEQUENCE: 31

```
cca cgc gtc cgc aat gaa att gtg ctt tgg gaa ccg aag aca aaa gaa      48
Pro Arg Val Arg Asn Glu Ile Val Leu Trp Glu Pro Lys Thr Lys Glu
1               5                   10                  15 cag agt cct ggg gag gga agc atc gat atc ctt cag aag tat cct gtc      96
Gln Ser Pro Gly Glu Gly Ser Ile Asp Ile Leu Gln Lys Tyr Pro Val
                20                  25                  30 cca gaa tgt gac att tgg ttt atc aaa ttt tca tgt gat ttt cac ttc     144
Pro Glu Cys Asp Ile Trp Phe Ile Lys Phe Ser Cys Asp Phe His Phe
```

```
                   35                  40                  45
aat cag ttg gcg ata ggc aac cgt gaa ggc aaa atc tac gtg tgg gaa        192
Asn Gln Leu Ala Ile Gly Asn Arg Glu Gly Lys Ile Tyr Val Trp Glu
     50                  55                  60 gta cag tcc agc cct cct gtc ctc att gct cgg ctg tat aat cag cag        240
Val Gln Ser Ser Pro Pro Val Leu Ile Ala Arg Leu Tyr Asn Gln Gln
 65                  70                  75                  80 tgt aaa tcg ccg ata aga caa act gca gtg tcc ttc gat gga agc aca        288
Cys Lys Ser Pro Ile Arg Gln Thr Ala Val Ser Phe Asp Gly Ser Thr
                 85                  90                  95 atc ctt gga gct ggt gaa gac ggc acc atc tgg cgg tgg gat gaa gtg        336
Ile Leu Gly Ala Gly Glu Asp Gly Thr Ile Trp Arg Trp Asp Glu Val
            100                 105                 110 gac cat ccg agc tcc aga aac tga agaagtgttg ccgctcaatg ctggactgat       390
Asp His Pro Ser Ser Arg Asn *
        115 ggttacgctc ggttggggtt gcgatggttg aatccgttgg tggaaagtgc cacctggtgt      450 tttttctagt caaaatggtt ggtgttaaca gaatattgaa tgcttcgaat gttgaaagtt      510 gggatgcttg tgctggtaaa aaaaaaaaaa aaaaaaaaaa aaaaaaaaaa aaaaaaaaaa      570 aaaaaaaaaa aaaaaaaaaa aaaag                                           595

<210> SEQ ID NO 32
<211> LENGTH: 119
<212> TYPE: PRT
<213> ORGANISM: Zea mays

<400> SEQUENCE: 32

Pro Arg Val Arg Asn Glu Ile Val Leu Trp Glu Pro Lys Thr Lys Glu
 1               5                  10                  15

Gln Ser Pro Gly Glu Gly Ser Ile Asp Ile Leu Gln Lys Tyr Pro Val
            20                  25                  30

Pro Glu Cys Asp Ile Trp Phe Ile Lys Phe Ser Cys Asp Phe His Phe
        35                  40                  45

Asn Gln Leu Ala Ile Gly Asn Arg Glu Gly Lys Ile Tyr Val Trp Glu
     50                  55                  60

Val Gln Ser Ser Pro Pro Val Leu Ile Ala Arg Leu Tyr Asn Gln Gln
 65                  70                  75                  80

Cys Lys Ser Pro Ile Arg Gln Thr Ala Val Ser Phe Asp Gly Ser Thr
                 85                  90                  95

Ile Leu Gly Ala Gly Glu Asp Gly Thr Ile Trp Arg Trp Asp Glu Val
            100                 105                 110

Asp His Pro Ser Ser Arg Asn
        115

<210> SEQ ID NO 33
<211> LENGTH: 1498
<212> TYPE: DNA
<213> ORGANISM: Oryza sativa
<220> FEATURE:
<221> NAME/KEY: CDS
<222> LOCATION: (3)...(1130)
<220> FEATURE:
<221> NAME/KEY: misc_feature
<222> LOCATION: (839)...(839)
<223> OTHER INFORMATION: n = A, T, C or G

<400> SEQUENCE: 33 cg tcc tcc ttc ttc cac cgc atc gtc gct cgc cgt tat gaa ctt            47
   Ser Ser Phe Phe His Arg Ile Val Ala Arg Arg Arg Tyr Glu Leu
```

```
                1               5                   10                  15
cca aat ttg gtt cca agc agg aag agg gag tac aag gcg tgc aac aag         95
Pro Asn Leu Val Pro Ser Arg Lys Arg Glu Tyr Lys Ala Cys Asn Lys
                        20                  25                  30 ctc acc gag ggg aag cgg cag ctc tac gcc atc gga ttc aac ttc ctc         143
Leu Thr Glu Gly Lys Arg Gln Leu Tyr Ala Ile Gly Phe Asn Phe Leu
                35                  40                  45 gac ttc cac tac tac gag gtc ttc gcc acc gtc ggc ggc aac cgc gtg         191
Asp Phe His Tyr Tyr Glu Val Phe Ala Thr Val Gly Gly Asn Arg Val
            50                  55                  60 aca acc tac agc tgc ctc aag gat ggt aat ttt gct atc ctg caa gca         239
Thr Thr Tyr Ser Cys Leu Lys Asp Gly Asn Phe Ala Ile Leu Gln Ala
        65                  70                  75 tat att gat gag gat aag gat gaa tcg ttc tac aca ctg agt tgg gct         287
Tyr Ile Asp Glu Asp Lys Asp Glu Ser Phe Tyr Thr Leu Ser Trp Ala
80                  85                  90                  95 tgt gat ctt gat ggc aca ccg ctg tta gtg gct gca gga agc aat ggg         335
Cys Asp Leu Asp Gly Thr Pro Leu Leu Val Ala Ala Gly Ser Asn Gly
                        100                 105                 110 atc att cgg gtc atc aac tgt gcc act gag aag tta ctc aag act ttt         383
Ile Ile Arg Val Ile Asn Cys Ala Thr Glu Lys Leu Leu Lys Thr Phe
                115                 120                 125 gtt ggc cat ggc gat tca ata aac gag ata aga act caa gca tta aag         431
Val Gly His Gly Asp Ser Ile Asn Glu Ile Arg Thr Gln Ala Leu Lys
            130                 135                 140 cct tcg ctc atc att tct gca agc aag gat gaa tct gtt agg ctg tgg        479
Pro Ser Leu Ile Ile Ser Ala Ser Lys Asp Glu Ser Val Arg Leu Trp
        145                 150                 155 aat gtt cac aca ggg atc tgc att ttg att ttt gct gga gca gga ggt         527
Asn Val His Thr Gly Ile Cys Ile Leu Ile Phe Ala Gly Ala Gly Gly
160                 165                 170                 175 cac cgg aat gaa gta ttg agt gtt gac ttc cac cca tct gat atc tac         575
His Arg Asn Glu Val Leu Ser Val Asp Phe His Pro Ser Asp Ile Tyr
                        180                 185                 190 cgc ata gca agt tgt ggc atg gat aac act gtt aaa ata tgg tca atg         623
Arg Ile Ala Ser Cys Gly Met Asp Asn Thr Val Lys Ile Trp Ser Met
                195                 200                 205 aag gaa ttc tgg cca tat gtt gag caa tcc ttt aca tgg act gac ctt         671
Lys Glu Phe Trp Pro Tyr Val Glu Gln Ser Phe Thr Trp Thr Asp Leu
                210                 215                 220 cca tca aaa ttt cca aca aaa tat gtg caa ttt ccg gtc ttg gtt gct         719
Pro Ser Lys Phe Pro Thr Lys Tyr Val Gln Phe Pro Val Leu Val Ala
        225                 230                 235 gta gta cat tct aac tat gtt gat tgt act aga tgg ctt ggt gac ttc         767
Val Val His Ser Asn Tyr Val Asp Cys Thr Arg Trp Leu Gly Asp Phe
240                 245                 250                 255 att ctg tca aag agt gtt gac aat gaa att gtg ctg tgg gag cca aaa         815
Ile Leu Ser Lys Ser Val Asp Asn Glu Ile Val Leu Trp Glu Pro Lys
                        260                 265                 270 aca aaa gaa caa agt ccc ggg gan ggt agc att gat att ctt cag aag         863
Thr Lys Glu Gln Ser Pro Gly Xaa Gly Ser Ile Asp Ile Leu Gln Lys
                275                 280                 285 tat cct gtg cca gaa tgt gat atc tgg ttt atc aaa ttc tca tgc gat         911
Tyr Pro Val Pro Glu Cys Asp Ile Trp Phe Ile Lys Phe Ser Cys Asp
        290                 295                 300 ttt cac ttc aat caa ttg gca ata ggc aac cgt gaa gga aaa gtc ttt         959
Phe His Phe Asn Gln Leu Ala Ile Gly Asn Arg Glu Gly Lys Val Phe
305                 310                 315 gtc tgg gaa gta cag tcc agt cct cct gtt tta act gct cgg ctg act         1007
```

```
Val Trp Glu Val Gln Ser Ser Pro Val Leu Thr Ala Arg Leu Thr
320                 325                 330                 335 aat ccg caa tgc aaa tct gcg ata agg cag act gcc gtg tca ttt gat    1055
Asn Pro Gln Cys Lys Ser Ala Ile Arg Gln Thr Ala Val Ser Phe Asp
            340                 345                 350 gga agc aca atc ctt gcc tgc agc gag gat ggc agc ata tgg cga tgg    1103
Gly Ser Thr Ile Leu Ala Cys Ser Glu Asp Gly Ser Ile Trp Arg Trp
        355                 360                 365 gat gaa gtg gac cat cca aaa gca tga aaagtaccct tatagacaga          1150
Asp Glu Val Asp His Pro Lys Ala *
        370                 375 ccatggcaat gccagattaa gattgacttg ggaattcctg catgtgtact ttgttgtggg  1210
ggttatagta atcagtctta ctgttgaaaa aaagtgcaat ctgatactct gaaattagaa  1270
ggattgacag ctgaatgctg gggttaccaa cttgaatgtt gcaaatagga tactgcttct  1330
gttatatgct gaatgtttca agttagggcc tttttgtaaa tgggaagatt cggctatgcc  1390
agatttttgg aaaagttgcc atttgctttg ttaccaaagt tgcatggcaa agattggccc  1450
agctcaaatt tctatagtta taaatgagtt gccaaatatt ttggcttc              1498
```

<210> SEQ ID NO 34
<211> LENGTH: 375
<212> TYPE: PRT
<213> ORGANISM: Oryza sativa
<220> FEATURE:
<221> NAME/KEY: VARIANT
<222> LOCATION: (279)...(279)
<223> OTHER INFORMATION: Xaa = Any Amino Acid

<400> SEQUENCE: 34

```
Ser Ser Phe Phe His Arg Ile Val Ala Arg Arg Tyr Glu Leu Pro
1               5                   10                  15

Asn Leu Val Pro Ser Arg Lys Arg Glu Tyr Lys Ala Cys Asn Lys Leu
                20                  25                  30

Thr Glu Gly Lys Arg Gln Leu Tyr Ala Ile Gly Phe Asn Phe Leu Asp
            35                  40                  45

Phe His Tyr Tyr Glu Val Phe Ala Thr Val Gly Gly Asn Arg Val Thr
    50                  55                  60

Thr Tyr Ser Cys Leu Lys Asp Gly Asn Phe Ala Ile Leu Gln Ala Tyr
65                  70                  75                  80

Ile Asp Glu Asp Lys Asp Glu Ser Phe Tyr Thr Leu Ser Trp Ala Cys
                85                  90                  95

Asp Leu Asp Gly Thr Pro Leu Leu Val Ala Ala Gly Ser Asn Gly Ile
            100                 105                 110

Ile Arg Val Ile Asn Cys Ala Thr Glu Lys Leu Leu Lys Thr Phe Val
        115                 120                 125

Gly His Gly Asp Ser Ile Asn Glu Ile Arg Thr Gln Ala Leu Lys Pro
    130                 135                 140

Ser Leu Ile Ile Ser Ala Ser Lys Asp Glu Ser Val Arg Leu Trp Asn
145                 150                 155                 160

Val His Thr Gly Ile Cys Ile Leu Ile Phe Ala Gly Ala Gly Gly His
                165                 170                 175

Arg Asn Glu Val Leu Ser Val Asp Phe His Pro Ser Asp Ile Tyr Arg
            180                 185                 190

Ile Ala Ser Cys Gly Met Asp Asn Thr Val Lys Ile Trp Ser Met Lys
        195                 200                 205

Glu Phe Trp Pro Tyr Val Glu Gln Ser Phe Thr Trp Thr Asp Leu Pro
```

```
                   210                 215                 220
Ser Lys Phe Pro Thr Lys Tyr Val Gln Phe Pro Val Leu Val Ala Val
225                 230                 235                 240

Val His Ser Asn Tyr Val Asp Cys Thr Arg Trp Leu Gly Asp Phe Ile
                245                 250                 255

Leu Ser Lys Ser Val Asp Asn Glu Ile Val Leu Trp Glu Pro Lys Thr
            260                 265                 270

Lys Glu Gln Ser Pro Gly Xaa Gly Ser Ile Asp Ile Leu Gln Lys Tyr
        275                 280                 285

Pro Val Pro Glu Cys Asp Ile Trp Phe Ile Lys Phe Ser Cys Asp Phe
290                 295                 300

His Phe Asn Gln Leu Ala Ile Gly Asn Arg Glu Gly Lys Val Phe Val
305                 310                 315                 320

Trp Glu Val Gln Ser Ser Pro Pro Val Leu Thr Ala Arg Leu Thr Asn
                325                 330                 335

Pro Gln Cys Lys Ser Ala Ile Arg Gln Thr Ala Val Ser Phe Asp Gly
            340                 345                 350

Ser Thr Ile Leu Ala Cys Ser Glu Asp Gly Ser Ile Trp Arg Trp Asp
        355                 360                 365

Glu Val Asp His Pro Lys Ala
    370                 375

<210> SEQ ID NO 35
<211> LENGTH: 1387
<212> TYPE: DNA
<213> ORGANISM: Glycine max
<220> FEATURE:
<221> NAME/KEY: CDS
<222> LOCATION: (25)...(1188)
<220> FEATURE:
<221> NAME/KEY: misc_feature
<222> LOCATION: (14)...(14)
<223> OTHER INFORMATION: n = A, T, C or G

<400> SEQUENCE: 35
gggaagcgaa cagnagaaga gtag atg gtg ggt gaa acg gcg gca acg ggg      51
                        Met Val Gly Glu Thr Ala Ala Thr Gly
                         1               5 aag tcg gtt ggt ttg ggt ttg gga tgt gac cca gtg gtg gga tcc ttg     99
Lys Ser Val Gly Leu Gly Leu Gly Cys Asp Pro Val Val Gly Ser Leu
 10              15                  20                  25 gct tgt tcg aag aag aga gaa tac aga gtc acc aat cgc ctt caa gag   147
Ala Cys Ser Lys Lys Arg Glu Tyr Arg Val Thr Asn Arg Leu Gln Glu
            30                  35                  40 gga aag cgc cct cta tac gcc gtc att ttc aac ttc atc gac tcc cgc   195
Gly Lys Arg Pro Leu Tyr Ala Val Ile Phe Asn Phe Ile Asp Ser Arg
        45                  50                  55 tac ttc aac gtt ttc gcc act gtt ggc ggc aat agg gtt act gtt tat   243
Tyr Phe Asn Val Phe Ala Thr Val Gly Gly Asn Arg Val Thr Val Tyr
    60                  65                  70 caa tgc ctt gat gaa ggg gat att gct gtt ttg caa tct tat gcg gat   291
Gln Cys Leu Asp Glu Gly Asp Ile Ala Val Leu Gln Ser Tyr Ala Asp
75                  80                  85 gag gat aag aat gag tct ttt tac acc gtg ggt tgg gca tgc aat gtt   339
Glu Asp Lys Asn Glu Ser Phe Tyr Thr Val Gly Trp Ala Cys Asn Val
 90                  95                 100                 105 gac ggg acc cca ctt gtt gtg gct gga gga ctc aat ggg gta atc cga   387
Asp Gly Thr Pro Leu Val Val Ala Gly Gly Leu Asn Gly Val Ile Arg
            110                 115                 120
```

```
gtc att gat gct ggc agt gag aag ata cat aag agt ttt gtt ggc cat     435
Val Ile Asp Ala Gly Ser Glu Lys Ile His Lys Ser Phe Val Gly His
            125                 130                 135 gga gac tcc ata aat gaa gtc aaa gct caa ata tta aat cca tca ctc     483
Gly Asp Ser Ile Asn Glu Val Lys Ala Gln Ile Leu Asn Pro Ser Leu
        140                 145                 150 gtg gta tcg gca agc aaa gat gaa tct att cgg tta tgg aat gct cat     531
Val Val Ser Ala Ser Lys Asp Glu Ser Ile Arg Leu Trp Asn Ala His
    155                 160                 165 act gga ata tgc att ttg ata ttt gct gga ggc ggg gga cat cgt aat     579
Thr Gly Ile Cys Ile Leu Ile Phe Ala Gly Gly Gly His Arg Asn
170                 175                 180                 185 gaa gtc tta agt gtt gat ttt cat cca tcg gat atg tat cgt att tgt     627
Glu Val Leu Ser Val Asp Phe His Pro Ser Asp Met Tyr Arg Ile Cys
                190                 195                 200 agt tgt ggc atg gat agt act gta aaa ata tgg tct atg aag gag ttc     675
Ser Cys Gly Met Asp Ser Thr Val Lys Ile Trp Ser Met Lys Glu Phe
            205                 210                 215 tgg aca tat gta gaa aaa tca tcc aca tgg aca gat ctt cct tcc aag     723
Trp Thr Tyr Val Glu Lys Ser Ser Thr Trp Thr Asp Leu Pro Ser Lys
        220                 225                 230 ttt cca aca aaa ttt gtc cag ttt cct gtt tac act gct tca gtg cat     771
Phe Pro Thr Lys Phe Val Gln Phe Pro Val Tyr Thr Ala Ser Val His
    235                 240                 245 ata aat tat gtt gac tgt aat agg tgg ttg ggt gat ttt atc ctc tca     819
Ile Asn Tyr Val Asp Cys Asn Arg Trp Leu Gly Asp Phe Ile Leu Ser
250                 255                 260                 265 aag agt gtt gat aat gaa att atc ttg tgg gaa cct aaa gtg aac gaa     867
Lys Ser Val Asp Asn Glu Ile Ile Leu Trp Glu Pro Lys Val Asn Glu
                270                 275                 280 caa act cca ggg aag ggt gta gtt gat gtt ctt cat aaa tac cct att     915
Gln Thr Pro Gly Lys Gly Val Val Asp Val Leu His Lys Tyr Pro Ile
            285                 290                 295 ccc gat tgc aat atc tgg ttc atc aag ttt tct tgt gac ttc cat ttc     963
Pro Asp Cys Asn Ile Trp Phe Ile Lys Phe Ser Cys Asp Phe His Phe
        300                 305                 310 aac ata gtt aca gtg ggt aac agg gaa ggg aag att ttt gtt tgg gaa    1011
Asn Ile Val Thr Val Gly Asn Arg Glu Gly Lys Ile Phe Val Trp Glu
    315                 320                 325 tta cag tca agt cct ccc gta ctt gct gca aag ttg tca cat cct caa    1059
Leu Gln Ser Ser Pro Pro Val Leu Ala Ala Lys Leu Ser His Pro Gln
330                 335                 340                 345 tca aaa tcc cca atc agg cag act gca aca tcc ttt gat gga agt act    1107
Ser Lys Ser Pro Ile Arg Gln Thr Ala Thr Ser Phe Asp Gly Ser Thr
                350                 355                 360 ata ttg agt tgc tgt gag gat ggg aca ata tgg cgt tgg gat gtt tca    1155
Ile Leu Ser Cys Cys Glu Asp Gly Thr Ile Trp Arg Trp Asp Val Ser
            365                 370                 375 aaa ccc tca acc tca acc tca acc gca gcc taa cttatcttcg tgcaacacca  1208
Lys Pro Ser Thr Ser Thr Ser Thr Ala Ala  *
        380                 385 atctgatgtg catgtcaaac acaagggcat ttgtgattta tcaatttaac cagtcatgta  1268
catcaggaac ttgatttatt gcatgttttt gtatttgttt attttggttc ggtaaggctt  1328
ataatgtaaa atgttcaact aagaactcag ttaaaagtta tttaaataaa gtaaagcca   1387

<210> SEQ ID NO 36
<211> LENGTH: 387
<212> TYPE: PRT
<213> ORGANISM: Glycine max
```

<400> SEQUENCE: 36

```
Met Val Gly Glu Thr Ala Ala Thr Gly Lys Ser Val Gly Leu Gly Leu
 1               5                  10                  15
Gly Cys Asp Pro Val Val Gly Ser Leu Ala Cys Ser Lys Lys Arg Glu
                20                  25                  30
Tyr Arg Val Thr Asn Arg Leu Gln Glu Gly Lys Arg Pro Leu Tyr Ala
            35                  40                  45
Val Ile Phe Asn Phe Ile Asp Ser Arg Tyr Phe Asn Val Phe Ala Thr
50                  55                  60
Val Gly Gly Asn Arg Val Thr Val Tyr Gln Cys Leu Asp Glu Gly Asp
65                  70                  75                  80
Ile Ala Val Leu Gln Ser Tyr Ala Asp Glu Asp Lys Asn Glu Ser Phe
                85                  90                  95
Tyr Thr Val Gly Trp Ala Cys Asn Val Asp Gly Thr Pro Leu Val Val
                100                 105                 110
Ala Gly Gly Leu Asn Gly Val Ile Arg Val Ile Asp Ala Gly Ser Glu
            115                 120                 125
Lys Ile His Lys Ser Phe Val Gly His Gly Asp Ser Ile Asn Glu Val
130                 135                 140
Lys Ala Gln Ile Leu Asn Pro Ser Leu Val Val Ser Ala Ser Lys Asp
145                 150                 155                 160
Glu Ser Ile Arg Leu Trp Asn Ala His Thr Gly Ile Cys Ile Leu Ile
                165                 170                 175
Phe Ala Gly Gly Gly His Arg Asn Glu Val Leu Ser Val Asp Phe
                180                 185                 190
His Pro Ser Asp Met Tyr Arg Ile Cys Ser Cys Gly Met Asp Ser Thr
            195                 200                 205
Val Lys Ile Trp Ser Met Lys Glu Phe Trp Thr Tyr Val Glu Lys Ser
210                 215                 220
Ser Thr Trp Thr Asp Leu Pro Ser Lys Phe Pro Thr Lys Phe Val Gln
225                 230                 235                 240
Phe Pro Val Tyr Thr Ala Ser Val His Ile Asn Tyr Val Asp Cys Asn
                245                 250                 255
Arg Trp Leu Gly Asp Phe Ile Leu Ser Lys Ser Val Asp Asn Glu Ile
            260                 265                 270
Ile Leu Trp Glu Pro Lys Val Asn Glu Gln Thr Pro Gly Lys Gly Val
        275                 280                 285
Val Asp Val Leu His Lys Tyr Pro Ile Pro Asp Cys Asn Ile Trp Phe
290                 295                 300
Ile Lys Phe Ser Cys Asp Phe His Phe Asn Ile Val Thr Val Gly Asn
305                 310                 315                 320
Arg Glu Gly Lys Ile Phe Val Trp Glu Leu Gln Ser Ser Pro Pro Val
                325                 330                 335
Leu Ala Ala Lys Leu Ser His Pro Gln Ser Lys Ser Pro Ile Arg Gln
            340                 345                 350
Thr Ala Thr Ser Phe Asp Gly Ser Thr Ile Leu Ser Cys Cys Glu Asp
                355                 360                 365
Gly Thr Ile Trp Arg Trp Asp Val Ser Lys Pro Ser Thr Ser Thr Ser
            370                 375                 380
Thr Ala Ala
385
```

-continued

```
<210> SEQ ID NO 37
<211> LENGTH: 1518
<212> TYPE: DNA
<213> ORGANISM: Triticum aestivum
<220> FEATURE:
<221> NAME/KEY: CDS
<222> LOCATION: (88)...(1224)

<400> SEQUENCE: 37
gcgtctgcaa aggcggbggc gctgctccaa ggcgtgggcc gagaggagga gaagcaggcg      60
ccagagcccc aacctctccc ggcgcgc atg gcg agg ctg ggc ccg ggg cag ggg     114
                               Met Ala Arg Leu Gly Pro Gly Gln Gly
                                 1               5 tta ggg tgc gag gcg gcg gtg ggg tcg ctg gcg ccc agc cgg agc cgg       162
Leu Gly Cys Glu Ala Ala Val Gly Ser Leu Ala Pro Ser Arg Ser Arg
 10              15                  20                  25 gag tac aag ctc tgc agc aag cac acc gag ggc aag cgc ccg ctc tac       210
Glu Tyr Lys Leu Cys Ser Lys His Thr Glu Gly Lys Arg Pro Leu Tyr
             30                  35                  40 gcc atc ggc ttc aac ttc atc gac gcc cgc tac tac gac gtc ttc gcc       258
Ala Ile Gly Phe Asn Phe Ile Asp Ala Arg Tyr Tyr Asp Val Phe Ala
         45                  50                  55 acc gtc ggc ggc aat cgt gtg acg acg tac cgt ggc ctc ccc gac ggt       306
Thr Val Gly Gly Asn Arg Val Thr Thr Tyr Arg Gly Leu Pro Asp Gly
     60                  65                  70 aac ttg gct gtt ctg caa gca tac att gat gcg gac gat gct cag tca       354
Asn Leu Ala Val Leu Gln Ala Tyr Ile Asp Ala Asp Asp Ala Gln Ser
 75                  80                  85 ttc tac act ctg agc tgg gct tgt gac ctt gac ggc aca cca ctg cta       402
Phe Tyr Thr Leu Ser Trp Ala Cys Asp Leu Asp Gly Thr Pro Leu Leu
 90                  95                 100                 105 gtg gca gca gga agc aat gcg gtc att cgg gtc atc aac tgt gcc acc       450
Val Ala Ala Gly Ser Asn Ala Val Ile Arg Val Ile Asn Cys Ala Thr
             110                 115                 120 gag aag ttg ttt aag agt ttt ctt ggc cat ggt gat tca ata aat gag       498
Glu Lys Leu Phe Lys Ser Phe Leu Gly His Gly Asp Ser Ile Asn Glu
         125                 130                 135 ata aga act caa cca ttg aag cct tcg ctc ttc att tct gca agc aag       546
Ile Arg Thr Gln Pro Leu Lys Pro Ser Leu Phe Ile Ser Ala Ser Lys
     140                 145                 150 gac gag tct gtt agg cta tgg aat gtc cat aca ggt atc tgc atc ttg       594
Asp Glu Ser Val Arg Leu Trp Asn Val His Thr Gly Ile Cys Ile Leu
 155                 160                 165 att ttt gct gga gga gga ggt cac cgt aat gaa gta ttg agt gtt gac       642
Ile Phe Ala Gly Gly Gly Gly His Arg Asn Glu Val Leu Ser Val Asp
170                 175                 180                 185 ttc cac cct tct gat atc tac cga att gcc agt tgt ggc atg gat aat       690
Phe His Pro Ser Asp Ile Tyr Arg Ile Ala Ser Cys Gly Met Asp Asn
             190                 195                 200 act gtt aaa atc tgg tca atg aaa gaa ttt tgg cca tac gtg gag aaa       738
Thr Val Lys Ile Trp Ser Met Lys Glu Phe Trp Pro Tyr Val Glu Lys
         205                 210                 215 tcc ttt aca tgg act gac ctt cca tca aaa ttt cca acg aaa ttt gtt       786
Ser Phe Thr Trp Thr Asp Leu Pro Ser Lys Phe Pro Thr Lys Phe Val
     220                 225                 230 caa ttt ccg ctc atg act tcc gtg gtt cat tct aac tat gtt gac tgt       834
Gln Phe Pro Leu Met Thr Ser Val Val His Ser Asn Tyr Val Asp Cys
 235                 240                 245 act agg tgg ctt ggt gac ttc atc ctg tcg aag agt gtt gac aat gaa       882
Thr Arg Trp Leu Gly Asp Phe Ile Leu Ser Lys Ser Val Asp Asn Glu
250                 255                 260                 265
```

-continued

```
att gtt ctg tgg gag cca aaa ata aaa gag cag ggt ccc ggc gag ggt      930
Ile Val Leu Trp Glu Pro Lys Ile Lys Glu Gln Gly Pro Gly Glu Gly
            270                 275                 280 agc att gat gtt ctt cag aag tac cct gtg cct gat tgt gac att tgg      978
Ser Ile Asp Val Leu Gln Lys Tyr Pro Val Pro Asp Cys Asp Ile Trp
        285                 290                 295 ttt atc aaa ttc tca tgt gat ttt cac ttc aat caa tta gca ata ggc     1026
Phe Ile Lys Phe Ser Cys Asp Phe His Phe Asn Gln Leu Ala Ile Gly
    300                 305                 310 aac cgc gaa ggc aaa atc tat gtg tgg gaa gtg cag gcg agc cct cct     1074
Asn Arg Glu Gly Lys Ile Tyr Val Trp Glu Val Gln Ala Ser Pro Pro
315                 320                 325 gtg cta att acc cgg ctg agt agt cca caa tgc aaa atg cca ata agg     1122
Val Leu Ile Thr Arg Leu Ser Ser Pro Gln Cys Lys Met Pro Ile Arg
        330                 335                 340             345 cag act gca gtg tcg ttt gat gga agc acg atc ctt gcc tgc ggc gag     1170
Gln Thr Ala Val Ser Phe Asp Gly Ser Thr Ile Leu Ala Cys Gly Glu
            350                 355                 360 gat ggc agc ata tac cgc tgg gat gaa gtg gaa cat caa gct gca aaa     1218
Asp Gly Ser Ile Tyr Arg Trp Asp Glu Val Glu His Gln Ala Ala Lys
                365                 370                 375 aat tga agcaactgaa aaccaccatc cgtgcggccc catggcaatg ccagccagtt      1274
Asn *
tgagcttgtc ctgggtagtt gttgtgttgc ttacttagtg ggttgtacca attacttagt   1334
ccagaagttg gggtgaatga gcttataatg ttgtaaggtt ggatgttgtt gattcgatga   1394
tttgccggat gtttctgttt attacattgg ctgtatcatg taccgaatgt gggagttaaa   1454
cttaaatcct cgttcgcatt ctaaaaaaaa aaaaaaaaaa aaaaaaaaaa aaaaaaaaaa   1514
aaaa                                                                1518

<210> SEQ ID NO 38
<211> LENGTH: 378
<212> TYPE: PRT
<213> ORGANISM: Triticum aestivum

<400> SEQUENCE: 38

Met Ala Arg Leu Gly Pro Gly Gln Gly Leu Gly Cys Glu Ala Ala Val
1               5                   10                  15

Gly Ser Leu Ala Pro Ser Arg Ser Arg Glu Tyr Lys Leu Cys Ser Lys
            20                  25                  30

His Thr Glu Gly Lys Arg Pro Leu Tyr Ala Ile Gly Phe Asn Phe Ile
        35                  40                  45

Asp Ala Arg Tyr Tyr Asp Val Phe Ala Thr Val Gly Gly Asn Arg Val
    50                  55                  60

Thr Thr Tyr Arg Gly Leu Pro Asp Gly Asn Leu Ala Val Leu Gln Ala
65                  70                  75                  80

Tyr Ile Asp Ala Asp Ala Gln Ser Phe Tyr Thr Leu Ser Trp Ala
                85                  90                  95

Cys Asp Leu Asp Gly Thr Pro Leu Leu Val Ala Ala Gly Ser Asn Ala
            100                 105                 110

Val Ile Arg Val Ile Asn Cys Ala Thr Glu Lys Leu Phe Lys Ser Phe
        115                 120                 125

Leu Gly His Gly Asp Ser Ile Asn Glu Ile Arg Thr Gln Pro Leu Lys
    130                 135                 140

Pro Ser Leu Phe Ile Ser Ala Ser Lys Asp Glu Ser Val Arg Leu Trp
145                 150                 155                 160
```

-continued

```
Asn Val His Thr Gly Ile Cys Ile Leu Ile Phe Ala Gly Gly Gly Gly
            165                 170                 175

His Arg Asn Glu Val Leu Ser Val Asp Phe His Pro Ser Asp Ile Tyr
        180                 185                 190

Arg Ile Ala Ser Cys Gly Met Asp Asn Thr Val Lys Ile Trp Ser Met
    195                 200                 205

Lys Glu Phe Trp Pro Tyr Val Glu Lys Ser Phe Thr Trp Thr Asp Leu
210                 215                 220

Pro Ser Lys Phe Pro Thr Lys Phe Val Gln Phe Pro Leu Met Thr Ser
225                 230                 235                 240

Val Val His Ser Asn Tyr Val Asp Cys Thr Arg Trp Leu Gly Asp Phe
                245                 250                 255

Ile Leu Ser Lys Ser Val Asp Asn Glu Ile Val Leu Trp Glu Pro Lys
            260                 265                 270

Ile Lys Glu Gln Gly Pro Gly Glu Gly Ser Ile Asp Val Leu Gln Lys
        275                 280                 285

Tyr Pro Val Pro Asp Cys Asp Ile Trp Phe Ile Lys Phe Ser Cys Asp
    290                 295                 300

Phe His Phe Asn Gln Leu Ala Ile Gly Asn Arg Glu Gly Lys Ile Tyr
305                 310                 315                 320

Val Trp Glu Val Gln Ala Ser Pro Pro Val Leu Ile Thr Arg Leu Ser
                325                 330                 335

Ser Pro Gln Cys Lys Met Pro Ile Arg Gln Thr Ala Val Ser Phe Asp
            340                 345                 350

Gly Ser Thr Ile Leu Ala Cys Gly Glu Asp Gly Ser Ile Tyr Arg Trp
        355                 360                 365

Asp Glu Val Glu His Gln Ala Ala Lys Asn
    370                 375
```

```
<210> SEQ ID NO 39
<211> LENGTH: 488
<212> TYPE: DNA
<213> ORGANISM: Zea mays
<220> FEATURE:
<221> NAME/KEY: CDS
<222> LOCATION: (212)...(397)
<220> FEATURE:
<221> NAME/KEY: misc_feature
<222> LOCATION: 464, 475, 488
<223> OTHER INFORMATION: n = A, T, C or G

<400> SEQUENCE: 39
gccggaagaa gtcgccgcgt gaggtcagtg tccccgttgc tgccgcctct aacccgaagc    60
ctaggccgct gccggtgcat aacaaggaga atcaggcgga ggggaaagta gcagaggagg   120
gggcagcaac tgaggagggg gagaagtacc gggcggaacc ggaaatcttg ccgctgccgc   180
cggccatggc gaactgggcc cggggcaggg g ctc ggg tgc gag gcg gcg gag       232
                                  Leu Gly Cys Glu Ala Ala Glu
                                   1               5 ggg tcg ctc gtg ccc agc cgg aag cgg gag tac aag ccc tgc ggc aag    280
Gly Ser Leu Val Pro Ser Arg Lys Arg Glu Tyr Lys Pro Cys Gly Lys
            10                  15                  20 cac act gag ggg aag cgc ccg cta tat gct atc ggg ttc aac ttc atg    328
His Thr Glu Gly Lys Arg Pro Leu Tyr Ala Ile Gly Phe Asn Phe Met
        25                  30                  35 gac gcg cgc tac tac gac gtc ttc gcc acc gtc ggc ggc aac cgc gtg    376
Asp Ala Arg Tyr Tyr Asp Val Phe Ala Thr Val Gly Gly Asn Arg Val
40                  45                  50                  55
```

| | | |
|---|---|---|
| aac aac tta ccg ctg cct tga gaatggtagt ttcgctcttc tacaagctta | | 427 |
| Asn Asn Leu Pro Leu Pro * | | |
| 60 | | |
| | | |
| cgttgatgag gataaggatg agtcgttcta tactccnaag ctgggccntt gaccatgttg | | 487 |
| | | |
| n | | 488 |

<210> SEQ ID NO 40
<211> LENGTH: 61
<212> TYPE: PRT
<213> ORGANISM: Zea mays

<400> SEQUENCE: 40

Leu Gly Cys Glu Ala Ala Glu Gly Ser Leu Val Pro Ser Arg Lys Arg
1               5                   10                  15

Glu Tyr Lys Pro Cys Gly Lys His Thr Glu Gly Lys Arg Pro Leu Tyr
            20                  25                  30

Ala Ile Gly Phe Asn Phe Met Asp Ala Arg Tyr Tyr Asp Val Phe Ala
        35                  40                  45

Thr Val Gly Gly Asn Arg Val Asn Asn Leu Pro Leu Pro
    50                  55                  60

<210> SEQ ID NO 41
<211> LENGTH: 348
<212> TYPE: DNA
<213> ORGANISM: Zea mays
<220> FEATURE:
<221> NAME/KEY: CDS
<222> LOCATION: (1)...(348)

<400> SEQUENCE: 41

| | | |
|---|---|---|
| gcc atc gcc agt tgc aat agt gtg ata att tac cga tgc ctt gag aat | | 48 |
| Ala Ile Ala Ser Cys Asn Ser Val Ile Ile Tyr Arg Cys Leu Glu Asn | | |
| 1               5                   10                  15 | | |
| | | |
| ggt ggt ttt ggt ctt cta caa aat tat gtt gat gag gat aag gat gag | | 96 |
| Gly Gly Phe Gly Leu Leu Gln Asn Tyr Val Asp Glu Asp Lys Asp Glu | | |
|             20                  25                  30 | | |
| | | |
| tca ttc tac act cta agc tgg acc atc gat caa gtt gat agc tca ccg | | 144 |
| Ser Phe Tyr Thr Leu Ser Trp Thr Ile Asp Gln Val Asp Ser Ser Pro | | |
|         35                  40                  45 | | |
| | | |
| ctg ttg gtg gcc gca gga agc aat cgg atc att cgg gtc atc aat tgt | | 192 |
| Leu Leu Val Ala Ala Gly Ser Asn Arg Ile Ile Arg Val Ile Asn Cys | | |
|     50                  55                  60 | | |
| | | |
| gct acc gaa aag tta gat aag agc tta gtt ggc cat ggt ggt tca ata | | 240 |
| Ala Thr Glu Lys Leu Asp Lys Ser Leu Val Gly His Gly Gly Ser Ile | | |
| 65                  70                  75                  80 | | |
| | | |
| cat gag ata agg act cat gcc tcg aag cca tca ctc atc att tct gcc | | 288 |
| His Glu Ile Arg Thr His Ala Ser Lys Pro Ser Leu Ile Ile Ser Ala | | |
|             85                  90                  95 | | |
| | | |
| agc aag gat gaa tct att agg cta tgg aat gtc cat act ggg att tgc | | 336 |
| Ser Lys Asp Glu Ser Ile Arg Leu Trp Asn Val His Thr Gly Ile Cys | | |
|         100                 105                 110 | | |
| | | |
| atc tta gtc ttt | | 348 |
| Ile Leu Val Phe | | |
|     115 | | |

<210> SEQ ID NO 42
<211> LENGTH: 116
<212> TYPE: PRT
<213> ORGANISM: Zea mays

<400> SEQUENCE: 42

```
Ala Ile Ala Ser Cys Asn Ser Val Ile Ile Tyr Arg Cys Leu Glu Asn
 1               5                  10                  15

Gly Gly Phe Gly Leu Leu Gln Asn Tyr Val Asp Asp Lys Asp Glu
            20                  25                  30

Ser Phe Tyr Thr Leu Ser Trp Thr Ile Asp Gln Val Asp Ser Ser Pro
        35                  40                  45

Leu Leu Val Ala Ala Gly Ser Asn Arg Ile Ile Arg Val Ile Asn Cys
 50                  55                  60

Ala Thr Glu Lys Leu Asp Lys Ser Leu Val Gly His Gly Gly Ser Ile
 65              70                  75                  80

His Glu Ile Arg Thr His Ala Ser Lys Pro Ser Leu Ile Ile Ser Ala
                85                  90                  95

Ser Lys Asp Glu Ser Ile Arg Leu Trp Asn Val His Thr Gly Ile Cys
            100                 105                 110

Ile Leu Val Phe
        115

<210> SEQ ID NO 43
<211> LENGTH: 488
<212> TYPE: DNA
<213> ORGANISM: Zea mays
<220> FEATURE:
<221> NAME/KEY: CDS
<222> LOCATION: (2)...(433)
<220> FEATURE:
<221> NAME/KEY: misc_feature
<222> LOCATION: 1, 454, 462, 471
<223> OTHER INFORMATION: n = A, T, C or G

<400> SEQUENCE: 43 n aag ttt cca aca aaa tat gtc cag ttt cca gtc ttg att gct gca gta       49
  Lys Phe Pro Thr Lys Tyr Val Gln Phe Pro Val Leu Ile Ala Ala Val
   1               5                  10                  15 cac tct aac tat gtt gat tgt aca aga tgg ctt ggt gac ttc atc cta        97
His Ser Asn Tyr Val Asp Cys Thr Arg Trp Leu Gly Asp Phe Ile Leu
            20                  25                  30 tca aag agt gtt gac aat gaa att gtg ctt tgg gaa ccg aag aca aaa       145
Ser Lys Ser Val Asp Asn Glu Ile Val Leu Trp Glu Pro Lys Thr Lys
        35                  40                  45 gaa cag agt cct ggg gag gga agc atc gat atc ctt cag aag tat cct       193
Glu Gln Ser Pro Gly Glu Gly Ser Ile Asp Ile Leu Gln Lys Tyr Pro
 50                  55                  60 gtc cca gaa tgt gac att tgg ttt atc aaa ttt tca tgt gat ttt cac       241
Val Pro Glu Cys Asp Ile Trp Phe Ile Lys Phe Ser Cys Asp Phe His
 65                  70                  75                  80 ttc aat cag ttg gcg ata ggc aac cgt gaa ggc aaa atc tac gtg tgg       289
Phe Asn Gln Leu Ala Ile Gly Asn Arg Glu Gly Lys Ile Tyr Val Trp
                85                  90                  95 gaa gta cag tcc agc cct cct gtc ctc att gct cgg ctg tat aat cag       337
Glu Val Gln Ser Ser Pro Pro Val Leu Ile Ala Arg Leu Tyr Asn Gln
            100                 105                 110 cag tgt aaa tcg ccg ata aga caa act gca gtg tcc ttc gat gga agc       385
Gln Cys Lys Ser Pro Ile Arg Gln Thr Ala Val Ser Phe Asp Gly Ser
        115                 120                 125 aca atc ctt gga gct ggt gaa gac ggc acc atc tgg cgg tgg gga tga       433
Thr Ile Leu Gly Ala Gly Glu Asp Gly Thr Ile Trp Arg Trp Gly *
130                 135                 140 agtggaccat ccgagctcca naagctgang aagtgttncc ggctcaatgc tggtg          488

<210> SEQ ID NO 44
```

```
<211> LENGTH: 143
<212> TYPE: PRT
<213> ORGANISM: Zea mays

<400> SEQUENCE: 44

Lys Phe Pro Thr Lys Tyr Val Gln Phe Pro Val Leu Ile Ala Ala Val
1               5                  10                  15

His Ser Asn Tyr Val Asp Cys Thr Arg Trp Leu Gly Asp Phe Ile Leu
            20                  25                  30

Ser Lys Ser Val Asp Asn Glu Ile Val Leu Trp Glu Pro Lys Thr Lys
        35                  40                  45

Glu Gln Ser Pro Gly Glu Gly Ser Ile Asp Ile Leu Gln Lys Tyr Pro
    50                  55                  60

Val Pro Glu Cys Asp Ile Trp Phe Ile Lys Phe Ser Cys Asp Phe His
65                  70                  75                  80

Phe Asn Gln Leu Ala Ile Gly Asn Arg Glu Gly Lys Ile Tyr Val Trp
                85                  90                  95

Glu Val Gln Ser Ser Pro Pro Val Leu Ile Ala Arg Leu Tyr Asn Gln
            100                 105                 110

Gln Cys Lys Ser Pro Ile Arg Gln Thr Ala Val Ser Phe Asp Gly Ser
        115                 120                 125

Thr Ile Leu Gly Ala Gly Glu Asp Gly Thr Ile Trp Arg Trp Gly
    130                 135                 140

<210> SEQ ID NO 45
<211> LENGTH: 460
<212> TYPE: DNA
<213> ORGANISM: Eucalyptus grandis
<220> FEATURE:
<221> NAME/KEY: CDS
<222> LOCATION: (116)...(328)
<220> FEATURE:
<221> NAME/KEY: misc_feature
<222> LOCATION: 319, 331, 355, 387, 426, 427, 428, 437, 447, 451
<223> OTHER INFORMATION: n = A, T, C or G

<400> SEQUENCE: 45
ctcgttcgcc gttcggcgtc ttcaccggcg gcgcgcgccg cactgcgtac ccaccggctg      60
tcgcgttctc gcggatcgaa ctcgaggaaa aggcatcggc ggcggatcgg ggcaa atg     118
                                                              Met
                                                              1 gcg aag atc gcg ccc ggg tgc gaa ccg gtg gcg ggg acg ctg acc ccg        166
Ala Lys Ile Ala Pro Gly Cys Glu Pro Val Ala Gly Thr Leu Thr Pro
            5                  10                  15 tcg aag aag agg gag tac agg gtc acc aac agg ctc cag gag ggg aag        214
Ser Lys Lys Arg Glu Tyr Arg Val Thr Asn Arg Leu Gln Glu Gly Lys
        20                  25                  30 cgt ccc ctc tat gcc gtc gtc ttc aac ttc atc gac tcc cgc tac ttc        262
Arg Pro Leu Tyr Ala Val Val Phe Asn Phe Ile Asp Ser Arg Tyr Phe
    35                  40                  45 aac gta ttc gcc acc gtc ggc ggc aac cgg ggt tac tgt tta tca agt        310
Asn Val Phe Ala Thr Val Gly Gly Asn Arg Gly Tyr Cys Leu Ser Ser
50                  55                  60                  65 gtc tcg aan ggg gag taa tanctgtgtt gcagtcatac attgatnaag              358
Val Ser Xaa Gly Glu *
                70 ataaggacga gtccgttta cacggtcang tggggcgtgc aaacatttat agaaccccaa      418 ttgtgggnnn gcgggaggna acaattggna acnatcgggt gt                        460
```

```
<210> SEQ ID NO 46
<211> LENGTH: 70
<212> TYPE: PRT
<213> ORGANISM: Eucalyptus grandis
<220> FEATURE:
<221> NAME/KEY: VARIANT
<222> LOCATION: (68)...(68)
<223> OTHER INFORMATION: Xaa = Any Amino Acid

<400> SEQUENCE: 46

Met Ala Lys Ile Ala Pro Gly Cys Glu Pro Val Ala Gly Thr Leu Thr
1               5                   10                  15

Pro Ser Lys Lys Arg Glu Tyr Arg Val Thr Asn Arg Leu Gln Glu Gly
            20                  25                  30

Lys Arg Pro Leu Tyr Ala Val Val Phe Asn Phe Ile Asp Ser Arg Tyr
        35                  40                  45

Phe Asn Val Phe Ala Thr Val Gly Gly Asn Arg Gly Tyr Cys Leu Ser
    50                  55                  60

Ser Val Ser Xaa Gly Glu
65              70

<210> SEQ ID NO 47
<211> LENGTH: 521
<212> TYPE: DNA
<213> ORGANISM: Helianthus sp.
<220> FEATURE:
<221> NAME/KEY: CDS
<222> LOCATION: (4)...(300)
<220> FEATURE:
<221> NAME/KEY: misc_feature
<222> LOCATION: (390)...(390)
<223> OTHER INFORMATION: n = A, T, C or G

<400> SEQUENCE: 47 ctt ggt gat ttc ata cta tct aag agt gta gac aat gag ttc ata ttg        48
    Gly Asp Phe Ile Leu Ser Lys Ser Val Asp Asn Glu Phe Ile Leu
    1               5                   10                  15 tgg gag ccg aag atg aaa gag cag tct cca gga gag ggc acg gtg gat        96
Trp Glu Pro Lys Met Lys Glu Gln Ser Pro Gly Glu Gly Thr Val Asp
                20                  25                  30 att ctt cag aaa tat cct gta cct gat tgt gac atc tgg ttt ata aag       144
Ile Leu Gln Lys Tyr Pro Val Pro Asp Cys Asp Ile Trp Phe Ile Lys
            35                  40                  45 ctt tcc tgt gat ttc cat tac aat gca gca gct att ggt aac aga gaa       192
Leu Ser Cys Asp Phe His Tyr Asn Ala Ala Ala Ile Gly Asn Arg Glu
        50                  55                  60 gga aaa atc tat gta tgg gaa ttg cag act agc ccg cct tct ctt att       240
Gly Lys Ile Tyr Val Trp Glu Leu Gln Thr Ser Pro Pro Ser Leu Ile
    65                  70                  75 gca agg tta tct cat att caa gtc caa atc gcc aat cag gca aac tgc       288
Ala Arg Leu Ser His Ile Gln Val Gln Ile Ala Asn Gln Ala Asn Cys
80                  85                  90                  95 tat gtc att tga tggaagcaca attctgagtt gctgtgaaga tggcaccatc           340
Tyr Val Ile * tggcgttggg atactgttgc aacgtcgtag cttgtgttgg tttgaaacan gtcatgttgt     400
gtaccatgta tattccttca gcaatttcgt ttgttttccg tggtgatgat tgagggcatt    460
ttaatttgtt cttattaaa ctatgatagt aaggatgtta ttccgttttta gtgaacngnc    520 c                                                                    521

<210> SEQ ID NO 48
<211> LENGTH: 98
```

```
<212> TYPE: PRT
<213> ORGANISM: Helianthus sp.

<400> SEQUENCE: 48

Gly Asp Phe Ile Leu Ser Lys Ser Val Asp Asn Glu Phe Ile Leu Trp
 1               5                  10                  15

Glu Pro Lys Met Lys Glu Gln Ser Pro Gly Glu Gly Thr Val Asp Ile
            20                  25                  30

Leu Gln Lys Tyr Pro Val Pro Asp Cys Asp Ile Trp Phe Ile Lys Leu
        35                  40                  45

Ser Cys Asp Phe His Tyr Asn Ala Ala Ala Ile Gly Asn Arg Glu Gly
    50                  55                  60

Lys Ile Tyr Val Trp Glu Leu Gln Thr Ser Pro Pro Ser Leu Ile Ala
65                  70                  75                  80

Arg Leu Ser His Ile Gln Val Gln Ile Ala Asn Gln Ala Asn Cys Tyr
                85                  90                  95

Val Ile

<210> SEQ ID NO 49
<211> LENGTH: 658
<212> TYPE: DNA
<213> ORGANISM: Catalpa speciosa
<220> FEATURE:
<221> NAME/KEY: CDS
<222> LOCATION: (35)...(271)
<220> FEATURE:
<221> NAME/KEY: misc_feature
<222> LOCATION: 367, 445, 456, 483, 492, 509, 549, 554, 563, 579, 584,
      602, 611, 648, 657
<223> OTHER INFORMATION: n = A, T, C or G

<400> SEQUENCE: 49
ggcatacagg cggtgctaat ctgcaggtaa ggag atg gca aaa att ccg ttg ggt      55
                                     Met Ala Lys Ile Pro Leu Gly
                                      1               5 tgt gag ccc atg gtg ggt tcc tta acg ccg tcg aag aaa cgg gag tat     103
Cys Glu Pro Met Val Gly Ser Leu Thr Pro Ser Lys Lys Arg Glu Tyr
         10                  15                  20 agg gtc acc aac agg ctc cag gaa ggc aaa cgc ccc att tac gcc gtc     151
Arg Val Thr Asn Arg Leu Gln Glu Gly Lys Arg Pro Ile Tyr Ala Val
     25                  30                  35 gtt ttc aac ttc att gac tcc cgt tac ttc aac gct ttc gcc act gcc     199
Val Phe Asn Phe Ile Asp Ser Arg Tyr Phe Asn Ala Phe Ala Thr Ala
 40                  45                  50                  55 ggt ggc aat cgc gtg act gta tac caa gtg cct aga agg tgg tgt tat     247
Gly Gly Asn Arg Val Thr Val Tyr Gln Val Pro Arg Arg Trp Cys Tyr
             60                  65                  70 agc tgt act aca gtc cta cat tga tgaagataaa gatgaatctt tctacactgt    301
Ser Cys Thr Thr Val Leu His  *
                 75 aagttgggct tgcaatattg atgggactcc attcttggtg gctggaggac ttaatggaat   361 tattcnagtt attgatactg caatgagaa aatatacaag agtttgtggg tcatggggaa    421 tcaataaacg aaatccaact caancgctga acancactt gttgtgtcaa caaacaaaga    481 tnaatcttac nctgtggaat atcatacngg atatcatttg atatttctgg gctgtggcat   541 ccatgaantc tangggctc ancctctaca cacgtataa acntgaaggt aaatgcagat    601 nggcatgaan attggcaagt aaaacttctg cgttctcaat ccaaaancat caatang      658

<210> SEQ ID NO 50
```

```
<211> LENGTH: 78
<212> TYPE: PRT
<213> ORGANISM: Catalpa speciosa

<400> SEQUENCE: 50

Met Ala Lys Ile Pro Leu Gly Cys Glu Pro Met Val Gly Ser Leu Thr
 1               5                  10                  15

Pro Ser Lys Lys Arg Glu Tyr Arg Val Thr Asn Arg Leu Gln Glu Gly
            20                  25                  30

Lys Arg Pro Ile Tyr Ala Val Val Phe Asn Phe Ile Asp Ser Arg Tyr
        35                  40                  45

Phe Asn Ala Phe Ala Thr Ala Gly Gly Asn Arg Val Thr Val Tyr Gln
    50                  55                  60

Val Pro Arg Arg Trp Cys Tyr Ser Cys Thr Thr Val Leu His
65                  70                  75

<210> SEQ ID NO 51
<211> LENGTH: 631
<212> TYPE: DNA
<213> ORGANISM: Zea mays
<220> FEATURE:
<221> NAME/KEY: CDS
<222> LOCATION: (10)...(489)
<220> FEATURE:
<221> NAME/KEY: misc_feature
<222> LOCATION: (466)...(466)
<223> OTHER INFORMATION: n = A, T, C or G

<400> SEQUENCE: 51 ggcacgagt cca aca aaa tat gtc cag ttt cca gtc ttg att gct gca gta         51
          Pro Thr Lys Tyr Val Gln Phe Pro Val Leu Ile Ala Ala Val
            1               5                  10 cac tct aac tat gtt gat tgt aca aga tgg ctt ggt gac ttc atc cta          99
His Ser Asn Tyr Val Asp Cys Thr Arg Trp Leu Gly Asp Phe Ile Leu
 15                  20                  25                  30 tca aag agt gtt gac aat gaa att gtg ctt tgg gaa ccg aag aca aaa         147
Ser Lys Ser Val Asp Asn Glu Ile Val Leu Trp Glu Pro Lys Thr Lys
                 35                  40                  45 gaa cag agt cct ggg gag gga agc atc gat atc ctt cag aag tat cct         195
Glu Gln Ser Pro Gly Glu Gly Ser Ile Asp Ile Leu Gln Lys Tyr Pro
             50                  55                  60 gtc cca gaa tgt gac att tgg ttt atc aaa ttt tca tgt gat ttt cac         243
Val Pro Glu Cys Asp Ile Trp Phe Ile Lys Phe Ser Cys Asp Phe His
         65                  70                  75 ttc aat cag ttg gcg ata ggc aac cgt gaa ggc aaa atc tac gtg tgg         291
Phe Asn Gln Leu Ala Ile Gly Asn Arg Glu Gly Lys Ile Tyr Val Trp
     80                  85                  90 gaa gta cag tcc agc cct cct gtc ctc att gct cgg ctg tat aat cag         339
Glu Val Gln Ser Ser Pro Pro Val Leu Ile Ala Arg Leu Tyr Asn Gln
 95                 100                 105                 110 cag tgt aaa tcg ccg ata aga caa act gca gtg tcc ttc gat gga aca         387
Gln Cys Lys Ser Pro Ile Arg Gln Thr Ala Val Ser Phe Asp Gly Thr
                115                 120                 125 caa tcc ttg gag ctg gtg aag acg cac cat ctg gcg gtg ggg atg aag         435
Gln Ser Leu Glu Leu Val Lys Thr His His Leu Ala Val Gly Met Lys
            130                 135                 140 tgg acc atc cga gct cca gaa act gaa gaa ntt tgc cgc tca atg ctg         483
Trp Thr Ile Arg Ala Pro Glu Thr Glu Glu Xaa Cys Arg Ser Met Leu
        145                 150                 155 gac tga tggttacgct cggttggggt tgcgatggtt gaaccgtggt ggaaatgcca          539
Asp *
```

```
ctggtgtttt tcaatcaaaa tggtnggtgt taacagaata atgaatgctc caaagttgaa    599
antnggangc tgttgctaaa aaaaaaaaaa aa                                  631

<210> SEQ ID NO 52
<211> LENGTH: 159
<212> TYPE: PRT
<213> ORGANISM: Zea mays
<220> FEATURE:
<221> NAME/KEY: CONFLICT
<222> LOCATION: (153)...(153)
<223> OTHER INFORMATION: Xaa = Any Amino Acid

<400> SEQUENCE: 52

Pro Thr Lys Tyr Val Gln Phe Pro Val Leu Ile Ala Ala Val His Ser
 1               5                  10                  15

Asn Tyr Val Asp Cys Thr Arg Trp Leu Gly Asp Phe Ile Leu Ser Lys
             20                  25                  30

Ser Val Asp Asn Glu Ile Val Leu Trp Glu Pro Lys Thr Lys Glu Gln
         35                  40                  45

Ser Pro Gly Glu Gly Ser Ile Asp Ile Leu Gln Lys Tyr Pro Val Pro
     50                  55                  60

Glu Cys Asp Ile Trp Phe Ile Lys Phe Ser Cys Asp Phe His Phe Asn
 65                  70                  75                  80

Gln Leu Ala Ile Gly Asn Arg Glu Gly Lys Ile Tyr Val Trp Glu Val
                 85                  90                  95

Gln Ser Ser Pro Pro Val Leu Ile Ala Arg Leu Tyr Asn Gln Gln Cys
            100                 105                 110

Lys Ser Pro Ile Arg Gln Thr Ala Val Ser Phe Asp Gly Thr Gln Ser
        115                 120                 125

Leu Glu Leu Val Lys Thr His His Leu Ala Val Gly Met Lys Trp Thr
    130                 135                 140

Ile Arg Ala Pro Glu Thr Glu Glu Xaa Cys Arg Ser Met Leu Asp
145                 150                 155

<210> SEQ ID NO 53
<211> LENGTH: 777
<212> TYPE: DNA
<213> ORGANISM: Zea mays
<220> FEATURE:
<221> NAME/KEY: CDS
<222> LOCATION: (16)...(522)
<220> FEATURE:
<221> NAME/KEY: misc_feature
<222> LOCATION: 597, 611, 639, 657, 681, 692, 699, 702, 710, 718, 748,
      749, 753, 772
<223> OTHER INFORMATION: N = A, T, C or G

<400> SEQUENCE: 53
ggcacgaggt tagct aag agc ttt gtt ggc cat ggc gac tca ata aat gag     51
                Lys Ser Phe Val Gly His Gly Asp Ser Ile Asn Glu
                 1               5                  10 ata aga act caa ccg ttg aag cct tcg ctc atc att tct gca agc aag      99
Ile Arg Thr Gln Pro Leu Lys Pro Ser Leu Ile Ile Ser Ala Ser Lys
         15                  20                  25 gat gaa tct gtt agg cta tgg aat gtc cat aca ggg atc tgt atc ttg     147
Asp Glu Ser Val Arg Leu Trp Asn Val His Thr Gly Ile Cys Ile Leu
     30                  35                  40 ata ttt gct gga gct gga ggt cat cgc aat gaa gta ttg agt gtt gac     195
Ile Phe Ala Gly Ala Gly Gly His Arg Asn Glu Val Leu Ser Val Asp
 45                  50                  55                  60 ttc cat cct agt gat att gaa cgt ttt gca agt tgt ggc atg gac aac     243
```

```
                                                                                            -continued Phe His Pro Ser Asp Ile Glu Arg Phe Ala Ser Cys Gly Met Asp Asn
             65                  70                  75 act gtg aaa atc tgg tca atg aaa gaa ttt tgg cta tat gtt gac aaa      291
Thr Val Lys Ile Trp Ser Met Lys Glu Phe Trp Leu Tyr Val Asp Lys
             80                  85                  90 tca tat tca tgg act gac ctt cca tca aag ttt cca aca aaa tat gtc      339
Ser Tyr Ser Trp Thr Asp Leu Pro Ser Lys Phe Pro Thr Lys Tyr Val
         95                 100                 105 cag ttt cca gtc ttg att gct gca gta cac tct aac tat gtt gat tgt      387
Gln Phe Pro Val Leu Ile Ala Ala Val His Ser Asn Tyr Val Asp Cys
    110                 115                 120 aca aga tgg ctt ggt gac ttc atc cta tca aag agt gtt gac aat gaa      435
Thr Arg Trp Leu Gly Asp Phe Ile Leu Ser Lys Ser Val Asp Asn Glu
125                 130                 135                 140 att gtg ctt tgg gaa ccg aag aca aaa gac aga tcc tgg ggg aag gaa      483
Ile Val Leu Trp Glu Pro Lys Thr Lys Asp Arg Ser Trp Gly Lys Glu
                145                 150                 155 gca tcg ata tcc ttc aga agt acc tgt ccc aga atg tga cattgggttt      532
Ala Ser Ile Ser Phe Arg Ser Thr Cys Pro Arg Met *
                160                 165 atcaaatttt catgtgattt tcacttcaat cagtggcgat aggcaaccgt gaaagcaaat    592
ctacntttgg gaagtacanc cagccctctg tcctcatgct cgctgtntat cacatgtaat    652
cccanaaaaa acgcatgtct ccatgaacnc atcctggacn ggtaaangcn cactgcgngg    712 aaaatacac cacccaacga aaattcccca tccgannagt nccgtgggtc aagtaactgn     772
gaatc                                                                777

<210> SEQ ID NO 54
<211> LENGTH: 168
<212> TYPE: PRT
<213> ORGANISM: Zea mays

<400> SEQUENCE: 54

Lys Ser Phe Val Gly His Gly Asp Ser Ile Asn Glu Ile Arg Thr Gln
 1               5                  10                  15

Pro Leu Lys Pro Ser Leu Ile Ile Ser Ala Ser Lys Asp Glu Ser Val
             20                  25                  30

Arg Leu Trp Asn Val His Thr Gly Ile Cys Ile Leu Ile Phe Ala Gly
         35                  40                  45

Ala Gly His Arg Asn Glu Val Leu Ser Val Asp Phe His Pro Ser
     50                  55                  60

Asp Ile Glu Arg Phe Ala Ser Cys Gly Met Asp Asn Thr Val Lys Ile
 65                  70                  75                  80

Trp Ser Met Lys Glu Phe Trp Leu Tyr Val Asp Lys Ser Tyr Ser Trp
                 85                  90                  95

Thr Asp Leu Pro Ser Lys Phe Pro Thr Lys Tyr Val Gln Phe Pro Val
            100                 105                 110

Leu Ile Ala Ala Val His Ser Asn Tyr Val Asp Cys Thr Arg Trp Leu
        115                 120                 125

Gly Asp Phe Ile Leu Ser Lys Ser Val Asp Asn Glu Ile Val Leu Trp
    130                 135                 140

Glu Pro Lys Thr Lys Asp Arg Ser Trp Gly Lys Glu Ala Ser Ile Ser
145                 150                 155                 160

Phe Arg Ser Thr Cys Pro Arg Met
                165
```

-continued

```
<210> SEQ ID NO 55
<211> LENGTH: 466
<212> TYPE: DNA
<213> ORGANISM: Zea mays
<220> FEATURE:
<221> NAME/KEY: CDS
<222> LOCATION: (9)...(464)
<220> FEATURE:
<221> NAME/KEY: misc_feature
<222> LOCATION: 305, 441
<223> OTHER INFORMATION: n = A, T, C or G

<400> SEQUENCE: 55 gaagcaat ggg atc att cgg gtc atc aat tgt gct aca gaa aag tta gct        50
         Gly Ile Ile Arg Val Ile Asn Cys Ala Thr Glu Lys Leu Ala
          1               5                  10 aag agc ttt gtt ggc cat ggc gac tca ata aat gag ata aga act caa        98
Lys Ser Phe Val Gly His Gly Asp Ser Ile Asn Glu Ile Arg Thr Gln
 15                  20                  25                  30 ccg ttg aag cct tcg ctc atc att tct gca agc aag gat gaa tct gtt       146
Pro Leu Lys Pro Ser Leu Ile Ile Ser Ala Ser Lys Asp Glu Ser Val
                 35                  40                  45 agg cta tgg aat gtc cat aca ggg atc tgt atc ttg ata ttt gct gga       194
Arg Leu Trp Asn Val His Thr Gly Ile Cys Ile Leu Ile Phe Ala Gly
             50                  55                  60 gct gga ggt cat cgc aat gaa gta ttg agt gtt gac ttc cat cct agt       242
Ala Gly Gly His Arg Asn Glu Val Leu Ser Val Asp Phe His Pro Ser
         65                  70                  75 gat att gaa cgt ttt gca agt tgt ggc atg gac aac act gtg aaa atc       290
Asp Ile Glu Arg Phe Ala Ser Cys Gly Met Asp Asn Thr Val Lys Ile
 80                  85                  90 tgg tca atg aaa gan ttt tgg cta tat gtt gac aaa tca tat tca tgg       338
Trp Ser Met Lys Xaa Phe Trp Leu Tyr Val Asp Lys Ser Tyr Ser Trp
 95                 100                 105                 110 act gac ctt cca tca aag ttt cca aca aaa tat gtc cag ttt cca gtc       386
Thr Asp Leu Pro Ser Lys Phe Pro Thr Lys Tyr Val Gln Phe Pro Val
                115                 120                 125 ttg att gct gca gta cac tct aac tat gtt gat tgt aca aga tgg ctt       434
Leu Ile Ala Ala Val His Ser Asn Tyr Val Asp Cys Thr Arg Trp Leu
            130                 135                 140 ggt gac ntc atc cta tca aag agt gtt gac aa                            466
Gly Asp Xaa Ile Leu Ser Lys Ser Val Asp
            145                 150

<210> SEQ ID NO 56
<211> LENGTH: 152
<212> TYPE: PRT
<213> ORGANISM: Zea mays
<220> FEATURE:
<221> NAME/KEY: VARIANT
<222> LOCATION: 99, 145
<223> OTHER INFORMATION: Xaa = Any Amino Acid

<400> SEQUENCE: 56

Gly Ile Ile Arg Val Ile Asn Cys Ala Thr Glu Lys Leu Ala Lys Ser
 1               5                  10                  15

Phe Val Gly His Gly Asp Ser Ile Asn Glu Ile Arg Thr Gln Pro Leu
                 20                  25                  30

Lys Pro Ser Leu Ile Ile Ser Ala Ser Lys Asp Glu Ser Val Arg Leu
             35                  40                  45

Trp Asn Val His Thr Gly Ile Cys Ile Leu Ile Phe Ala Gly Ala Gly
         50                  55                  60

Gly His Arg Asn Glu Val Leu Ser Val Asp Phe His Pro Ser Asp Ile
```

```
                65                  70                  75                  80
Glu Arg Phe Ala Ser Cys Gly Met Asp Asn Thr Val Lys Ile Trp Ser
                        85                  90                  95

Met Lys Xaa Phe Trp Leu Tyr Val Asp Lys Ser Tyr Ser Trp Thr Asp
            100                 105                 110

Leu Pro Ser Lys Phe Pro Thr Lys Tyr Val Gln Phe Pro Val Leu Ile
            115                 120                 125

Ala Ala Val His Ser Asn Tyr Val Asp Cys Thr Arg Trp Leu Gly Asp
        130                 135                 140

Xaa Ile Leu Ser Lys Ser Val Asp
145                 150

<210> SEQ ID NO 57
<211> LENGTH: 464
<212> TYPE: DNA
<213> ORGANISM: Zea mays
<220> FEATURE:
<221> NAME/KEY: CDS
<222> LOCATION: (1)...(189)
<220> FEATURE:
<221> NAME/KEY: misc_feature
<222> LOCATION: 369, 447
<223> OTHER INFORMATION: n = A, T, C or G

<400> SEQUENCE: 57 ggc aaa atc tac gtg tgg gaa gta cag tcc agc cct cct gtc ctc att         48
Gly Lys Ile Tyr Val Trp Glu Val Gln Ser Ser Pro Pro Val Leu Ile
 1               5                  10                  15 gct cgg ctg tat aat cag cag tgt aaa tcg ccg ata aga caa act gca         96
Ala Arg Leu Tyr Asn Gln Gln Cys Lys Ser Pro Ile Arg Gln Thr Ala
                20                  25                  30 gtg tcc ttc gat gga agc aca atc ctt gga gct ggt gaa gac ggc acc        144
Val Ser Phe Asp Gly Ser Thr Ile Leu Gly Ala Gly Glu Asp Gly Thr
            35                  40                  45 atc tgg cgg tgg gat gaa gtg gac cat ccg agc tcc aga aac tga           189
Ile Trp Arg Trp Asp Glu Val Asp His Pro Ser Ser Arg Asn *
        50                  55                  60 agaagtgttg ccgctcaatg ctggactgat ggttacgctc ggttggggtt gcgatggttg      249
aatccgttgg tggaaagtgc cacctggtgt tttttctagt caaaatggtt ggtgttaaca      309
gaatattgaa tgcttcgaat gttgaaagtt gggatgcttg tgctggtact ctgctccgtn      369
gacgagtgaa cttaggtgcc gttttggttca catatttgta acgtaatggg taacagataa     429
cgttaaatca tgtttgtntt aattcaaccg taaaa                                 464

<210> SEQ ID NO 58
<211> LENGTH: 62
<212> TYPE: PRT
<213> ORGANISM: Zea mays

<400> SEQUENCE: 58

Gly Lys Ile Tyr Val Trp Glu Val Gln Ser Ser Pro Pro Val Leu Ile
 1               5                  10                  15

Ala Arg Leu Tyr Asn Gln Gln Cys Lys Ser Pro Ile Arg Gln Thr Ala
                20                  25                  30

Val Ser Phe Asp Gly Ser Thr Ile Leu Gly Ala Gly Glu Asp Gly Thr
            35                  40                  45

Ile Trp Arg Trp Asp Glu Val Asp His Pro Ser Ser Arg Asn
        50                  55                  60
```

```
<210> SEQ ID NO 59
<211> LENGTH: 299
<212> TYPE: DNA
<213> ORGANISM: Zea mays
<220> FEATURE:
<221> NAME/KEY: CDS
<222> LOCATION: (1)...(201)
<220> FEATURE:
<221> NAME/KEY: misc_feature
<222> LOCATION: 203, 270
<223> OTHER INFORMATION: n = A, T, C or G

<400> SEQUENCE: 59 ggc aac cgt gaa ggc aaa atc tac gtg tgg gaa gta cag tcc agc cct        48
Gly Asn Arg Glu Gly Lys Ile Tyr Val Trp Glu Val Gln Ser Ser Pro
  1               5                  10                  15 cct gtc ctc att gct cgg ctg tat aat cag cag tgt aaa tcg ccg ata        96
Pro Val Leu Ile Ala Arg Leu Tyr Asn Gln Gln Cys Lys Ser Pro Ile
             20                  25                  30 aga caa act gca gtg tcc ttc gat gga agc aca atc ctt gga gct ggt       144
Arg Gln Thr Ala Val Ser Phe Asp Gly Ser Thr Ile Leu Gly Ala Gly
         35                  40                  45 gaa gac ggt acc atc tgg cgg tgg gat gaa gtg gac cat ccg agc tcc       192
Glu Asp Gly Thr Ile Trp Arg Trp Asp Glu Val Asp His Pro Ser Ser
     50                  55                  60 aga aac tga anaagtgttg ccgctcaatg ctggactgat ggttacgctc              241
Arg Asn *
 65 ggttggggtt gcgatggttg aatccgttng tggaaagtgc cacctggtgt tttttcta      299

<210> SEQ ID NO 60
<211> LENGTH: 66
<212> TYPE: PRT
<213> ORGANISM: Zea mays

<400> SEQUENCE: 60

Gly Asn Arg Glu Gly Lys Ile Tyr Val Trp Glu Val Gln Ser Ser Pro
  1               5                  10                  15

Pro Val Leu Ile Ala Arg Leu Tyr Asn Gln Gln Cys Lys Ser Pro Ile
             20                  25                  30

Arg Gln Thr Ala Val Ser Phe Asp Gly Ser Thr Ile Leu Gly Ala Gly
         35                  40                  45

Glu Asp Gly Thr Ile Trp Arg Trp Asp Glu Val Asp His Pro Ser Ser
     50                  55                  60

Arg Asn
 65

<210> SEQ ID NO 61
<211> LENGTH: 434
<212> TYPE: DNA
<213> ORGANISM: Zea mays
<220> FEATURE:
<221> NAME/KEY: CDS
<222> LOCATION: (1)...(384)
<220> FEATURE:
<221> NAME/KEY: misc_feature
<222> LOCATION: 207, 243, 247, 251, 272, 369, 374
<223> OTHER INFORMATION: n = A, T, C or G

<400> SEQUENCE: 61 atg ccg cct tcc aaa gca cgc cga aag agg tca ctt cgt gat atc act        48
Met Pro Pro Ser Lys Ala Arg Arg Lys Arg Ser Leu Arg Asp Ile Thr
  1               5                  10                  15 gcc acc gtt gcc act ggg act gtt gcc aac tcg aaa cct ggc tca tca        96
Ala Thr Val Ala Thr Gly Thr Val Ala Asn Ser Lys Pro Gly Ser Ser
```

-continued

```
Ala Thr Val Ala Thr Gly Thr Val Ala Asn Ser Lys Pro Gly Ser Ser
             20                  25                  30 tcg acg aac gag ggg aag caa cag gac aag aaa aag gag ggt cca cag      144
Ser Thr Asn Glu Gly Lys Gln Gln Asp Lys Lys Lys Glu Gly Pro Gln
         35                  40                  45 gaa acc gga cat ccc acc att acc gcc ggt ggt ggt gaa tat agt ccc      192
Glu Thr Gly His Pro Thr Ile Thr Ala Gly Gly Gly Glu Tyr Ser Pro
 50                  55                  60 acg aac aag gat tan gat gtt gaa att agt gga agg gct act cgt gcc      240
Thr Asn Lys Asp Xaa Asp Val Glu Ile Ser Gly Arg Ala Thr Arg Ala
 65                  70                  75                  80 tan tcc nga anc gaa aat tac aac ccc aat anc caa tta ttc tgt tgg      288
Xaa Ser Xaa Xaa Glu Asn Tyr Asn Pro Asn Xaa Gln Leu Phe Cys Trp
             85                  90                  95 gga aat cca ccc gat ctt atg cca tcc ggg ttt cca att tcc ctt gaa      336
Gly Asn Pro Pro Asp Leu Met Pro Ser Gly Phe Pro Ile Ser Leu Glu
             100                 105                 110 aat gcc cta cta tta aat ttt ttt tgg cca ccn ccc cnt ttg caa taa      384
Asn Ala Leu Leu Leu Asn Phe Phe Trp Pro Pro Pro Xaa Leu Gln *
             115                 120                 125 ttgtttaaaa attttaccaa aacccttnaa angnggggt tttggggccc                 434
```

<210> SEQ ID NO 62
<211> LENGTH: 127
<212> TYPE: PRT
<213> ORGANISM: Zea mays
<220> FEATURE:
<221> NAME/KEY: VARIANT
<222> LOCATION: 69, 81, 83, 84, 91, 123, 125
<223> OTHER INFORMATION: Xaa = Any Amino Acid

<400> SEQUENCE: 62

```
Met Pro Pro Ser Lys Ala Arg Arg Lys Arg Ser Leu Arg Asp Ile Thr
 1               5                  10                  15

Ala Thr Val Ala Thr Gly Thr Val Ala Asn Ser Lys Pro Gly Ser Ser
             20                  25                  30

Ser Thr Asn Glu Gly Lys Gln Gln Asp Lys Lys Lys Glu Gly Pro Gln
         35                  40                  45

Glu Thr Gly His Pro Thr Ile Thr Ala Gly Gly Gly Glu Tyr Ser Pro
 50                  55                  60

Thr Asn Lys Asp Xaa Asp Val Glu Ile Ser Gly Arg Ala Thr Arg Ala
 65                  70                  75                  80

Xaa Ser Xaa Xaa Glu Asn Tyr Asn Pro Asn Xaa Gln Leu Phe Cys Trp
             85                  90                  95

Gly Asn Pro Pro Asp Leu Met Pro Ser Gly Phe Pro Ile Ser Leu Glu
             100                 105                 110

Asn Ala Leu Leu Leu Asn Phe Phe Trp Pro Xaa Pro Xaa Leu Gln
             115                 120                 125
```

<210> SEQ ID NO 63
<211> LENGTH: 524
<212> TYPE: DNA
<213> ORGANISM: Zea mays
<220> FEATURE:
<221> NAME/KEY: CDS
<222> LOCATION: (3)...(410)
<220> FEATURE:
<221> NAME/KEY: misc_feature
<222> LOCATION: 297, 323, 351, 354, 390, 404
<223> OTHER INFORMATION: n = A, T, C or G

<400> SEQUENCE: 63

```
gc aat gaa att gtg ctt tgg gaa ccg aag aca aaa gaa cag agt cct          47
   Asn Glu Ile Val Leu Trp Glu Pro Lys Thr Lys Glu Gln Ser Pro
   1               5                  10                  15 ggg gag gga agc atc gat atc ctt cag aag tat cct gtc cca gaa tgt         95
Gly Glu Gly Ser Ile Asp Ile Leu Gln Lys Tyr Pro Val Pro Glu Cys
               20                  25                  30 gac att tgg ttt atc aaa ttt tca tgt gat ttt cac ttc aat cag ttg        143
Asp Ile Trp Phe Ile Lys Phe Ser Cys Asp Phe His Phe Asn Gln Leu
               35                  40                  45 gcg ata ggc aac cgt gaa ggc aaa atc tac gtg tgg gaa gta cag tcc        191
Ala Ile Gly Asn Arg Glu Gly Lys Ile Tyr Val Trp Glu Val Gln Ser
           50                  55                  60 agc cct cct gtc ctc att gct cgg ctg tat aat cag cag tgt aaa tcg        239
Ser Pro Pro Val Leu Ile Ala Arg Leu Tyr Asn Gln Gln Cys Lys Ser
       65                  70                  75 ccg ata aga caa act gca gtg tcc ttc gat gga agc aca atc ctt gga        287
Pro Ile Arg Gln Thr Ala Val Ser Phe Asp Gly Ser Thr Ile Leu Gly
   80                  85                  90                  95 gct ggt gaa nac gca cca tct ggc ggt ggg atg aan tgg acc atc cga        335
Ala Gly Glu Xaa Ala Pro Ser Gly Gly Gly Met Xaa Trp Thr Ile Arg
                   100                 105                 110 gct cca gaa act gaa naa ntg ttg ccg ctc aat gct gga ctg atg gtt        383
Ala Pro Glu Thr Glu Xaa Xaa Leu Pro Leu Asn Ala Gly Leu Met Val
               115                 120                 125 acg ctc ngt tgg ggt tgc can ggt tga atccgttggt ggaaaantgc              430
Thr Leu Xaa Trp Gly Cys Xaa Gly *
               130             135 cacctgggtg ttttttctan tcaaaatggg ttggtgttaa canaatattg naatgnttcc      490
aaatgttgaa aaatttggga tgcttgtgcc tggt                                  524

<210> SEQ ID NO 64
<211> LENGTH: 135
<212> TYPE: PRT
<213> ORGANISM: Zea mays
<220> FEATURE:
<221> NAME/KEY: VARIANT
<222> LOCATION: 99, 107, 117, 118, 130, 134
<223> OTHER INFORMATION: Xaa = Any Amino Acid

<400> SEQUENCE: 64

Asn Glu Ile Val Leu Trp Glu Pro Lys Thr Lys Glu Gln Ser Pro Gly
1               5                   10                  15

Glu Gly Ser Ile Asp Ile Leu Gln Lys Tyr Pro Val Pro Glu Cys Asp
            20                  25                  30

Ile Trp Phe Ile Lys Phe Ser Cys Asp Phe His Phe Asn Gln Leu Ala
        35                  40                  45

Ile Gly Asn Arg Glu Gly Lys Ile Tyr Val Trp Glu Val Gln Ser Ser
    50                  55                  60

Pro Pro Val Leu Ile Ala Arg Leu Tyr Asn Gln Gln Cys Lys Ser Pro
65                  70                  75                  80

Ile Arg Gln Thr Ala Val Ser Phe Asp Gly Ser Thr Ile Leu Gly Ala
                85                  90                  95

Gly Glu Xaa Ala Pro Ser Gly Gly Gly Met Xaa Trp Thr Ile Arg Ala
            100                 105                 110

Pro Glu Thr Glu Xaa Xaa Leu Pro Leu Asn Ala Gly Leu Met Val Thr
        115                 120                 125

Leu Xaa Trp Gly Cys Xaa Gly
    130                 135
```

```
<210> SEQ ID NO 65
<211> LENGTH: 513
<212> TYPE: DNA
<213> ORGANISM: Oryza sativa
<220> FEATURE:
<221> NAME/KEY: CDS
<222> LOCATION: (2)...(505)
<220> FEATURE:
<221> NAME/KEY: misc_feature
<222> LOCATION: 364, 452, 458, 480, 499
<223> OTHER INFORMATION: n = A, T, C or G

<400> SEQUENCE: 65 g tgg aat gtt cac aca ggg atc tgc att ttg att ttt gct gga gca gga        49
  Trp Asn Val His Thr Gly Ile Cys Ile Leu Ile Phe Ala Gly Ala Gly
  1               5                  10                  15 ggt cac cgg aat gaa gta ttg agt gtt gac ttc cac cca tct gat atc         97
Gly His Arg Asn Glu Val Leu Ser Val Asp Phe His Pro Ser Asp Ile
            20                  25                  30 tac cgc ata gca agt tgt ggc atg gat aac act gtt aaa ata tgg tca        145
Tyr Arg Ile Ala Ser Cys Gly Met Asp Asn Thr Val Lys Ile Trp Ser
    35                  40                  45 atg aag gaa ttc tgg cca tat gtt gag caa tcc ttt aca tgg act gac        193
Met Lys Glu Phe Trp Pro Tyr Val Glu Gln Ser Phe Thr Trp Thr Asp
50                  55                  60 ctt cca tca aaa ttt cca aca aaa tat gtg caa ttt ccg gtc ttg gtt        241
Leu Pro Ser Lys Phe Pro Thr Lys Tyr Val Gln Phe Pro Val Leu Val
65                  70                  75                  80 gct gta gta cat tct aac tat gtt gat tgt act aga tgg ctt ggt gac        289
Ala Val Val His Ser Asn Tyr Val Asp Cys Thr Arg Trp Leu Gly Asp
                85                  90                  95 ttc att ctg tca aag agt gtt gac aat gaa att gtg ctg tgg gag cca        337
Phe Ile Leu Ser Lys Ser Val Asp Asn Glu Ile Val Leu Trp Glu Pro
            100                 105                 110 aaa aca aaa gaa caa agt ccc ggg gan ggt agc att gat att ctt cag        385
Lys Thr Lys Glu Gln Ser Pro Gly Xaa Gly Ser Ile Asp Ile Leu Gln
        115                 120                 125 aag tat cct gtg cca gaa tgt gat atc tgg gtt atc aaa tct cat gcg        433
Lys Tyr Pro Val Pro Glu Cys Asp Ile Trp Val Ile Lys Ser His Ala
    130                 135                 140 att cac tca atc aat tgg nat agg nac cgt gaa gga aaa tct tgt cng        481
Ile His Ser Ile Asn Trp Xaa Arg Xaa Arg Glu Gly Lys Ser Cys Xaa
145                 150                 155                 160 gaa tac atc aat cct ccn gtt taa cgcccgcg                               513
Glu Tyr Ile Asn Pro Pro Val *
                165

<210> SEQ ID NO 66
<211> LENGTH: 167
<212> TYPE: PRT
<213> ORGANISM: Oryza sativa
<220> FEATURE:
<221> NAME/KEY: VARIANT
<222> LOCATION: 121, 151, 153, 160, 166
<223> OTHER INFORMATION: Xaa = Any Amino Acid

<400> SEQUENCE: 66

Trp Asn Val His Thr Gly Ile Cys Ile Leu Ile Phe Ala Gly Ala Gly
1               5                   10                  15

Gly His Arg Asn Glu Val Leu Ser Val Asp Phe His Pro Ser Asp Ile
            20                  25                  30

Tyr Arg Ile Ala Ser Cys Gly Met Asp Asn Thr Val Lys Ile Trp Ser
```

```
                35                  40                  45
Met Lys Glu Phe Trp Pro Tyr Val Glu Gln Ser Phe Thr Trp Thr Asp
 50                  55                  60

Leu Pro Ser Lys Phe Pro Thr Lys Tyr Val Gln Phe Pro Val Leu Val
 65                  70                  75                  80

Ala Val Val His Ser Asn Tyr Val Asp Cys Thr Arg Trp Leu Gly Asp
                 85                  90                  95

Phe Ile Leu Ser Lys Ser Val Asp Asn Glu Ile Val Leu Trp Glu Pro
                100                 105                 110

Lys Thr Lys Glu Gln Ser Pro Gly Xaa Gly Ser Ile Asp Ile Leu Gln
            115                 120                 125

Lys Tyr Pro Val Pro Glu Cys Asp Ile Trp Val Ile Lys Ser His Ala
        130                 135                 140

Ile His Ser Ile Asn Trp Xaa Arg Xaa Arg Glu Gly Lys Ser Cys Xaa
145                 150                 155                 160

Glu Tyr Ile Asn Pro Xaa Val
                165
```

```
<210> SEQ ID NO 67
<211> LENGTH: 534
<212> TYPE: DNA
<213> ORGANISM: Glycine max
<220> FEATURE:
<221> NAME/KEY: CDS
<222> LOCATION: (2)...(534)

<400> SEQUENCE: 67
```

```
t aag agt ttt gtt ggc cat gga gac tcc ata aat gaa gtc aaa gct caa       49
  Lys Ser Phe Val Gly His Gly Asp Ser Ile Asn Glu Val Lys Ala Gln
   1               5                  10                  15 ata tta aat cca tca ctc gtg gta tcg gca agc aaa gat gaa tct att        97
Ile Leu Asn Pro Ser Leu Val Val Ser Ala Ser Lys Asp Glu Ser Ile
             20                  25                  30 cgg tta tgg aat gct cat act gga ata tgc att ttg ata ttt gct gga       145
Arg Leu Trp Asn Ala His Thr Gly Ile Cys Ile Leu Ile Phe Ala Gly
         35                  40                  45 ggc ggg gga cat cgt aat gaa gtc tta agt gtt gat ttt cat cca tcg       193
Gly Gly Gly His Arg Asn Glu Val Leu Ser Val Asp Phe His Pro Ser
 50                  55                  60 gat atg tat cgt att tgt agt tgt ggc atg gat agt act gta aaa ata       241
Asp Met Tyr Arg Ile Cys Ser Cys Gly Met Asp Ser Thr Val Lys Ile
 65                  70                  75                  80 tgg tct atg aag gag ttc tgg aca tat gta gaa aaa tca tcc aca tgg       289
Trp Ser Met Lys Glu Phe Trp Thr Tyr Val Glu Lys Ser Ser Thr Trp
             85                  90                  95 aca gat ctt cct tcc aag ttt cca aca aaa ttt gtc cag ttt cct gtt       337
Thr Asp Leu Pro Ser Lys Phe Pro Thr Lys Phe Val Gln Phe Pro Val
            100                 105                 110 tac act gct tca gtg cat ata aat tat gtt gac tgt aat agg tgg ttg       385
Tyr Thr Ala Ser Val His Ile Asn Tyr Val Asp Cys Asn Arg Trp Leu
        115                 120                 125 ggt gat ttt atc ctc tca aag agt gtt gat aat gaa att atc ttg tgg       433
Gly Asp Phe Ile Leu Ser Lys Ser Val Asp Asn Glu Ile Ile Leu Trp
    130                 135                 140 gaa cct aaa gtg aac gaa cca act cca ggg aag ggt gta gtt gat gtc       481
Glu Pro Lys Val Asn Glu Pro Thr Pro Gly Lys Gly Val Val Asp Val
145                 150                 155                 160 ctc ata aat acc cat ttc cga ttg caa tat ctg ggt cat cag ttt tct       529
Leu Ile Asn Thr His Phe Arg Leu Gln Tyr Leu Gly His Gln Phe Ser
```

```
                       165             170             175
tgt ga                                                              534
Cys <210> SEQ ID NO 68
<211> LENGTH: 177
<212> TYPE: PRT
<213> ORGANISM: Glycine max

<400> SEQUENCE: 68

Lys Ser Phe Val Gly His Gly Asp Ser Ile Asn Glu Val Lys Ala Gln
  1               5                  10                  15

Ile Leu Asn Pro Ser Leu Val Val Ser Ala Ser Lys Asp Glu Ser Ile
             20                  25                  30

Arg Leu Trp Asn Ala His Thr Gly Ile Cys Ile Leu Ile Phe Ala Gly
         35                  40                  45

Gly Gly Gly His Arg Asn Glu Val Leu Ser Val Asp Phe His Pro Ser
     50                  55                  60

Asp Met Tyr Arg Ile Cys Ser Cys Gly Met Asp Ser Thr Val Lys Ile
 65                  70                  75                  80

Trp Ser Met Lys Glu Phe Trp Thr Tyr Val Glu Lys Ser Ser Thr Trp
                 85                  90                  95

Thr Asp Leu Pro Ser Lys Phe Pro Thr Lys Phe Val Gln Phe Pro Val
            100                 105                 110

Tyr Thr Ala Ser Val His Ile Asn Tyr Val Asp Cys Asn Arg Trp Leu
        115                 120                 125

Gly Asp Phe Ile Leu Ser Lys Ser Val Asp Asn Glu Ile Ile Leu Trp
    130                 135                 140

Glu Pro Lys Val Asn Glu Pro Thr Pro Gly Lys Gly Val Val Asp Val
145                 150                 155                 160

Leu Ile Asn Thr His Phe Arg Leu Gln Tyr Leu Gly His Gln Phe Ser
                165                 170                 175

Cys

<210> SEQ ID NO 69
<211> LENGTH: 584
<212> TYPE: DNA
<213> ORGANISM: Triticum aestivum
<220> FEATURE:
<221> NAME/KEY: CDS
<222> LOCATION: (2)...(364)
<220> FEATURE:
<221> NAME/KEY: misc_feature
<222> LOCATION: (350)...(350)
<223> OTHER INFORMATION: n = A, T, C or G

<400> SEQUENCE: 69 c cgg agc cgg gag tac aag ctc tgc agc aag cac acc gag ggc aag cgc    49
  Arg Ser Arg Glu Tyr Lys Leu Cys Ser Lys His Thr Glu Gly Lys Arg
    1               5                  10                  15 ccg ctc tac gcc atc ggc ttc aac ttc atc gac gcc cgc tac tac gac      97
Pro Leu Tyr Ala Ile Gly Phe Asn Phe Ile Asp Ala Arg Tyr Tyr Asp
             20                  25                  30 gtc ttc gcc acc gtc ggc ggc aat cgt gtg acg acg tac cgt ggc ctc     145
Val Phe Ala Thr Val Gly Gly Asn Arg Val Thr Thr Tyr Arg Gly Leu
         35                  40                  45 ccc gac ggt aac ttg gct gtt ctg caa gca tac att gat gcg gac gat    193
Pro Asp Gly Asn Leu Ala Val Leu Gln Ala Tyr Ile Asp Ala Asp Asp
     50                  55                  60
```

```
gct cag tca ttc tac act ctg agc tgg gct tgt gac ctt gac ggc aca       241
Ala Gln Ser Phe Tyr Thr Leu Ser Trp Ala Cys Asp Leu Asp Gly Thr
 65                  70                  75                  80 cca ctg cta gtg gca gca gga agc aat gcg gtc att cgg gtc atc aac       289
Pro Leu Leu Val Ala Ala Gly Ser Asn Ala Val Ile Arg Val Ile Asn
                 85                  90                  95 tgt gcc aac cga gaa ttt gtt aag agt ttc ctg ggc aat ggg gaa tca       337
Cys Ala Asn Arg Glu Phe Val Lys Ser Phe Leu Gly Asn Gly Glu Ser
            100                 105                 110 tta att ggg ata nga tcc aac cat tga ancttcgtct taattctgca             384
Leu Ile Gly Ile Xaa Ser Asn His  *
            115                 120 agcaaggaca atctgttagc tatggaatgt caatacaagg tatcngatct tgattngctg     444
ggaggaagaa gtcaccgtaa tgaantattg antgttgact caaccttcng anatcaacga    504
attgcantgt ggaaggtaat acgttaaatc gggcaatgaa aaatttggca nactgganaa    564
tctttaatga cgactcacaa                                                 584

<210> SEQ ID NO 70
<211> LENGTH: 120
<212> TYPE: PRT
<213> ORGANISM: Triticum aestivum
<220> FEATURE:
<221> NAME/KEY: VARIANT
<222> LOCATION: (117)...(117)
<223> OTHER INFORMATION: Xaa = Any Amino Acid

<400> SEQUENCE: 70

Arg Ser Arg Glu Tyr Lys Leu Cys Ser Lys His Thr Glu Gly Lys Arg
 1               5                  10                  15

Pro Leu Tyr Ala Ile Gly Phe Asn Phe Ile Asp Ala Arg Tyr Tyr Asp
             20                  25                  30

Val Phe Ala Thr Val Gly Gly Asn Arg Val Thr Thr Tyr Arg Gly Leu
         35                  40                  45

Pro Asp Gly Asn Leu Ala Val Leu Gln Ala Tyr Ile Asp Ala Asp Asp
     50                  55                  60

Ala Gln Ser Phe Tyr Thr Leu Ser Trp Ala Cys Asp Leu Asp Gly Thr
 65                  70                  75                  80

Pro Leu Leu Val Ala Ala Gly Ser Asn Ala Val Ile Arg Val Ile Asn
                 85                  90                  95

Cys Ala Asn Arg Glu Phe Val Lys Ser Phe Leu Gly Asn Gly Glu Ser
            100                 105                 110

Leu Ile Gly Ile Xaa Ser Asn His
            115                 120

<210> SEQ ID NO 71
<211> LENGTH: 4735
<212> TYPE: DNA
<213> ORGANISM: Zea mays

<400> SEQUENCE: 71
aagcttttgt tttagccaag atttgagatt cgatttgaag tgtggaagtc cttccaattt      60
gccaatccta tatttgatct ctgctgtgct gcgttaaatc cctaaacttc acagcgcggc     120
gccggcccag ccacgccgga agaggtcgcc gcgtgaggtc agtgtccccg ttgctgccgc     180
ctctaacccg aagcctaggc cgctgccggt gcataacaag gagaatcagg cggaggggaa     240
agtagcagag gaggggggcag caactgagga ggggagaag taccgggcgg aaccggaaat     300
cttgccgctg ccgccggcca tggcgaagct gggcccgggg caggggctcg ggtgcgaggc     360
```

-continued

```
ggcggagggg tcgctcgtgc ccagccggaa gcgggagtac caagccctgc ggcaagcaca    420 ctgagggaa gcgcccgcta tatgctatcg ggttcaactt catggacgcg cgctactacg    480
acgtcttcgc caccgtcggc ggcaaccgcg taagccatcg actgctctct cctgtcgtcc    540
tttttttgtt tctactgagg tttggggagt tcttgttgat taatggcaag gtaaaactac    600 gttgttttt tttgtgattt tggtggtcgg ttttaggaag cggtcgcttt tgattcaaat    660
ttgatctaaa gctgaggcat tcggttgttt ttattgggga cttgaggtct gtaatgttcc    720
gactattgtg atttgttttg ccgaaacatg gagtttgcta gttcatttga tgaaaagctg    780
caacctttga caaagaattt gtatcacttg ggaaagtata gtgaggtgtg gggaatcaga    840
tagtaccaat attactttga ctatgattat aagataatct tttaatgtcc tttgtaacga    900
ccatgctgct tttcgcttat cttgcctatt gatcttgcag gtgacaactt accgctgcct    960
tgagaatggt agtttcgctc ttctacaagc ttacgttgat gaggatgtaa gaaagacaat   1020
gctcaatgac aatgcttttg cttgctgatt taatattgat aatattcttt ctctaattct   1080
tgtgacgcct atttacctca gaaggatgag tcgttctata ctctaagctg ggctcgtgac   1140
catgttgatg gctcaccact gctggtggca gcaggaagca atgggatcat tcgggtcatc   1200
aattgtgcta cagaaaagtt agctaaggta atctacccct atatttgtat gtgttcctat   1260
ggtaaacttg aatgaagcct tatttgcata attcaatatt tcagttgttt atttgacata   1320
tatcacttta tttatgatat ctgatccaga aggtcttttg gatttgcttt agttaaggaa   1380
tggtgcttgc tacgcattaa taccataagc aaactgtacc ttttgctcac agaatattgt   1440
taattttgac tacttcagta tgtccgttgt agtaaaaaca aatcaacttg gtgtatctat   1500
tttttccttg cttatacata gccaggagat tgggcatgtg gcatgtcaat aaatactatc   1560
ctataccatt tgataggaca cgcactgtgt cttatttggt agctctgttt acgtgattct   1620
gcagagcttt gttggccatg gcgactcaat aaatgtgata agaactcaac cgttgaagcc   1680
ttcgctcatc atttctgcaa gcaaggttat gcgatagtct gttcttaggt tcatgtacct   1740 ttttatttt ataatctttc tgaatttttga caccatttca tatggcatta tctaatagga   1800
tgaatctgtt aggctatgga atgtccatac agggatctgt atcttgatat ttgctggagc   1860
tggaggtcat cgcaatgaag tattgagtgt tgtaagtagt gcctgctatt atgacattgt   1920
gcccttcaaa aaaacatta ttatgacatt attttttagaa cattactagg ttaaggtgcc   1980
tttaatatgg cgcactcttt cagctcctga tattaccatt tgttattgag cgttacatca   2040
gagataaaat aaggctacct aatgactgct actgcttttg tactttgatt acattagtca   2100
taaatgtact gatgaataca ttattttgtc ttaaggactt ccatcctagt gatattgaac   2160
gttttgcaag ttgtggcatg gacaacactg tgaaaatctg gtcaatgaaa ggttagaaag   2220
ctacttcaaa gttgcttcat atttgcatgt tgcgtgtcat tgagttcacc aatgttgtcg   2280
cagaattttg gctatatgtt gacaaatcat attcatggac tgaccttcat caaagttcca   2340
caaaatatgg ccagtttcca gtatgtttca caatgcctat atccaattat cctggcaagg   2400
tcctgttggt gtctaatcct catgccatca gactgacctg tttcttttgt ttcaggtct   2460 tgattgctgc agtacactct aactatgttg attgaacaag atggcttggt gacttcatcc   2520
tatcaaaggt gaaatttctg attcgtttaa atggatacaa atttctgtag cacggttgtc   2580
actcttttgt gggtttgaca tgccactgtc ttggttcatc tattgctgta ccgtgcaagt   2640
gttcagtttt tcaatctttt tttctcagtg cttaatgagg ggagattcta tttgcagagt   2700
```

```
                                                        -continued gttgtcaatg aaattgtgct ttgggaaccg aagacaaaag aacagagtcc tggggaggta    2760
attcagttta actttcccag aattgtattc ctattataat gccatatatt tacgcacagt    2820
tgtaaactat ttccagatcc ttagatttca aggtactggc tgccaatatt aaatatgttc    2880
cactgaagta atatgatttt ctgttgcctc atagggaagc atcgatatcc ttcagaagta    2940
tcctgtccca gaatgtgaca tttggtttat caaattttca tgtgattttc acttcaatca    3000
gttggcgata ggtaatatct ctcatcagga ttgtttctgg tagaagtttt atttaagatt    3060 tttttttgctc tgtaaaattt cacacacgca cacatgcacc cccacacaca cacacatgca    3120
cgcacacccc cacccacctg cacgcgcgcg tacacacaca ccgcacacat atatatgact    3180
ttttttccca cacaaatatt tgctgtgtga gatatcagca aataaattcg tatgtttgat    3240
tatattcaga gatataggaa aattgagtgc tctaatacccc catccactac ttcaaacagg    3300
caaccgtgaa ggcaaaatct acgtgtggaa aaatacagtc cagccctcct gtcctcattg    3360
ctcggtagtt ttcactggaa gagtttcagt tattcttgtc tcccacttgt atcgtcgcat    3420
gcttctggat gccaatgctt catcattttc aggctgtata atcagcagtg taaatcgccg    3480
ataagacaaa ctgcagtgtc cttcgatgga aggtacctca ctctaatcca tgctcaattt    3540
ggtgtactgt ctattctagc acttgctttt ttcttggttc tgcttgagaa attctcgatt    3600
gcatgtcata tgctggtgca ttttcttttt tctgtttccg tggcggattg gtaaaatgcg    3660
acgatgcctt ccttatctag cacaatcctt ggagctggtg aagacggcac catctggcgg    3720
tgggatgaag tggaccatcc gagctccaga aactgaagaa gtgttgccgc tcaatgctgg    3780
actgatggtt acgctcggtt ggggttgtga tggttgaatc cgttggcgga aagtgccacc    3840
tggtgttttt ttctagtcaa aatggttgat gttaacagaa tattgaatgc ttcgaatgtt    3900
gaaagttggg atgcttgtgc tggtactctg ctccgcggac gagtgaactt agtttgttgc    3960
aactttggga accgttgtca tctgtttgtt ctgcatttct aaaaagagag caaatttcag    4020
gatacatgtt ctttttttttc agtacaggaa aactaaggtt gaggtattgc tttgcaattt    4080
actctctctc tctctctctc ttaaaaaaac tggatcttgc ttcaacgatg cattccttgg    4140
gtcatcggtt ttacttttga aatcttgata gctgggccta aagttaccaa gcccactagt    4200
atcagaagta ataatatgat ggctcctccc ctgccttact gtcacgtgta aactttcgaa    4260
actagcagga ctgtagcatt tagcgagctg gttgtttggg ttagagctca gcgtcgcaac    4320
ttatggtacc gaggtcagtg tcaagatcta tggcaccatg gttcaatcac agttttagtc    4380
ccaccaaaaa tataaaggtg aagtttcgac aaaaaatggc tagaataaaa aaaaacaggt    4440
ccacatactg aggagaacac atgacagatt caccaaggat tttgaattga agaggctaa     4500 tgattgacag gatttgatct tcaattccac ctcccgttgt cctgcttcta ctctaaagtt    4560
caagcgtggc tcagtttggc tatctgttat aatttcaaga aatcctgatt tctgttagca    4620
gtttactagg ctattaggag gagctgggac aaaagaaaaa cgagaattga cgaggacaaa    4680
ttcgcaatta gttgggaaat tgggggcaca attttcaatg cccacaaaat tcact         4735
```

<210> SEQ ID NO 72
<211> LENGTH: 7525
<212> TYPE: DNA
<213> ORGANISM: Zea mays
<220> FEATURE:
<221> NAME/KEY: misc_feature
<222> LOCATION: 5878, 5975
<223> OTHER INFORMATION: n = A, T, C or G

<400> SEQUENCE: 72

-continued

```
aagctttgag acttgatttg aagtattaaa taaacccttc aaatttcttt ctaactttga      60
taatacacta ttcaatgaca atgcacttcc ttaaatccct atacttcaca gcatgccgcc     120
ttccaaagca cgccgaaaga ggtcacttcg tgatatcact gccaccgttg ccactgggcc     180
tgttgccaac tcgaaacctg gctcatcatc gacgaacgag gggaagcaac atgacaagaa     240
aaaggagggt ccacaggaac cggacatccc accattaccg ccggtggtgg tgaatatagt     300
cccacgacaa ggattaggat gtgaagtagt ggaagggcta ctcgtgccta gtcggaagcg     360
agagtacaag cccaatagca agtatactgt gggaaatcac ccgatctatg ccatcgggtt     420
caatttcatt gacatgcgct actatgatgt ctttgccatc gccagttgca atagtgtaag     480
caaccgactt ctccctacct cttgtttgct atccatttat cctattgagg tttggggagt     540
tctatatggt gaacgaaaat ggaagttatg attttggtgg gattggatct tggtttataa     600
ctagaaaagg atttgagtac aggttatgat gtgtggcttt atggtaggga aacttaatat     660
cttttcctat tttgtttttt ggcatcacga gtaatggttt gggaaataaa agggaaaatg     720
atttaaaatt atttctcaat agagcatgcc cttttacata gggacatttt agtcattttta    780
cacacacttt agtcattttta cacaccgtaa ttatgtcaca atcaaagaat cattccttgg    840
ttcaattgaa tgagatgatt caactagttc acatctctat acctaacaat atagttttttc    900
ataactagaa ttcttaaaaa gaattaatat gaacctaaat attatttcac tttcttgccc     960
cttataatat aatacatttg tcactcccat tttggcaagg gtggtgggta ttttggggga    1020
tggaatgtta ctattttttaa tttgattaga agctataagc tttggctata tttttattag    1080
gaatttgatg ttcattttca atatattgtg atctattttc ttaaaatgtg aatttgttgt    1140
gtattttgat tagttcgatg aagagtgttt ataagatatg atttttaaat tctcttacga    1200
cgaaacaata ttatgttact ttcatctatt catcttgagg aatcacctac ctcacttctt    1260
gatcttgcag gtgataattt accgatgcct tgagaatggt ggttttggtc ttctacaaaa    1320
ttatgttgat gaggatgtga aaagacaat gcctggtgca tgtggttgtt aatgttaatt    1380
tgataatatg cttttatcta atgtctgtgg tgcctattta tctcagaagg atgagtcatt    1440
ctacactcta agctggacca tcgatcaagt tgatagctca ccgctgttgg tggccgctgg    1500
aagcaatcgg atcattcggg tcatcaattg tgctaccgaa aagttagata aggtccctgc    1560
ccctgtgctt actctatgtt tgtatggaaa agttgattga acgttgatgt tcacatatca    1620
atatttcagt agtttagttg aaatacaatt tatttatgct ctctattctt gaacatcagt    1680
tgactttgct ttgattaagc aatggtcttg ctcatacaat attctaggag ttgaatattc    1740
aatatgcctg ttacatgata gcaaatacat agtgaactag acatgtact aaatattttaa    1800
tttcccttta tgacattctc tagagcttag ttggccatgg tggttcaata catgagataa    1860
ggactcatgc ctcgaagcca tcactcatca tttctgccag caaggttagt aataaatttg    1920
tcgtgtgtcg attttttttac acttttttaac atgacattat tctataggat gaatctatta    1980
ggctatggaa tgtccatact gggatttgca tcttagtctt tgcagggct ggaggccatc     2040
gacatgatgt gttgagtgtt gtaagtatcg attgcatctt gtctagacat tgttttaaat    2100
atcacttgcc ccgaagataa cactcattag aattctaatg ttaccatttg ttattgagca    2160
tgccaaattt caatttttaac atcatagata aaataagacc ccacaattac ttttactgtt    2220
tatctacttc cattcatta ggcataaagt tactgataaa aaagacaatc ttttatctga      2280
aggacttcca ccctaccgag gttgggattt ttgcaagttg tggcatggac aatactgtga    2340
```

```
agatttggtc aatgaaaggt ttgggaacta cttaaacta gcttcatgtt tacatttgt    2400 gttgtatgtt gcatatcatc gacaaatatt gccaatgttg tcacagaatt ttggatatat    2460
gttgaaaaat catattcatg gactggccat ccatcaaagt ttccaacgag gaatatccag    2520
tttccggtat gttaagtagc tataatcacc tgagctcctt tcttttttg caaactattg    2580 ttggtgttca gttttcatgc cattcaagca tacatgtttc ttttctttta ggtcttgact    2640
gctgcagtac actctgacta tgttgattgt accaagatgg cttggtgact tcatcctatc    2700
aaaaggtaaa ttcttcattt gttaaatggc tatacatttt tttataaagg aaattttta    2760 ttaatttcaa gcactttaga ttgaaataat acaaatctt aaaaacatt tttggcctcc    2820 atttaaacaa gcacaaatcc aacaaaaatg agtaaaccaa cccattctag tgaatattaa    2880
tgcataaact agattgctac ccatatgtct agaaaaagta gccttgaccg cgtatcttaa    2940
ttgtcaccat gccgccacaa ccaaaccgtg caaatatggt ttttggagaa tggaccaagt    3000
aagaaaccaa tcaataattg agtatatagc atgcacagga gaaatagatc tcttatttc    3060 aagaacaatg gtattttta ttaaccatag gaccaacaag tagcgactac ccatagcaaa    3120
actaatggct tcagattatt actggttgtt gaagtgtata cgtggtttgc ctactttctc    3180
ccaatagttt aagcttttgg attgaatcga ttagtgcgtt cactcttaca tggtatcaaa    3240
gttagcaatt ttgggtttga atcctaacgg aagctttatt tgtgacttca cctcttgttt    3300
tccattccct ttctacctgc acgtgagtgg gggtgttgaa gtgtataagt ggattgccta    3360
ccttatcaac cttttggatt aaactggtta ttggttagtg tgttcactcc tacacctaag    3420
tatgaggttt agttatccag tagccaatta gattatgcac agtggacact tcacatgtgc    3480
aactagcact caaaacataa gtctttaatt gtctcatctt atgacaaaac aacatatttc    3540
actaccattc tataacatct tgatttgtac atcagtcttg ttaatgctaa atagtgagat    3600
ttgatcgtca attggccagt tggatgtaaa ttccagtgaa atacatcttg accttgggtt    3660
aaatggacat tagcaatgtg tgggaacaaa ttgttggttt gggtacacca aactgttggt    3720
ttttaattag tagattagtt tgtaacacat ttccttttat cagtgttagt attggtttat    3780
tatgcatagg gaaggatctg atatgtgata attaacatgg atttgcagag tgtaaagaat    3840
gcagttttgc tttgggaacc aaaaccagac aagcgtaggc ctggggaggt gacacgcttt    3900
accttctcgt cccgaattct gcacctattt ttatattact atcatactca tctacagttt    3960
aaaacttgtc ccgcaatctt ttcagttct gagcactaaa tttataccct tgaatcagta    4020
tagtcgtttt ctctttgttc gtataggga gtgttgatgt tcttcagaag tacccggtgc    4080
caaagtgttc attatggttt atgaaatttt catgtgattt ttactccaac cagatggcaa    4140
taggtaatgc ctttaatttt gtgaagactg ttttggcact aaagctttac gtacgtaata    4200
ttagttttat atcttgtaca ttgatggaaa atagattgct caatatctat atatatgact    4260
atatcttggg ttagattcta aggaacaaac tctcccagag tacggttctg aataacaacc    4320
atctgctgct gctgcttaat gcgaacaggc aacaataaag gcgagatcta tgtctgggaa    4380
gtgcagtcca gcccgcccgt cttaattgac cggtaaattt ccagttcttc tcctcctcgc    4440
atcggttcct gcatgggtag ctagctagta actccgacgc ttctgctgga tgcaaacact    4500
tgtgcatttt caggctgtgc aaccaggaat gcaagtcgcc gataaggcag accgcagtgt    4560
cattcgacgg aaggcacgta cgcactacga ctctcactat ctgctcatgc atgcattcac    4620
cgcacgtacg tgtgatgtgc tcgctcgctt cctccttttg tgatggtgtc tctctcactt    4680
gcccagcacg atcttggagc cgccgacgac ggcggatctg gcgcggtggg acgaagtgga    4740
```

```
ccctgctgct tccagctcca aacctgatca agctgctgcg cccgccgccg gtgcgggtgc   4800
cgacgccgac gccgacgcct gagcgagagg accgtcgtcg cccgccggtt cacatcgatc   4860
gtactccgtg ctggctgatt accttaccc attgggatgt tttggttcag agtcgccaga    4920
tctagtgtgt ggctgaacgt tgaatgttag gatgctgctg cttgttatgc tctgagtctt   4980
gagttctctt tgttaatttg caccgtggat gagatgaata acttgacgtt gcaactttgc   5040
atcccatata tgccgtaaat ctgccgtctg ttgtttgttc tgcgttgtct agaattagtg   5100
gagatgtgct ggatacaatg tatgctagtc tattaaaccg tgctccactc tgagataatc   5160
gaccaacttg tcttattatt gaaagaactg tggaaaaaac caaaaaagt cgttgtggtt    5220 ttgtttatta tcaaatatat tttacataag acttaaaagt tttcattttt tcatgaattt   5280
tttgaataaa ccgagtagtc aaagctaggg tcaaaaggc aaacatatta tatttaaaa    5340 tggagagaga gtacattgtt ttaagacgaa ttgtttaata caactcgaga atattctgat   5400
acattaatcc tatgatatta ccataaaaaa cattaatcct atgatagagt gtataattac    5460
aaatgcacaa aggttctttt catgtgaaat cgtattatag atagggtca tagcgcgccc    5520 ttgtccctac aacttacgat gttcatgagt taggttagaa aaaggttaga gcaagtatac   5580
taaagtgaca tatgcaggct acaaggaatg ccacatcaga tttttggtga cgttgaagga   5640
agaaaaatag agggagaaaa aagcgaacca attgcgaagg tgccttcttc caagggcacg   5700
gtccatggag tgtggtagcc gacatcaagg tagaggatta tggtaaagtt atttgagcaa   5760
gtgtctgaca actagcatga aggcttagga ttttctaaat gcatctttga gcgctattga   5820
tgtagatgtt aatgattttt agggctgatg accaaaccaa agatgaacat gggaacgnaa   5880
ggaaggttac tgaaagtgta taggcccta gtttagtctt cagtgactaa tgataatata    5940
tattattgtg actaacaagt gttttataga aacanggaaa gttagatcac aataatagat   6000
atgatcagga ttattatgtg gtacccatcc cttattgatg aaaatcaatg gttggttctc   6060
ataggataat cgaaaaggtt aaggatcaac tgtaaatgga gttgttggac acttagagta   6120
gtgatttgac ctttttctt tggtagtact ataaacggac atgaaatgcg tagctttacc    6180
taaacaagtc tagttaagta tgatgatgca cacttgtgaa tactagtgct aggtaaaccc   6240
atgagatctc atgtgaagtt cgaaacaaaa cctaattcga aaagtgatta aaacatgtga   6300
cttaacaatg ttgtagtagc attggtcgag tttgatgggc acctgatatg ggtcactaga   6360
catgagtgtg ccctgttgtg tttgagtgaa gcactagcat atcaggtgtg caacagatat    6420
ggtgcaccca ggcaggacac ccaaagagct tgcaaaatta gcctaaaaca cttagtgctc   6480
accagacata tctagtgtac tactagttat tctcgttata tatgaaccct attagttatt   6540
cttgaattgc ttcgatcttt tacaaaggaa gtagttttc cttcatctcc ataaactgtg     6600
gttttccaaa ggcattaata ataagattta gtatattaaa ttcaaagttg aggtacttta   6660
ttatcgtgaa accaacatta atactataga cttaactaag gagtctattg gtgcttcctt   6720
ctcatgtatt ttcttcttga agtgttcctt catcttggtg ctaacgacga cattcaacaa   6780
tgtgtgctct tacttgattg gttgtatat atggtggtgt tcctttactt agtggcaaca    6840
taccttatcg ataactaacc cttagtgaaa gaaatgaaaa tgtacatccc actgggaaat   6900
cactcatacc cctaagagct aacttaatgg aacatcactc atagccctaa gggctagttg   6960
gaagtacttt ctcatttcct gtataagggc tagttcatga ttcaacttct tctccatttc   7020
ttggtgaact atcttagcac gattcctata aaaacatata caactaaaca aagggtggtg   7080
```

-continued

```
gtactgaaca cagtggaccc aagcactcgg aaatgggaag gacaagttgc atggaaaaaa      7140
cgacaggctg ggaactattg tgtcttgtca agcgtgttcg tccagctata ggacatgggt      7200
atttataggg caactagagg ttggtatcct aaaatatgtc cagaccccta gttatcaact      7260
acgttcctag ataatactgt acaacaaggt aattatagaa tagtaagttt gttattctaa      7320
ctccaccccg acaggtgggt ccgttgtcgc ccggttgaga gtgggccctg ctcggccagg      7380
tcattggcat tgtccgtgca gacgtgttcc caatatcgag gcaatgaagt tgtttgacac      7440
ttcttcggga gtcggcgtga ggccttcgct tgctagcgcg aacttgccca cgagcgtcct      7500
caccatgggc cccgctgaca agctt                                            7525

<210> SEQ ID NO 73
<211> LENGTH: 5506
<212> TYPE: DNA
<213> ORGANISM: Zea mays

<400> SEQUENCE: 73
ccgatcattc gtttgttcga tcatttgatc gttcatcgtt cgttcatagt tcctattcat        60
cgttcatcgt ttgttcatag tacttattca tcgttcatcg ttcgttcata gttcctattc       120
atcgttcatc gttactattc atcgacacta ttcaccatcg ttactattca ttgttactat       180
ttaccggctc tattcgtcat cgttactatt catcgttgct atttatggta gcttttttcgt      240 tgttactatt catcgatcat ccgatcgccc caaatttcaa ctactcatcc atcatgttgt       300
ccagtccacc taagaccagc cagacccata ttccagtcat acgaactcct gtgattgtga       360
ttttccttcc agtagggaac ctcccatctg gtcacccatc ctaggtttct ccaagttgag       420
catgcttaac tttgagattc ctttgaacca ggcttccaaa ctcagattcc aataattctt       480
gtttctaaat tcttatcaaa ctattcccta tccaaccatg tcatccctta agcctggtcc       540
atattccaga aaactcccaa aatactcttg tcccatattc tgcatataac tctcctgttc       600
atactaagtc agacgattca ttcgtcacta ttctcaccaa cagtgaactt cactgtgcta       660
caccacatac actcagctat aaatacaccc agctaccctc tccctctcca cacacactca       720
acaccctcag ccaaggcaaa cacctcaccc actcagttac tccgctctac cggctacacg       780
catagtgtcg cttcgcctcc agtccaccct cctggtaagc acctccgctc caccaccagt       840
aatatcacaa caccacatga cacagattct actcaagact ctacccatcc atatatcgct       900
attctgacca ctatactaaa tatttgttgg tatacttgct ggtttgtatg tttgcttgtt       960
catgttgcat agttatcgga gcgttcgtgc catcacgtgg aggccagatc tgcaagtcta      1020
cgccaggcgg tggagccaga agccagttcc gcgagctctc cttccccctt cactggataa      1080
gcacagcaag ctcactggat ccctttgatg cataaattac ctatgatttt tcaaccacaa      1140
ccctcagcct gttattttat gcataatatg atttttgagac aagttattat ggccacccag    1200
ccgcttgtcg caatcaatcc ttgatatatt tgttacaaat gatttgagaa aaggtgtgag      1260
ttttcaaaag aaaatgcttt tcaaaatgtg tatgatgaag ggttttcacc cttatcacct      1320
tttaataggg atgatcaagg actccctggt ttaggggagg gcctaaggtg atggctcagc      1380
tggtttaggt gtgagcagaa ggattgtccc ctcacataag gaccgatttg tcatccgtca      1440
ctacctgtac tcatgataag tacaaccact cgagactgta tgggcaatca ctcaatctga      1500
actcgtacgg tccaacccta gggttatgaa ggctgggggag caccgggagg ataaggaggg     1560
agaatgtttt gtccggtttg gacatggcgg tggcctgact ccttccggta taaccgttaa      1620
ggtaaggacg tgcgaggaaa gaaagagatc cggcattcgg gcctcacgac ggtgagatcg      1680
```

```
cagaaaccag actagtgggt aaagtgtacc cctctgcgca gagtttgaaa acctattcga   1740
atagtctgtg tccacaggaa tggacgagtc tggtgtggta tgacaattag tgttttgttt   1800
tcaaaaaaga atgtgcgttt gagaaaagtg gttttttaaa ggtccggcgg ttgagccgtg   1860
agctatggtg gacgggaagt ccagtagctg ttttttgaaaa cgaaaaccag tgggaaactg   1920
ctgagatacc tggatggttt agtccagggg attttgttct aatattgaaa aaaaattctt   1980
gctcctttgg gagaggatgc gctttgcaaa atacaaaatg ttttacaaaa taaccctgca   2040
taaaatattg ttgtttctgc aaaatatcct gagctccaca tattccatgc attatatctg   2100
atttccccat tccgcgggtg atggtgggct gctgagtacg tttgtactca cccttgctta   2160
tttgttgttt ttcaaaaaaa ggagatcggg taagagttac gactgttccc aaccttgcct   2220
gtggttgttg gaccgctgat ttgcttcgct gcgtatatcg ggctgcttca tccccactct   2280
gatgatatgt cccaagttgt ggaccaactc ttaaagttga tcgccacctt tataggtttg   2340
tctcgtttaa gcagatctgg aatcatttga tgtataaatg tgtttactag cctcctggga   2400
ctagtaattg tatcacattt gagtcctaga ggatcgggac gcttcaatga tcaatgggtg   2460
gatcacaata gtcggttata atggctatat caacagttat aatcacatta aatgtgtcat   2520
cagatgttag ataaagtctg tcgtggatga tctgtttgtg cttctcgacg gtccatgagt   2580
gacgctaaaa ttcattttac caaacctagc accttcgagt tggtctgatc ttgaatagtc   2640
agacggttca cgactgaggt tgaacgatcc acgcaaggtg ttggacgata ctttcttttt   2700
ctttggatgc tccgtagtag atgtgtcggt tttgacatag ttcctgtccg aactccatac   2760
agtccatagt agatgtgtcg gttttggtac tctagacggc ccgagtcagg ggtctggaca   2820
gtcctggact tgctgagttg aggtttgatc tttctttagt tatttcttac ataccctatgt   2880
tcatacactt agcaaactag ttagcttcac caaaacaagt gtggaaaaag gttttaggc    2940
caatttccct ttcaccttta taactaccta gttacaaagt agagtttgat agtccctaag   3000
tatgtcaatt cacatcttga gtacatgcga caatctcatg tctaaggata catggtacag   3060
gttgcaagaa gaaaattgtc acaatatctc atgttgggtc agtacagact catgtcatac   3120
atgcacccat attattagtt ttacatctcc atgtccatga cttacgaaac atagtcatca   3180
actaatacat atgatagtca ttgactctaa ctagggacat cttctagaac aaccatacaa   3240
gaaaagagtc tcacaaacaa ttcacataat tgctaatcaa tacaaggtgt ccttcacaga   3300
tattcaatta aacaatatat catggatgca acawaatatg ctcatctcta tgattatctc   3360
tagggcatat ttctaacaca atgacatgtc taagtgtagt atgtcaaaac atggatagta   3420
atatagatgg taagaggtca ttttttattaa tataattaac aaagatagat agggtgacca   3480
atttttgtaaa agcaccattc atagactttt agtgggaggt ggatgctcta cccgcctccg   3540
taaagccaaa gtggttgcat gcaaattgyt aggatatagt aatgcaagga accaagctaa   3600
ggcatgtaag tgaaacccaa acaagaagtt aagaagcttc caaaatgaac aaagtacaag   3660
aatgaagcta aaagagaaac tttcagcctt ctccaatctc cagcaagatc ccttcgatag   3720
atggtatcta atttttttcct actatgaaaa cctatatcac ctagtagaat agaggacaaa   3780
gcttacgcct actatatata tccaatatgt atagttagat actaagttct tttttctctt   3840
ctcttcattc acttttcaac taggtttgga attaagtttt tggattggca tagacaatgg   3900
catggttgta taggtgttct taaccatcac agttatgagt ttgacttgtt ttttatattc   3960
aagttacaag gtcattttgt gctagccaca gcctagcaat cgaggggcta cacatgtgga   4020
```

```
ttaaggacaa ggcccaaccc atgtacgatc caaggacacc cttgtaattt ttatactcat    4080
caaggattag ggggaaataa ctcccttcta tataaaggtc tttccacttt gcttctcact    4140
ctcccttatt aggttaaaca caaaatgtgc atcgccgccg ccaccatata gaaccactta    4200
tcacgaaccg ccgccatcac atccactgcc tcaactagtg ttaccaccta tggttcattg    4260
ttgtgtctgc ttcttgtagc actgttggtc tacaaacatt catatttctc tcaacatctg    4320
gcacaggtaa gcccataagc cctaacccta gatctccata tttagttatt tcagttcttg    4380
atgagcaaat atgaaactaa attagtttgc taataagaaa tttaactact tttcctcttg    4440
aagacctcct atccctatat gaacccacat ccaaaacccc tctagcaaag tgtggctagc    4500
tttcccatgc catgaacctt caacaatgat agtatcagta atgcacttcc ataaaagggt    4560
tcatatttaa ttttagtttt tcttttttggt gttttaatta agctttgaga cttgatttga    4620
agtattaaat aaaccttca aatttctttc taactttgat aatacactat tcaatgacaa    4680
tgcacttcct aaatcccta tacttcacag catgccgcct tccaaagcac gccgaaagag    4740
gtcacttcgt gatatcactg ccaccgttgc cactgggcct gttgccaact cgaaacctgg    4800
ctcatcatcg acgaacgagg ggaagcaaca tgacaagaaa aaggagggtc cacaggaacc    4860
ggacatccca ccattaccgc cggtggtggt gaatatagtc ccacgacaag gattaggatg    4920
tgaagtagtg gaagggctac tcgtgcctag tcggaagcga gagtacaagc ccaatagcaa    4980
gtatactgtg ggaaatcacc cgatctatgc catcgggttc aatttcattg acatgcgcta    5040
ctatgatgtc tttgccatcg ccagttgcaa tagtgtaagc aaccgacttc tccctacctc    5100
ttgtttgcta tccttttatc ctattgaggt ttggggagtt ctatatggtg aacgaaaatg    5160
gaagttatga ttttggtggg attggatctt ggtttataac tagaaaagga tttgagtaca    5220
ggttatgatg tgtggcttta tggtagggaa acttaatatc ttttcctatt tgtttttttg    5280
gcatcacgag taatggtttg ggaaataaaa gggaaaatga tttaaaatta tttctcaata    5340
gagcatgccc ttttacatag ggacatttta gtcattttac acacacttta gtcattttac    5400
acaccgtaat tatgtcacaa tcaaagaatc attccttggt tcaattgaat gagatgattc    5460
aactagttca catctctata cctaacaata tagttttttca taacta                  5506
```

<210> SEQ ID NO 74
<211> LENGTH: 6408
<212> TYPE: DNA
<213> ORGANISM: Zea mays

<400> SEQUENCE: 74

```
tttttcacac cgttactgtc atctaacaga agcaggtaca aacttgtttt tcgttttcaa      60
gtcgaatttt gagggcaaa ccatagttgc acttccatcg agggacaaaa acacaattgc      120
cccttaactt atatagttaa atatagttaa cgagcttgct actgagacta acaagtcaaa     180
actattggct tgaccttata ttagttttgt cttacacttt acaatcgttg atggctgctc     240
tagatcttat aaacttaaga atattatgac tttatcactt tatttgtaat ggatgtatgg     300
atactcattg atgcattatt tatggtataa actatagacc atgaatgtat ggtgtaatgc     360
tatagtatat tgttagactt gtgtacatat atattattta tacttaactc acaaacttaa     420
tgagtcagct cgaacttata aacgacctga gtcgacctgg ccttatggct tgttaagata     480
acaagtcaaa ccaagccgaa ctgactcgtt atccaaatct acacttacat aaacaaaaca     540
tgatttcaaa ttaagattgg tacaaaagtg ttttgtttta ttcaattaaa ccctacactg     600
tactctttat gtcaacaata gttgatgcta cgacaaagca atgaacattt tatggagtag     660
```

```
ttaatttat  tgtcctaatg  tcaattacta  ttgttagcca  aggaatggag  taagccaata    720
aagagtacat  atctacgagg  aaatttagat  atgtgcgtaa  ctttttaat   cgagatacaa    780 aatgtgcaaa  ataagggtcc  atgtaacata  catatattc   ttgttttat   ggtaaaagag    840 tgtataaact  ataaaggttg  ttgcttagaa  gcgggattta  ataacatcgg  ttttatatta    900
accttaagtc  cctatgcaat  acctgtattt  ttttctaagt  acatggtaca  aacacaaata    960
cacacattta  agcacacata  ctcacttgct  atgagcacac  acgtaaac    cctactccta   1020 ctagcacctt  caaaagacaa  aatagataaa  tcttgttgac  aaagtctatt  gaaaaatatc   1080
aacgtccggt  ctaaatcttg  acaaaatatt  agcacttgtg  ccaagttaag  aagtgagcac   1140
ttgaacgtaa  gtggttagag  gaacctaacc  aagttagtta  tgttcaattt  ttcatgcaag   1200
ttagcttgct  agtttttcta  tacacaaaca  ttatattagc  ttataccatt  gttgggaaat   1260
tctaacttta  atgatttctt  tgagaaatcc  ataagagcga  taaagaggag  agagagagag   1320
agcaagagat  ttgtacatgt  ataaatacta  tccattttct  atttaagaat  ctagacaaac   1380
tagcaaatat  aaatttgaaa  cataataaag  atgggcacct  ggcatctcct  ggatattaaa   1440
agcgtaccat  taaagatata  cataattatt  cacctcttct  aggtataaat  taccctacta   1500
ccacattccc  ctatctctac  aaactctctc  tcattgactc  atcaagagag  tgccacctct   1560
atctctcctt  ctctcttttc  aaatgttcta  caattatcaa  ccatcataca  acattcacct   1620
ttcctaccaa  ccttgttgat  gcttgtctca  actttctctt  tacctagatc  actcatatat   1680
atccctattt  caaaggcatt  aatcatcaaa  aacctataga  aaaatcccat  tatcaaccat   1740
gatggagtct  gatcgtgaga  acaacagtc   tcatggcaag  aaacaaggtg  accatggtag   1800
caagatgcat  gattctgatg  gcaataaaaa  tgtgtcagat  gaaaagagtc  aagagtctgg   1860
tggtaaggaa  cacaaatcca  atataaagaa  acatgaatca  cgtagaaaga  ggtaagacat   1920
tctccttgaa  atcttggct   tcaaactcaa  gttaaattta  tgtacacatg  tttatataga   1980
gtctagagat  tttgtgctta  atatatgcat  gcacatgagt  tcaaataatt  tcataataaa   2040
aataaaaaaa  tcaatatgat  caggaattaa  accatgaaat  ttttagagac  atcatctaga   2100
ttgagttcca  tggtcatacc  atgatggtta  tgtcatttct  ttccaatata  aaaaattcct   2160
taacttatac  tcaaaatgtt  gattggatgg  aactttttct  atagaattcc  ttgccacatg   2220
ttgtgtaaca  accatttgta  ttggtttgcg  tctagtccac  ttttgtgtgt  tgctattatg   2280
taaataatta  ttttttcaaat ccaaagttgt  tcctccacat  atctagaata  tattctaatt   2340
ctacaagaat  ttaaaatgaa  ttgttaactt  aagaatgcat  tgttcaatat  atttatgcat   2400
tttctcccat  tatgatatat  atattctcaa  tatttggcac  ataataactt  ggaacattcc   2460
ttacatttgt  tgggttgagt  gctatatgtt  tggattcatt  aattatttac  attgatattt   2520
ttgtagatgt  ttgtgtttac  ccaataagaa  aaggccatta  agaaaataaa  atgttattag   2580
atagagttag  tcttgacatg  ttatattctt  ttaataattg  gattttgtgg  tatttccaac   2640
acattccttc  catttaaacc  taactccatc  tctcttatct  tcctctatca  tataccttat   2700
cttctttcta  cactaacact  aatgcttatg  tcactcctaa  ccttgatgca  acctaccaat   2760
agtcaattac  tgttacgttg  ctagaaccaa  agattggtcc  attggtgcac  aatccattag   2820
ttcctccttc  ttgggactct  tcaaccatcc  taactcccca  aatgatttca  aaagttttcc   2880
ctaccatgtc  atcctactcc  atatccaatg  tctactggtg  ctagattcta  tctactgtta   2940
gcaccaaact  aaccacaaaa  taataatccc  tacaaatata  ggtggaggtg  atgtaaaatt   3000
```

```
aagggaggggg caattgtaaa tggtagtacc atagatatca aaccttctca acttagagct   3060
atgtctacat agttctagtc ctatgaagca tcaaccattt tcttactaaa ctaaatattt   3120
ttagaggaag gggtggatcc ttactttcat ctccatgagc ttccacccct tcctatgagc   3180
ttatccatcg actgaaagtt cctcattgct ggagcttacc cgttattatc ccatgtcatc   3240
tgacttttgt atgtactatt atctttgaag tcgtaggcat gtggtaaatt cctaccttaa   3300
gatccattaa tcctccaaca cacccttaag acccaaacca taacgcctaa atccaatttc   3360
aacatatttt aggtgacatg ggtatatgtg atattagtta cttaatatag caagctctat   3420
caatgatttt tagtcagaaa atggttgata tgtttttagt ggttgtacta taattgaaga   3480
ggcacataga gcaagttttt agaccatgaa tatatggtgt aaactataga ccatgaatgt   3540
atggtgtaat gctatagtat attaattatt agacttatgg acatatatat tatttatact   3600
taactcacaa acttaataag tcagctcgaa cttataaacc acctgagtcg aactggcctt   3660
atggctcgtt aagctaataa gtcaaaccaa gtcgagctga ttcattatcc aaatctacac   3720
ttatgtaaac aaaacatgat ttcaaattaa gattggtaca aaagtgttct gtttattca   3780 attaaacgct acactatact cccttatgtca acaatagttg atgctacgac aaagcaatga   3840 acatttatg gattagttaa ttttattatc ctaatgacaa ttactattgt cagccaagga   3900
atggagtaag ccaataaaga gtacatatct atgaggaaat ttagatatgc gtgcaacttt   3960 attttttaa tcgagataca gaatgtgcaa ataagggtc catgtaacat acatatattt   4020
cttgttttta tggtaaagga gtgtataaac tataaaggtt gttgcttaga agcgggattt   4080
taataacatc aatttatat taaccttaag cccctatcca atacatgtat tttatttcta   4140
agtacctggt acaagcataa atacacacat ttaagcacac atactcactt gttatgagca   4200
cacacgtaaa ccctactcct actagcacct tcaaaagaca aaacagatag atcttgttga   4260
caaagtctat ttatggtata aactatatac catgaatgta tggtgtaatg ctatagtata   4320
ttgttagact tgtgtacata tatattattt atacttaact cacaaactta ataagtcagc   4380
tcgaacttat aaacgacccg agtcgaactg gccttatggc tcgttaagat aacaagtcaa   4440
accaagccga gctgactcat tatccaaatc tacacttata taaacaaaac atgatttcaa   4500
attaagattg gtacaaaagt gttctatttt attcaattaa accctacact atacacctta   4560
tgtcaacatt agttgatgct acgacaaagc aatgaacatt ttatggatta gttgatgcta   4620
caacaaagta tattgttaga cttgctagat tctatctact gttagcacca aactaaccac   4680
aaaataacaa tccctataac tataggtgga ggtgatgtaa aattaaggga ggggcaattg   4740
tatatggtag taccatagat atcaaacctt ctcaacttag agctatgtct acatagttct   4800
agtcctatga agcatcaacc attttcttat actaaactaa atattttag aggaagggg   4860 tggatcctta ctttcatctc catgagcttc caccccttcc tatgagctta tccatcggtt   4920
gaaagtttct cattgctaga gcttactcgt tattatccca tgccatctga cttttgtata   4980
tgtactatta tctttgaagt cgtaggcatg tgtaaattcc cacctcaaga gtcaagatcc   5040
attaatcctc caacacaccc ttaagaccca accataaca cctaaatcca atttcaacat   5100
attttaggtg acatgggtat atgtgatatt agttacttaa tctagcaagc tctattaatg   5160 attttagtc agaaaatggt taatatgttt ttagtggttg tactataatt gaagaggcac   5220
atagagcaag ttttagtcg ttgtattcta acaatgatt gatgtgtata aatttaataa   5280
attcattgtt gcatcttgtg tttcatacat ttgaaatgct ttgtgcctaa tctatatgga   5340
tgaagaagta aatccttcta aacttttcct tccctgcaat cttttttaaac acactctaaa   5400
```

-continued

| | |
|---|---|
| ccccaaatat ctaatcctaa cctctaaacc tgatttaaat tttctaatct agtccatttg | 5460 |
| tagtgctttt atatttagtc catttgcctt atgtgcctct tgtgtataaa tagcgtagag | 5520 |
| ttctgtataa tagtcaacaa gttttgcctt ttgttgtcgg atccattttc aatccttttg | 5580 |
| tctagttcac ctattgttgt tgtgaaaaaa atgtcacaca ttttttactt cccctatac | 5640 |
| cacatactcc atcacggact aatgatcttc aaggtatgta tgctcagttt aaatccatgt | 5700 |
| ctccacatac tccatcttaa gttcaagtct ctactttaag gtatgtaatt ttaaaacttt | 5760 |
| gacgtattgt aattctataa ggagcaaatc tgaaaattaa ataaggaaaa actggtaaag | 5820 |
| gcatgtttgg aaatcggaac gcagacattt tgttgttcct atgttttct ttaaataaac | 5880 |
| tcattcgtgt aaaatttctt caaaattcct ctccttcgaa cagatccttt tgcccccgga | 5940 |
| cccctttcct acgcttgccc aaacccacaa aaccctcgcc gtcgcgccgc gcgattgcct | 6000 |
| ctccggccgc cgcgagcccg cgacactagt aacggtctac accaccagaa tgactgaaga | 6060 |
| attgaattcc agcaaattca agcttttgtt ttagccaaga tttgagattc gatttgaagt | 6120 |
| gtggaagtcc ttccaatttg ccaatcctat atttgatctc tgctgtgctg cgttaaatcc | 6180 |
| ctaaacttca cagcgcggcg ccggcccagc cacgccggaa gaggtcgccg cgtgaggtca | 6240 |
| gtgtccccgt tgctgccgcc tctaacccga agcctaggcc gctgccggtg cataacaagg | 6300 |
| agaatcaggc ggaggggaaa gtagcagagg aggggcagc aactgaggag ggggagaagt | 6360 |
| accgggcgga accggaaatc ttgccgctgc cgccggccat ggcgaagc | 6408 |

<210> SEQ ID NO 75
<211> LENGTH: 867
<212> TYPE: DNA
<213> ORGANISM: Zea mays

<400> SEQUENCE: 75

| | |
|---|---|
| cgtgaaggca aaatctacgt gtgggaagta cagtccagcc ctcctgtcct cattgctcgg | 60 |
| tacttttcac tgcaagagtt tcagttattc ttgtctccca cttgtatcgt cgcatgcttc | 120 |
| tggatgccaa tgcttcatca ttttcacgct gtataatcac cactgtaaat cgccgataag | 180 |
| acaaactgca gtgtccttcg atggaaggta cctcactcta atccatgctc aatttggtgt | 240 |
| actgtctatt ctaccatttg ctttttttctt ggttctgctt gagaaattct cgattgcatg | 300 |
| tcatatgctg gtgcattttc tttttttctgt ttctgtggtg gattggtaaa atgcgacgat | 360 |
| gccttcctta actagcacaa tccttggagc tggtgaagac ggcaccatct ggcggtggga | 420 |
| tgaagtggac catccgagct ccagaaactg aagaagtgtt gccgctcaat gctggactga | 480 |
| tggttacgct cggttggggt tgcgatggtt gaatccgttg gtggaaagtg ccacctggtg | 540 |
| tttttctag tcaaaatggt tggtgttaac agaatattga atgcttcgaa tgttgaaagt | 600 |
| tgggatgctt gtgctggtac tctgctccgt ggacgagtga acttaggtgc cgtttggttc | 660 |
| acatatttgt aacgtaatgg gtaacagata acgttaaatc atgtttgttt tatttcaacc | 720 |
| gtaatcagat accacattaa aatttgatac cagactattc aaatttgtta acgccagtaa | 780 |
| tcgagcgcaa accattacca tttgcgttac attttttgaa ccaaacagca ccttagtttg | 840 |
| ttgcaacttt gggaaccgtt gtcatct | 867 |

<210> SEQ ID NO 76
<211> LENGTH: 24
<212> TYPE: DNA
<213> ORGANISM: Zea mays

```
-continued

<210> SEQ ID NO 76

<400> SEQUENCE: 76
cgtgaaggca aaatctacgt gtgg                                              24

<210> SEQ ID NO 77
<211> LENGTH: 29
<212> TYPE: DNA
<213> ORGANISM: Zea mays

<400> SEQUENCE: 77
cattacgtta caaatatgtg aaccaaacg                                         29

<210> SEQ ID NO 78
<211> LENGTH: 31
<212> TYPE: DNA
<213> ORGANISM: Zea mays

<400> SEQUENCE: 78
cagaacaaac agatgacaac ggttcccaaa g                                      31

<210> SEQ ID NO 79
<211> LENGTH: 32
<212> TYPE: DNA
<213> ORGANISM: Zea mays

<400> SEQUENCE: 79
agagaagcca acgccawcgc ctcyatttcg tc                                     32

<210> SEQ ID NO 80
<211> LENGTH: 26
<212> TYPE: DNA
<213> ORGANISM: Zea mays

<400> SEQUENCE: 80
cgcgtccatg aagttgaacc cgatag                                            26

<210> SEQ ID NO 81
<211> LENGTH: 27
<212> TYPE: DNA
<213> ORGANISM: Zea mays

<400> SEQUENCE: 81
tgccggtgca taacaaggag aatcagg                                           27

<210> SEQ ID NO 82
<211> LENGTH: 28
<212> TYPE: DNA
<213> ORGANISM: Zea mays

<400> SEQUENCE: 82
cgccgccacc atatagaacc acttatca                                          28
```

PLANT REPRODUCTION POLYNUCLEOTIDES AND METHODS OF USE

This application is a divisional of U.S. Non-provisional Application Ser. No. 09/967,552, filed Sep. 28, 2001, now U.S. Pat. No. 6,887,988, which is a Continuation-in-part of international application PCT/US00/23735 filed 30 Aug. 2000, which claims priority to U.S. Provisional Application No. 60/151,575 filed 31 Aug. 1999, all of which are incorporated by reference.

FIELD OF THE INVENTION

This invention is in the field of plant molecular biology. More specifically, this invention pertains to nucleic acid fragments encoding proteins involved in endosperm and embryo development in plant seeds.

BACKGROUND OF THE INVENTION

Reproduction in flowering plants involves two fertilization events. A sperm fuses with the egg cell to form a zygote which becomes the embryo; a second sperm cell fuses with the doubled-haploid central cell nucleus to form the starting point of the triploid endosperm tissue. While fertilization is thus normally the trigger for seed development, mutants have been identified in which reproductive processes are initiated independent of fertilization. Such mutations uncouple components of seed development from the fertilization process, resulting in developmental patterns resembling those found in apomictic plants.

*Arabidopsis* fie mutants (for fertilization-independent endosperm) isolated by Ohad et al. (Proc. Natl. Acad. Sci. USA 93:5319-5324, 1996; see also U.S. Pat. No. 6,229,064) exhibit replication of the central cell nucleus, initiating endosperm development, in the absence of fertilization. Inheritance of the mutant tie allele by the female gametophyte results in embryo abortion; thus, the trait can be transmitted to progeny only by the male gametophyte. The *Arabidopsis* FIE gene was cloned (Ohad et al., The Plant Cell 11:407-416 (1999); GenBank entry AF129516) and found to encode a polypeptide related to the WD Polycomb group proteins encoded by, for example, Esc in *Drosophila* (Gutjahr et al., EMBO J 14:4296-4306 (1995); Sathe and Harte, Mech. Dev. 52:77-87 (1995); Jones and Gelbart, Mol. Cell. Biol. 13:6357-6366 (1993). WD polycomb proteins may interact with other polynucleotides to form complexes which interfere with gene transcription (Pirrotta, Cell 93:333-336 (1998). Fertilization may trigger alteration of the protein complexes, allowing transcription of genes involved in endosperm development. Thus, loss-of-function fie mutants would lack the ability to form the protein complexes which repress transcription, and endosperm development could proceed independent of fertilization (Ohad et al. 1999, supra).

Chaudhury et al. (Proc. Natl. Acad. Sci. USA 94:4223 (1997)) reported fis (fertilization-independent seed) mutants in *Arabidopsis*. In fis1 and fis2 seed, the endosperm develops to the point of cellularization before atrophying. Proembryos are formed in a low proportion of seeds but do not develop beyond the globular stage. The FIS1 and FIS2 genes were cloned and further characterized. The FIS2 gene comprised structures suggesting function as a transcription factor; the FIS1 gene was found to be allelic (Proc. Natl. Acad. Sci. USA 96:296 (1999)) to the *Arabidopsis* gene MEDEA (Grossniklaus et al. Science 280:446 (1998)).

Apomixis (asexual reproduction) may occur through vegetative reproduction or through agamospermy, the formation of seeds without fertilization. Generally, agamospermy has not been exploited in agriculture; however, it has numerous potential applications, including perpetuation of high yielding crop plant hybrids and varieties, and maintenance of pure inbred lines. Also, seed formation without fertilization avoids factors that can reduce the efficiency of seed set, such as pollen count and pollen viability, and stigma or anther emergence or viability. Agamospermy would also allow the immediate stable incorporation of transgenes without the need for selfing to produce homozygotes. In addition, the fertilization-independent endosperm gene and other related genes could be used to cause the formation of a fertilization-independent endosperm without necessarily forming a viable embryo. Such a seed would not germinate because it lacks an embryo. However, the endosperm, if sufficiently formed, could be used for human and animal food and for commercial milling and extraction. Such embryo-less seeds would have the added advantage of allowing containment of genetically modified organisms to satisfy environmental and regulatory concerns. Such seeds could also be independently modified to produce novel products in the endosperm such as pharmaceuticals, nutraceuticals, and industrial compounds and polymers.

Identification of specific genes involved in agamospermy, such as fertilization-independent endosperm genes, will offer new ways of producing apomictic plants. Such approaches may involve selective mutagenesis of fertilization-independent endosperm genes and then tracking of the mutant alleles in a molecular breeding program, or transgenic methods. Accordingly, identification and isolation of nucleic acid sequences encoding all or a portion of a protein affecting seed development independent of fertilization would facilitate studies of developmental regulation in plants and provide genetic tools to engineer apomixis.

SUMMARY OF THE INVENTION

The present invention concerns an isolated polynucleotide comprising a nucleotide sequence selected from the group consisting of: (a) a first nucleotide sequence encoding a functional fertilization-independent-endosperm (FIE) polypeptide having at least 80% identity, based on the GAP (GCG Version 10) method of alignment, to a polypeptide selected from the group consisting of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68 and 70.

In a second embodiment, it is preferred that the isolated polynucleotide of the claimed invention comprise a nucleic acid sequence selected from the group consisting of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67 and 69 that codes for the polypeptide selected from the group consisting of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68 and 70.

In a third embodiment, this invention concerns an isolated polynucleotide comprising a nucleotide sequence of at least about 30 contiguous nucleotides derived from a nucleotide sequence selected from the group consisting of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 72, and the complement of each such nucleotide sequence.

In a fourth embodiment, this invention relates to a chimeric gene comprising an isolated polynucleotide of the present invention operably linked to at least one suitable regulatory sequence.

In a fifth embodiment, the present invention concerns an isolated host cell comprising a chimeric gene of the present invention or an isolated polynucleotide of the present invention. The host cell may be eukaryotic, such as a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

In a seventh embodiment, the invention concerns a fertilization-independent endosperm polypeptide at least 80% identical, based on the GAP (GCG Version 10) method of alignment, to a polypeptide selected from the group consisting of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68 and 70.

In an eighth embodiment, the invention relates to a method of selecting an isolated polynucleotide that affects the level of expression of a fertilization-independent endosperm polypeptide or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the fertilization-independent endosperm polypeptide or enzyme activity in the host cell containing the isolated polynucleotide; and (d) comparing the level of the fertilization-independent endosperm polypeptide or enzyme activity in the host cell containing the isolated polynucleotide with the level of the fertilization-independent endosperm polypeptide or enzyme activity in a host cell that does not contain the isolated polynucleotide.

In a ninth embodiment, the invention concerns a method of obtaining a nucleic acid fragment encoding a substantial portion of a fertilization-independent endosperm polypeptide, preferably a plant fertilization-independent endosperm polypeptide, comprising the steps of: (a) synthesizing an oligonucleotide primer comprising a nucleotide sequence of at least 30 contiguous nucleotides derived from a nucleotide sequence selected from the group consisting of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 72, and the complement of each such nucleotide sequence; and (b) amplifying a nucleic acid fragment (preferably a cDNA inserted in a cloning vector) using the oligonucleotide primer. The amplified nucleic acid fragment preferably will encode a substantial portion of a fertilization-independent polypeptide.

In a tenth embodiment, this invention relates to a method of obtaining a nucleic acid fragment encoding all or a substantial portion of the amino acid sequence comprising a fertilization-independent endosperm polypeptide, such method comprising the steps of: (a) probing a cDNA or genomic library with an isolated polynucleotide of the present invention; (b) identifying a DNA clone that hybridizes with an isolated polynucleotide of the present invention; (c) isolating the identified DNA clone; and (d) sequencing the cDNA or genomic fragment that comprises the isolated DNA clone.

In an eleventh embodiment, this invention concerns a composition, such as a hybridization mixture, comprising an isolated polynucleotide of the present invention.

In a twelfth embodiment, this invention concerns a method for positive selection of a transformed cell comprising: (a) transforming a host cell with the chimeric gene of the present invention or an expression cassette of the present invention; (b) growing the transformed host cell, preferably a plant cell, such as a monocot or a dicot, under conditions which allow expression of the fertilization-independent endosperm polynucleotide in an amount sufficient to complement a null mutant to provide a positive selection means.

In a thirteenth embodiment, this invention relates to a method of altering the level of expression of an fie protein in a host cell comprising: (a) transforming a host cell with a chimeric gene of the present invention; and (b) growing the transformed host cell under conditions that are suitable for expression of the chimeric gene wherein expression of the chimeric gene results in altered levels of the fie protein in the transformed host cell. The fie protein may act in suppressing transcription of genes involved in endosperm formation.

A fourteenth embodiment relates to an isolated chromosomal polynucleotide of the claimed invention which comprises a first nucleotide sequence selected from the group consisting of SEQ ID NOS: 71 and 72.

A fifteenth embodiment relates to regulatory sequences associated with *Zea mays* fie polynucleotides comprising SEQ ID NOS: 73 and 74.

BRIEF DESCRIPTION OF THE FIGURES

FIG. 1 shows the pattern of direct repeats in the ZmFIE-B 5' upstream region.

BRIEF DESCRIPTION OF THE SEQUENCE LISTING

The invention can be more fully understood from the following detailed description and the accompanying Sequence Listing which form a part of this application.

Table 1 lists the polynucleotides and polypeptides that are described herein, the designation of the cDNA clones and chromosomal sequences that comprise the nucleic acid fragments encoding all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821-1.825. The Sequence Listing contains the one-letter code for nucleotide sequence characters and the three-letter codes for amino acids as defined in conformity with the IUPAC-IUBMB standards described in *Nucleic Acids Res.* 13:3021-3030 (1985) and in *Biochemical J.* 219 (No. 2): 345-373 (1984), which are herein incorporated by reference.

TABLE 1

Reproduction Proteins and Polynucleotides

| Protein | Clone Designation | SEQ ID NO: (Nucleotide) | SEQ ID NO: (Amino Acid) |
|---|---|---|---|
| Fertilization-independent endosperm protein | ccase-b.pk0026.g4 (CGS) | 1 | 2 |
| Fertilization-independent endosperm protein | cen1.mn0001.g10 (CGS) | 3 | 4 |
| Fertilization-independent endosperm protein | cen3n.pk0076.b8 (CGS) | 5 | 6 |
| Fertilization-independent endosperm protein | cpb1c.pk001.d10 (FIS) | 7 | 8 |
| Fertilization-independent endosperm protein | eec1c.pk003.e23 (CGS) | 9 | 10 |
| Fertilization-independent endosperm protein | hlp1c.pk003.e8 (FIS) | 11 | 12 |
| Fertilization-independent endosperm protein | ncs.pk0019.h3 (CGS) | 13 | 14 |
| Fertilization-independent endosperm protein | p0003.cgpfn34f (EST) | 15 | 16 |
| Fertilization-independent endosperm protein | p0003.cgped29rb (CGS) | 17 | 18 |
| Fertilization-independent endosperm protein | p0037.crwao47r (FIS) | 19 | 20 |
| Fertilization-independent endosperm protein | p0041.crtaw93r (FIS) | 21 | 22 |
| Fertilization-independent endosperm protein | p0101.cgamg48r (CGS) | 23 | 24 |
| Fertilization-independent endosperm protein | p0104.cabbn62r (CGS) | 25 | 26 |
| Fertilization-independent endosperm protein | p0107.cbcai79r (CGS) | 27 | 28 |
| Fertilization-independent endosperm protein | p0119.cmtoh49r (CGS) | 29 | 30 |
| Fertilization-independent endosperm protein | p0120.cdebd48r (FIS) | 31 | 32 |
| Fertilization-independent endosperm protein | rca1c.pk0001.d2 (CGS) | 33 | 34 |
| Fertilization-independent endosperm protein | ses2w.pk0015.b10 (CGS) | 35 | 36 |
| Fertilization-independent endosperm protein | wkm1c.pk0003.f4 (CGS) | 37 | 38 |
| Fertilization-independent endosperm protein | ccase-b.pk0026.g4 (EST) | 39 | 40 |
| Fertilization-independent endosperm protein | cen1.mn0001.g10 (EST) | 41 | 42 |
| Fertilization-independent endosperm protein | cpb1c.pk001.d10 (EST) | 43 | 44 |
| Fertilization-independent endosperm protein | eec1c.pk003.e23 (EST) | 45 | 46 |
| Fertilization-independent endosperm protein | hlp1c.pk003.e8 (EST) | 47 | 48 |
| Fertilization-independent endosperm protein | ncs.pk0019.h3 (EST) | 49 | 50 |
| Fertilization-independent endosperm protein | p0003.cgpfn34rb (EST) | 51 | 52 |
| Fertilization-independent endosperm protein | p0003.cgped29rb (EST) | 53 | 54 |
| Fertilization-independent endosperm protein | p0037.crwao47r (EST) | 55 | 56 |
| Fertilization-independent endosperm protein | p0041.crtaw93r (EST) | 57 | 58 |
| Fertilization-independent endosperm protein | p0104.cabbn62r (EST) | 59 | 60 |
| Fertilization-independent endosperm protein | p0107.cbcai79r (CGS) | 61 | 62 |
| Fertilization-independent endosperm protein | p0120.cdebd48r (EST) | 63 | 64 |
| Fertilization-independent endosperm protein | rca1c.pk0001.d2 (EST) | 65 | 66 |
| Fertilization-independent endosperm protein | ses2w.pk0015.b10 (EST) | 67 | 68 |
| Fertilization-independent endosperm protein | wkm1c.pk0003.f4 (EST) | 69 | 70 |
| Fertilization-independent endosperm protein | Genomic Sequence for ZmFIE-B | 71 | |
| Fertilization-independent endosperm protein | Genomic Sequence for ZmFIE-A | 72 | |
| 5' non-coding region | Genomic 5' upstream sequence of ZmFIE-A | 73 | |
| 5' non-coding region | Genomic 5' upstream sequence of ZmFIE-B | 74 | |
| ZmFIE-B partial genomic sequence | From B73 | 75 | |
| Forward primer | For Mo17 and B73 | 76 | |
| Reverse primer | For B73 | 77 | |
| Reverse primer | For Mo17 | 78 | |
| Primer | Mu-specific | 79 | |
| Primer | Gene-specific | 80 | |
| Primer | Gene-specific | 81 | |
| Primer | Gene-specific | 82 | |

DETAILED DESCRIPTION OF THE INVENTION

In the context of this disclosure, a number of terms shall be utilized. The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides derived from SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 72, and the complement of each such sequence.

The term "isolated" polynucleotide refers to a polynucleotide that is substantially free from other nucleic acid sequences, such as and not limited to, other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases may result in substitution of one or more amino acids, but do not affect the functional properties of the polypeptide encoded by the nucleotide sequence. "Substantially similar" also refers to nucleic acid fragments wherein changes in one or more nucleotide bases do not affect the ability of the nucleic acid fragment to mediate alteration of gene expression through, for example, antisense or co-suppression technology, or through acting as a promoter. "Substantially similar" also refers to modifications of the nucleic acid fragments of the instant invention, such as deletion or insertion of one or more nucleotides, that do not substantially affect the functional properties of the resulting transcript (such as in the ability to mediate gene silencing) or do not result in alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments, representing subfragments or modifications of the nucleic acid fragments of the instant invention wherein one or more nucleotides are substituted, deleted and/or inserted, for their ability to affect the level of the polypeptide encoded by the unmodified nucleic acid fragment (the "subject polypeptide") in a plant or plant cell. For example, a substantially similar nucleic acid fragment derived from the instant nucleic acid fragment can be constructed and introduced into a plant or plant cell. The level of the subject polypeptide in a plant or plant cell comprising the substantially similar nucleic fragment can then be compared to the level of the polypeptide in a plant or plant cell that does not comprise the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations at a given site in a nucleic acid fragment which result in the production of a chemically equivalent amino acid, but which do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively-charged residue for another, such as aspartic acid for glutamic acid, or one positively-charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 contiguous nucleotides, derived from a nucleotide sequence selected from the group consisting of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71 and 72, may be used in methods of selecting an isolated polynucleotide that affects the expression of a fertilization-independent endosperm polypeptide in a host cell. A method of selecting an isolated polynucleotide that affects the level of expression of a polypeptide in a virus or in a eukaryotic or prokaryotic host may comprise the steps of: (a) constructing an isolated polynucleotide of the present invention or an isolated chimeric gene of the present invention; (b) introducing the isolated polynucleotide or the isolated chimeric gene into a host cell; (c) measuring the level of a polypeptide or enzyme activity in the host cell containing the isolated polynucleotide; and (d) comparing the level of a polypeptide or enzyme activity in the host cell comprising the isolated polynucleotide with the level of a polypeptide or enzyme activity in a host cell that does not comprise the isolated polynucleotide.

Moreover, substantially similar nucleic acid fragments may also be characterized by their ability to hybridize. Estimates of homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). By "stringent conditions" or "stringent hybridization conditions" is intended conditions under which a probe will hybridize to its target sequence to a detectably greater degree than to other sequences (e.g., at least 2-fold over background). Stringency conditions can be adjusted to screen for moderately similar fragments, such as homologous sequences from distantly related organisms, or to screen for highly similar fragments, such as genes that duplicate functional enzymes from closely-related organisms. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Alternatively, one set of preferred conditions uses a series of washes starting with 6×SSC, 0.5% SDS at room temperature for 15 min, then with 2×SSC, 0.5% SDS at 45° C. for 30 min, and then twice with 0.2×SSC, 0.5% SDS at 50° C. for 30 min. A more-preferred set of stringent conditions uses washes identical to those above except that the temperature of the final two 30-minute washes is increased to 60° C. Another preferred set of highly stringent conditions uses two final washes in 0.1×SSC, 0.1% SDS at 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Substantially similar nucleic acid fragments of the instant invention may also be characterized by the percent identity of their encoded amino acid sequences to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids.

The following terms are used to describe the sequence relationships between a polynucleotide/polypeptide of the present invention and a reference polynucleotide/polypeptide: (a) "reference sequence", (b) "comparison window", (c) "sequence identity", and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acid residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Genetics Computer Group (GCG®) package, Accelrys, Inc., San Diego, Calif.; the CLUSTAL program is well described by Higgins and Sharp, *Gene* 73: 237-244 (1988); Higgins and Sharp, *CABIOS* 5: 151-153 (1989); Corpet, et al., *Nucleic Acids Research* 16: 10881-90 (1988); Huang, et al., *Computer Applications in the Biosciences* 8: 155-65 (1992), and Pearson, et al., *Methods in Molecular Biology* 24: 307-331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995); Altschul et al., *J. Mol. Biol.*, 215:403-410 (1990); and, Altschul et al., *Nucleic Acids Res.* 25:3389-3402 (1997).

Software for performing BLAST analyses is publicly available, e.g., through the National Center for Biotechnology Information (http://www.ncbi.nlm.nih.gov/BLAST). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Clayerie and States, *Comput. Chem.*, 17:191-201 (1993)) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch (*J. Mol. Biol.* 48: 443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

Multiple alignment of the sequences can be performed using the CLUSTAL method of alignment (Higgins and Sharp (1989) *CABIOS.* 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11-17

(1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such are described above. In general, a sequence of ten or more contiguous amino acids, or thirty or more contiguous nucleotides, is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment which directs expression of a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, binding sites for regulatory proteins, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Enhancer elements for plants are known in the art and include, for example, the SV40 enhancer region, the 35S enhancer element, and the like.

Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1-82. Constitutive promoters include, for example, the core promoter of the Rsyn7 (U.S.

Pat. No. 6,072,050); the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

It is further recognized that since in most cases the exact boundaries of regulatory sequences have not been completely defined, nucleic acid fragments of different lengths may have identical promoter activity.

By "tissue-preferred" is intended that the expression driven by a plant promoter is selectively enhanced or suppressed in particular plant cells or tissues, in comparison to other cells or tissues.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, and referred to as "promoter elements" which influence the expression driven by the core promoter. Promoter elements located upstream or 5' to the TATA box are also referred to as upstream promoter elements. In particular embodiments of the invention, the promoter elements of the invention are positioned upstream or 5' to the TATA box. However, the invention also encompasses plant promoter configurations in which the promoter elements are positioned downstream or 3' to the TATA box.

By "transcription regulatory unit" is intended a promoter comprising one or more promoter elements.

By "core promoter" is intended a promoter not comprising promoter elements other than the TATA box and the transcriptional start site.

In reference to a promoter, by "native" is intended a promoter capable of driving expression in a cell of interest, wherein the nucleotide sequence of the promoter is found in that cell in nature.

In reference to a promoter or transcription initiation region, by "synthetic" is intended a promoter capable of driving expression in a cell of interest, wherein the nucleotide sequence of the promoter is not found in nature. A synthetic promoter cannot be isolated from any cell unless it is first introduced to the cell or to an ancestor thereof.

By "suppressors" are intended nucleotide sequences that mediate suppression or decrease in the expression directed by a promoter region. That is, suppressors are the DNA sites through which transcription repressor proteins exert their effects. Suppressors can mediate suppression of expression by overlapping transcription start sites or transcription activator sites, or they can mediate suppression from distinct locations with respect to these sites.

Modifications of the promoter sequences of the present invention can provide for a range of expression. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

The nucleotide sequences for the plant promoters of the present invention comprise the sequences set forth in SEQ ID NOS: 73 and 74 or any sequence having substantial identity to the sequences. By "substantial identity" is intended a sequence exhibiting substantial functional and structural equivalence with the sequence set forth. Any functional or structural differences between substantially identical sequences do not affect the ability of the sequence to function as a promoter as disclosed in the present invention.

Promoters comprising biologically active fragments of SEQ ID NOS: 73 and 74 of the invention are also encompassed by the present invention. By "fragment" is intended a portion of the promoter nucleotide sequence that is shorter than the full-length promoter sequence and which may retain biological activity. Alternatively, fragments of a nucleotide sequence that are useful as hybridization probes or PCR primers generally do not retain biological activity. Thus, fragments of a nucleotide sequence may range from at least about 15, 20, or 25 nucleotides, and up to but not including the full length of a nucleotide sequence of the invention.

The invention encompasses variants of the plant promoters. By "variants" is intended substantially identical sequences. Naturally-occurring variants of the promoter sequences can be identified and/or isolated with the use of well-known molecular biology techniques, as, for example, with PCR and hybridization techniques as outlined below.

Variant promoter nucleotide sequences include synthetically derived nucleotide sequences, such as those generated, for example, by using site-directed mutagenesis or automated oligonucleotide synthesis, but which still exhibit promoter activity. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Generally, a nucleotide sequence of the invention will have at least 80%, preferably 85%, 90%, 95%, up to 98% or more sequence identity to its respective reference promoter nucleotide sequence, and enhance or promote expression of heterologous coding sequences in plants or plant cells.

Biologically active variants of the promoter element sequences should retain promoter regulatory activity, and thus enhance or suppress expression of a nucleotide sequence operably linked to a transcription regulatory unit comprising the promoter element. Promoter activity may be measured by Northern blot analysis. See, for example, Sambrook et al. (1989) *Molecular Cloning: A Laboratory Manual* (2d ed., Cold Spring Harbor Laboratory Press, Plainview, N.Y.); herein incorporated by reference. Protein expression indicative of promoter activity can be measured by determining the activity of a protein encoded by the coding sequence operably linked to the particular promoter; including but not limited to such examples as GUS (b-glucoronidase; Jefferson (1987) *Plant Mol. Biol. Rep.* 5:387), GFP (green florescence protein; Chalfie et al. (1994) *Science* 263:802), luciferase (Riggs et al. (1987) *Nucleic Acids Res.* 15(19):8115 and Luehrsen et al. (1992) *Methods Enzymol.* 216:397-414), and the maize genes encoding for anthocyanin production (Ludwig et al. (1990) *Science* 247:449).

The invention also encompasses nucleotide sequences which hybridize to the promoter element sequences of the invention under stringent conditions, and enhance or suppress expression of a nucleotide sequence operably linked to a transcription regulatory unit comprising the promoter sequences. Hybridization methods are known in the art. See, for example Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York).

An "isolated" or "purified" nucleic acid molecule, or biologically active portion thereof, is substantially free of other cellular material, or culture medium when produced by recombinant techniques, or substantially free of chemical precursors or other chemicals when chemically synthesized.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225-236).

The term "3' non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by the addition of polyadenylic acid tracts to the 3' end of the mRNA precursor. The use of different 3' non-coding sequences is exemplified by Ingelbrecht et al. (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript. An RNA sequence derived from post-transcriptional processing of the primary transcript is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double-stranded form using, for example, the Klenow fragment of DNA polymerase 1. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be, but are not limited to, intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70-73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

As used herein, the term "plant" includes reference to whole plants and their progeny; plant cells; plant parts or organs, such as embryos, pollen, ovules, seeds, flowers, kernels, ears, cobs, leaves, husks, stalks, stems, roots, root tips, anthers, silk and the like. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. A particularly preferred plant is *Zea mays*.

The nucleotide sequences for the promoters of the invention are provided in expression cassettes along with nucleotide sequences of interest for expression in the plant of interest. Such nucleotide constructs or expression cassettes will comprise a transcriptional initiation region in combination with a promoter element operably linked to the nucleotide sequence whose expression is to be controlled by the promoters disclosed herein. Such construct is provided with a plurality of restriction sites for insertion of the nucleotide sequence to be under the transcriptional regulation of the regulatory regions. The expression cassette may additionally contain selectable marker genes.

The transcriptional cassette will include in the 5'-to-3' direction of transcription, a transcriptional and translational initiation region, one or more promoter elements, a nucleotide sequence of interest, and a transcriptional and translational termination region functional in plant cells. The termination region may be native with the transcriptional initiation region comprising one or more of the promoter nucleotide sequences of the present invention, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassette comprising the transcription regulatory unit of the invention operably linked to a nucleotide sequence may also contain at least one additional nucleotide sequence for a gene to be cotransformed into the organism. Alternatively, the additional sequence(s) can be provided on another expression cassette.

Where appropriate, the nucleotide sequence whose expression is to be under the control of the promoter sequence of the present invention, and any additional nucleotide sequence(s), may be optimized for increased expression in the transformed plant. That is, these nucleotide sequences can be synthesized using plant-preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the nucleotide sequence of interest may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126-6130); potyvirus leaders, for example, TEV leader (Tobacco Etch Virus) (Allison et al. (1986)); MDMV leader (Maize Dwarf Mosaic Virus) (*Virology* 154:9-20); human immunoglobulin heavy-chain binding protein (BiP) (Macejak and Sarnow (1991) *Nature* 353:90-94); untranslated leader from the coat protein mRNA of alfalfa mosaic virus (AMV RNA 4) (Jobling and Gehrke (1987) *Nature* 325:622-625); tobacco mosaic virus leader (TMV) (Gallie et al. (1989) *Molecular Biology of RNA*, pages 237-256); and maize chlorotic mottle virus leader (MCMV) (Lommel et al. (1991) *Virology* 81:382-385). See also Della-Cioppa et al., (1987) *Plant Physiology* 84:965-968. Other methods known to enhance translation and/or mRNA stability can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, substitutions, for example, transitions and transversions, may be involved.

The promoters may be used to drive reporter genes or selectable marker genes. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al. (1987) *Mol. Cell. Biol.* 7:725-737; Goff et a. (1990) *EMBO J.* 9:2517-2522; and Kain et al. (1995) *BioTechniques* 19:650-655; and Chiu et al. (1996) *Current Biology* 6:325-330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987-992); methotrexate (Herrera Estrella et al. (1983) *Nature* 303:209-213; Meijer et al. (1991) *Plant Mol. Biol.* 16:807-820); hygromycin (Waldron et al. (1985) *Plant Mol. Biol.* 5:103-108; Zhijian et al. (1995) *Plant Science* 108:219-227); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419423); glyphosate (Shaw et al. (1986) *Science* 233:478-481); phosphinothricin (DeBlock et al. (1987) *EMBO J.* 6:2513-2518).

Other genes that could serve utility in the recovery of transgenic events but might not be required in the final product would include, but are not limited to, such examples as GUS (b-glucoronidase; Jefferson (1987) *Plant Mol. Biol. Rep.* 5:387), GFP (green fluorescence protein; Chalfie et al. (1994) *Science* 263:802), luciferase (Riggs et al. (1987) *Nucleic Acids Res.*15(19):8115 and Luehrsen et al. (1992) *Methods Enzymol.* 216:397-414), and the maize genes encoding for anthocyanin production (Ludwig et al. (1990) *Science* 247:449).

The expression cassette comprising the transcription regulatory unit of the present invention operably linked to a nucleotide sequence of interest can be used to transform any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055), direct gene transfer (Paszkowski et al. (1984) *EMBO J.* 3:2717-2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al., (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In certain preferred embodiments in this regard, the vectors provide for preferred expression. Such preferred expression may be inducible expression, or temporally limited, or restricted to predominantly certain types of cells, or any combination of the above. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids and binaries used for *Agrobacterium*-mediated transformations. All may be used for expression in accordance with this aspect of the present invention.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesil*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, maize, alfalfa, sunflower, *Brassica*, soybean, cotton, safflower, peanut, sorghum, wheat, millet, tobacco, etc.), more preferably maize and soybean plants, yet more preferably maize plants.

Plants of particular interest include grain plants that provide seeds of interest, oil-seed plants, and leguminous plants. Seeds of interest include grain seeds, such as maize, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The promoter sequences and methods disclosed herein, comprising SEQ ID NO: 73 and 74, are useful in regulating expression of a nucleotide sequence of interest in a host plant in a spatial-, temporal-, and/or tissue-preferred manner. Thus, the nucleotide sequence operably linked to the promoters disclosed herein may be a structural gene encoding a protein of interest. Examples of such genes include, but are not limited to, genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms. Other examples include genes encoding proteins which modify plant reproduction, such as those affecting male or female sterility or fertility, or which preferentially express in maternal or paternal tissue.

Alternatively, the nucleotide sequence operably linked to one of the promoters disclosed herein may be an antisense sequence for a targeted gene. Thus, sequences can be constructed which are complementary to, and will hybridize with, the messenger RNA (mRNA) of the targeted gene. Modifications of the antisense sequences may be made, as long as the sequences hybridize to and interfere with expression of the corresponding mRNA. In this manner, antisense constructions having 70%, preferably 80%, more preferably 85% sequence similarity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used. When delivered into a plant cell, expression of the antisense DNA sequence prevents normal expression of the DNA nucleotide sequence for the targeted gene. In this manner, production of the native protein encoded by the targeted gene is inhibited to achieve a desired phenotypic response. Thus the promoter is linked to antisense DNA sequences to reduce or inhibit expression of a native protein in the plant.

The present invention concerns an isolated polynucleotide comprising a nucleotide sequence encoding a functional FIE polypeptide having at least 80% identity, based on the GAP (GCG Version 10) method of alignment, to a polypeptide selected from the group consisting of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68 and 70.

The present invention also concerns an isolated polynucleotide comprising a chromosomal nucleotide sequence having at least 80% identity, based on the GAP (GCG Version 10) method of alignment, to a nucleotide of SEQ ID NO: 71 or 72.

Preferably, the isolated nucleotide sequence comprises a nucleic acid sequence selected from the group consisting of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, and 72 that codes for the polypeptide selected from the group consisting of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68 and 70.

Nucleic acid fragments encoding at least a portion of several proteins involved in seed development have been isolated and identified by comparison of random plant cDNA sequences to public databases containing nucleotide and protein sequences, using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other fertilization-independent endosperm proteins, either as cDNAs or genomic DNAs, could be isolated directly by using all or a portion of the instant nucleic acid fragments as DNA hybridization probes to screen libraries from any desired plant, employing methodology well known to those skilled in the art. Specific oligonucleotide probes based upon the instant nucleic acid sequences can be designed and synthesized by methods known in the art (e.g., Molecular Cloning: A Laboratory Manual, $2^{nd}$ Edition, Sambrook, Fritsch, and Maniatis). Moreover, an entire sequence can be used directly to synthesize DNA probes by methods known to the skilled artisan, such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998-9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *Proc. Natl. Acad. Sci. USA* 86:5673-5677; Loh et al., (1989) *Science* 243:217-220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, and 72 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a fertilization-independent endosperm polypeptide, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOS: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71 and 72, and the complement of such nucleotide sequences; and amplifying a nucleic acid fragment (preferably a cDNA inserted in a cloning vector) using the oligonucleotide primer. The amplified nucleic acid fragment preferably will encode a portion of a fertilization-independent endosperm polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1-34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering endosperm and/or embryo formation in those plants.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53) or nuclear localization signals (Raikhel (1992) *Plant Phys.* 100:1627-1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes is reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or co-suppression (U.S. Pat. Nos. 5,190,931, 5,107,065, and 5,283,323), by formation of double-stranded RNA (International Publication Number WO 99/53050; Smith et al., *Nature* 407:319-320 (2000)), and through other methods known to those of skill in the art.

An antisense, co-suppression, or dsRNA construct would act as a dominant negative regulator of gene activity. While conventional mutations can yield negative regulation of gene activity, these effects are most likely recessive. The dominant negative regulation available with a transgenic approach may be advantageous from a breeding perspective. In addition, the ability to restrict the expression of a specific phenotype to the reproductive tissues of the plant by the use of tissue-specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide that has at least 80% identity, based on the GAP (GCG Version 10) method of alignment, to a polypeptide selected from the group consisting of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68 and 70.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded reproduction proteins. An example of a vector for high level expression of the instant polypeptides in a bacterial host is provided (Example 16).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred kilobases; see Laan et al. (1995) *Genome Res.* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nat. Genet.* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss-of-function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

The Trait Utility System for Corn (TUSC) is a method that employs genetic and molecular techniques to facilitate the study of gene function in maize. Studying gene function implies that the gene's sequence is already known, thus the method works in reverse: from sequence to phenotype. This kind of application is referred to as "reverse genetics", which contrasts with "forward" methods that are designed to identify and isolate the gene(s) responsible for a particular trait (phenotype). One of skill in the art could readily conceive of use of this procedure with the sequences disclosed in the current application.

Pioneer Hi-Bred International, Inc., has a proprietary collection of maize genomic DNA from approximately 42,000 individual $F_1$ plants (Reverse genetics for maize, Meeley, R. and Briggs, S., 1995, Maize Genet. Coop. Newslett. 69:67, 82). The genome of each of these individuals contains multiple copies of the transposable element family, Mutator (Mu). The Mu family is highly mutagenic; in the presence of the active element Mu-DR, these elements transpose throughout the genome, inserting into genic regions, and often disrupting gene function. By collecting genomic DNA from a large number (42,000) of individuals, Pioneer has assembled a library of the mutagenized maize genome.

Mu insertion events are predominantly heterozygous; given the recessive nature of most insertional mutations, the $F_1$ plants appear wild-type. Each of the $F_1$ plants is selfed to produce $F_2$ seed, which is collected. In generating the $F_2$ progeny, insertional mutations segregate in a Mendelian fashion so are useful for investigating a mutant allele's effect on the phenotype. The TUSC system has been successfully used by a variety of laboratories to identify the function of a variety of genes (Cloning and characterization of the maize An1 gene, Bensen, R. J., et al., 1995, Plant Cell 7:75-84; Diversification of C-function activity in maize flower development, Mena, M., et al., 1996, Science 274:1537-1540; Analysis of a chemical plant defense mechanism in grasses, Frey, M., et al., 1997, Science 277:696-699;The control of maize spikelet meristem fate by the APETALA2-like gene Indeterminate spikelet 1, Chuck, G., Meeley, R. B., and Hake, S., 1998, Genes & Development 12:1145-1154; A SecY homologue is required for the elaboration of the chloroplast thylakoid membrane and for normal chloroplast gene expression, Roy, L. M. and Barkan, A., 1998, J. Cell Biol. 141:1-11).

The disclosure of each reference set forth herein is incorporated herein by reference in its entirety.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only and not by way of limitation.

From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Composition of cDNA Libraries; Isolation and Sequencing of cDNA Clones cDNA libraries representing mRNAs from various catalpa, maize, eucalyptus, rice, soybean, sunflower and wheat tissues were prepared. The characteristics of the source tissues are described below in Table 2.

TABLE 2 cDNA Libraries from Catalpa, Maize, Eucalyptus, Rice, Soybean, Sunflower and Wheat

| Library | Tissue | Clone |
|---|---|---|
| ccase-b | Maize callus, somatic embryo formed | ccase-b.pk0026.g4 |
| cen1 | Maize endosperm 10 to 11 days after pollination | cen1.mn0001.g10 |
| cen3n | Maize endosperm 20 days after pollination* | cen3n.pk0076.b8 |
| cpb1c | Maize pooled BMS treated with chemicals related to $Ca^{++}$ channel** | cpb1c.pk001.d10 |
| eec1c | *Eucalyptus tereticornis* capsules (older flowers, lost stamens, possibly fertilized) from adult tree | eec1c.pk003.e23 |
| hlp1c | *Helianthus* sp. leaf infected with phomopsis | hlp1c.pk003.e8 |
| ncs | *Catalpa speciosa* developing seed | ncs.pk0019.h3 |
| p0003 | Maize premeiotic ear shoot, 0.2-4 cm | p0003.cgped29rb p0003.cgpfn34f p0003.cgpfn34rb |

TABLE 2-continued cDNA Libraries from Catalpa, Maize, Eucalyptus, Rice, Soybean, Sunflower and Wheat

| Library | Tissue | Clone |
|---|---|---|
| p0037 | Maize V5 stage*** roots infested with corn root worm | p0037.crwao47r |
| p0041 | Maize root tips smaller than 5 mm in length four days after imbibition | p0041.crtaw93r |
| p0101 | Maize embryo sacs 4 days after pollination* | p0101.cgamg48r |
| p0104 | Maize roots V5, corn root worm infested* | p0104.cabbn62r |
| p0107 | Maize whole kernels 7 days after pollination* | p0107.cbcai79r |
| p0119 | Maize V12 stage*** ear shoot with husk, night harvested* | p0119.cmtoh49r |
| p0120 | Pooled endosperm: 18, 21, 24, 27 and 29 days after pollination* | p0120.cdebd48r |
| rca1lc | Rice nipponbare callus | rca1lc.pk0001.d2 |
| ses2w | Soybean embryogenic suspension 2 weeks after subculture | ses2w.pk0015.b10 |
| wkm1c | Wheat kernel malted 55 hours at 22 degrees Celsius | wkm1c.pk0003.f4 |

*These libraries were normalized essentially as described in U.S. Pat. No. 5,482,845, incorporated herein by reference.
**Chemicals used included caffeine, BHQ, cyclopiazonic acid, nifedipine, verapamil, fluphenizine-N-2-chloroethane, calmidazoilum chloride.
***Maize developmental stages are explained in the publication "How a corn plant develops" from the Iowa State University Coop. Ext. Service Special Report No. 48 reprinted June 1993.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651-1656). The resulting ESTs are analyzed using a Perkin Elmer Model 377 fluorescent sequencer.

Example 2

Identification of cDNA Clones

The cDNA sequences obtained in Example 1 were analyzed for similarity to all publicly available DNA sequences contained in the "nr" database using the BLASTN algorithm (Basic Local Alignment Search Tool; Altschul et al. (1993) J. Mol. Biol. 215:403-410) provided by the National Center for Biotechnology Information (NCBI; see www.ncbi.nlm.nih.gov/BLAST/).

The DNA sequences were also translated in all reading frames and compared for similarity to all publicly available protein sequences contained in the "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases) using the BLASTX algorithm (Gish and States (1993) Nat. Genet. 3:266-272) provided by the NCBI.

For convenience, the P-value (probability) of observing a match of a cDNA sequence to a sequence contained in the searched databases merely by chance as calculated by BLAST is reported herein as a "pLog" value, which represents the negative of the logarithm of the reported P-value. Accordingly, the greater the pLog value, the greater the likelihood that the cDNA sequence and the BLAST "hit" represent homologous proteins.

Abbreviations which may be used in describing the sequences listed in the following tables include:

EST—individual Expressed Sequence Tag

FIS—Full Insert Sequence; the entire cDNA insert comprising the indicated EST

Contig—an assembly of two or more contiguous ESTs

Contig+—a contig comprising an FIS and one or more ESTs

CGS—Complete Gene Sequence; a sequence encoding an entire protein, derived from one or more of the above DNA segments; may be determined in combination with PCR

Example 3

Characterization of cDNA EST Clones Encoding Fertilization-Independent Endosperm Protein The BLASTX search using the EST sequences of clones listed in Table 1 revealed similarity of the polypeptides encoded by the cDNAs to fertilization-independent endosperm protein from Arabidopsis thaliana (NCBI Identifier No. gi 4567095). Scores, on a pLog basis, ranged from 18.0 to 89.7, with an average score of 50.3.

Example 4

Characterization of cDNA FIS and CGS Clones Encoding Fertilization-Independent Endosperm Protein The sequence of the entire cDNA insert (FIS) in each of the clones listed in Table 3 was determined. Further sequencing and searching of the DuPont proprietary database allowed the identification of other maize, rice, soybean, wheat, eucalyptus, sunflower, and catalpa clones encoding fertilization-independent endosperm proteins. A BLASTX search using the full insert sequences and complete gene sequences listed in Table 1 revealed similarity of the polypeptides encoded by these cDNAs to fertilization-independent endosperm protein from Arabidopsis thaliana (NCBI Identifier No. gi 4567095). Scores, on a pLog basis, averaged 57.4 for Full Insert Sequences and 150.5 for Complete Gene Sequences.

Example 5

The amino acid sequences set forth in SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68 and 70 were compared to the *Arabidopsis thaliana* sequence gi4567095 using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP=LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicated that the nucleic acid fragments comprising the instant cDNA clones encoded a substantial portion of a fertilization-independent endosperm protein. These sequences represent the first catalpa, eucalyptus, maize, rice, soybean, sunflower and wheat sequences encoding fertilization-independent endosperm proteins known to Applicant.

Example 6

Mapping and Isolation of Genomic Sequences of FIE-A and FIE-B

ZmFIE-A (also referred to as ZmFIE1) maps to Chromosome 4 (bin 4.04) and ZmFIE-B (also referred to as ZmFIE2) maps to Chromosome 10 (bin 10.03). Map positions were identified by a standard procedure using RFLP analysis of a mapping population (Davis et al., Genetics (1999) 152:1137-1172).

To obtain genomic copies of Zm FIE genes, BAC (Bacterial Artificial Chromosome) libraries were used. BAC libraries were constructed according to the Texas A&M BAC Center protocol. High-molecular-weight DNA isolated from line Mo17, embedded in LMP agarose microbeads, was partially digested by HindIII. The DNA was then size-selected by pulsed-field gel electrophoresis to remove the smaller DNA fragments that can compete more effectively than the larger DNA fragments for vector ends. The size-selected DNA fragments were ligated into pBelo-BAC11 at the HindIII site. BAC libraries were screened by hybridization with $^{32}$P-labeled probes (Maniatis). SEQ ID NO: 1 and SEQ ID NO: 29 correspond to ZmFIE-B and ZmFIE-A ESTs. BAC DNAs were isolated, subcloned into BluescriptII (SK+) vector (Stratagene), and sequenced.

The genomic sequences of the maize and *arabidopsis* FIE genes show a high degree of conservation of intron/exon structure. There are 13 exons with almost identical lengths (with the accuracy of BestFit program, GCG) in the maize and *Arabidopsis* genes, with exceptions of 5' and 3' UTRs. This high degree of conservation between FIE genes in monocots and dicots suggests that gene function is under strong evolutionary pressure. The genomic structure of the ZmFIE-A gene is different from the ZmFIE-B and *arabidopsis* genes by 1 intron of 385 nt length, which is positioned within the 5'UTR, 6 nt upstream of the ATG codon. Introns located in the 5' UTR are important for tissue-specific expression of the genes (McElroy et al.,(1991) Molecular & General Genetics 231:150-160). As is shown in Example 7, ZmFIE-A expression occurs mostly in developing endosperm; this regulation may be achieved through splicing of the 5'UTR intron.

TABLE 3

The exon lengths (in bp) of the maize and arabidopsis FIE genes

| | 1<br>5' UTR | 2 | 3 | 4 | 5 | 6 | 7 | 8 | 9 | 10 | 11 | 12 | 13<br>3' UTR |
|---|---|---|---|---|---|---|---|---|---|---|---|---|---|
| ZmFIE-A | 340 | 66 | 125 | 83 | 96 | 75 | 84 | 71 | 62 | 98 | 65 | 59 | 347 |
| ZmFIE-B | 509 | 66 | 125 | 83 | 96 | 75 | 84 | 71 | 62 | 98 | 65 | 59 | 230 |
| AtFIE | 375 | 66 | 122 | 83 | 96 | 75 | 84 | 71 | 62 | 106 | 57 | 59 | 317 |

Example 7

Analysis of Expression of FIE-A and FIE-B by RT-PCR

To determine ZmFIE expression patterns, RNA was extracted from different tissues and RT-PCR was performed using ZmFIE-A- and ZmFIE-B-specific primers.

With the exception of pollen, ZmFIE-B is expressed in all tissues examined, including leaf, immature leaf, tassel, stem, silk, 3-day root tissue, ovules before pollination, and in whole-kernel, endosperm, and embryo tissues at 11 days after pollination (DAP). Pollen is the only tissue where ZmFIE-B gene expression is very low. It is very likely that ZmFIE-B expression is repressed in the sperm nuclei, but that the gene is still active in the vegetative nucleus of the pollen.

Conversely, ZmFIE-A is expressed only in kernels after pollination. None of the vegetative tissues has a detectable level of the ZmFIE-A transcripts. ZmFIE-A also is not expressed in mature pollen.

In a time-course comparison of ZmFIE-A and ZmFIE-B expression, whole kernels were collected at intervals after pollination and RT-PCR was performed. ZmFIE-A mRNA was first detected at about 9 days after pollination (DAP), peaked at about 11 DAP, and was markedly reduced after about 20 DAP. ZmFIE-B was expressed at a consistent level during the time tested, from 3 DAP to 25 DAP. These results were confirmed by Northern hybridization of the poly-A RNA extracted from the same set of tissues.

Example 8

Analysis of Expression of FIE-A and FIE-B by Lynx MPSS™

To further refine analysis of expression of FIE-A and FIE-B, Lynx MPSS™ (massively parallel signature sequencing) experiments were used for BLAST searching of the 17-mer tags expressed in various tissues. (For a description of Lynx technology, see Nature Biotechnology (2000) 18:630-634.) In complete agreement with RT-PCR and Northern results (Example 7), 17-mer tags of ZmFIE-A transcripts were not detected in ovules before pollination, but were detected in the endosperm of developing kernels after pollination, rapidly reaching a peak at about 8 to 9 days after pollination (DAP), then diminishing to reach the basal level at about 30 DAP. A very low level of ZmFIE-A tags was found in the embryo. These results provide strong evidence that the ZmFIE-A gene is expressed specifically in endosperm after fertilization. Expression of the ZmFIE-B gene cannot be detected by Lynx technology because the ZmFIE-B gene is lacking the GATC restriction site used in creating 17-mer tags.

Example 9

In situ Localization of FIE mRNA in Ovules and Developing Kernels

To further determine expression patterns of ZmFIE genes in maize, in situ hybridization was performed using the protocol of Jackson, D. P. (1991) (In situ Hybridization in Plants, *Molecular Plant Pathology: A Practical Approach*, D. J. Bowles, S. J. Gurr, and M. McPherson, eds.; Oxford University Press, England, pp. 63-74). Sense and antisense mRNA probes of about 0.9 kb corresponding to FIE genes were labeled non-isotopically with digoxigenin and incubated with fixed sections of maize tissues from ovules at silking and from kernels at 5, 8 and 12 days after pollination (DAP). FIE-A hybridization was performed only with ovules and kernels at 5 DAP. Following extensive washing to remove unbound probe, sections were incubated with anti-digoxigenin alkaline phosphatase to detect areas of probe hybridization. FIE mRNA was detected specifically with the antisense probe; the sense probe did not hybridize, therefore serving as a negative control.

FIE antisense probes gave a signal in the embryo sac of the mature ovules at silking. The signal within the embryo sac before fertilization is likely due to ZmFIE-B mRNA, because RT-PCR and Lynx data do not show a detectable level of ZmFIE-A gene expression in ovules before fertilization. In kernels at 2 to 5 DAP, the most intense signal appeared in the embryo-surrounding region and on the periphery of the developing endosperm. At the later stages (8, 10, or 15 DAP), the signal persists at the embryo, but is not detectable in the endosperm using FIE-B probe. An in situ experiment with ZmFIE-A was not performed at these stages.

FIE proteins belong to the Polycomb group (PcG) proteins, which are involved in multiple aspects of embryogenesis in *Drosophila* and mammals. PcG proteins appear to have a conserved role in the zygotic control of the development of the anterior-posterior axis. The *arabidopsis* FIE protein plays a pleiotropic role as a repressor of endosperm development before pollination, a regulator of the establishment of the anterior-posterior axis in the endosperm, and a factor of the embryo development.

The differential pattern of expression of the ZmFIE genes argues that functions of the maize FIE genes are separated in evolution. The ZmFIE-B gene may play a role as a repressor of seed development before pollination in the embryo sac, and as a regulator of the anterior-posterior axis in the developing embryo. The ZmFIE-A gene, induced after pollination and expressed only in the endosperm, may play a role as a regulator of the establishment of the anterior-posterior axis in the endosperm.

One could expect that inactivation of ZmFIE-B function would result in seed development without fertilization (apomixis), but that inactivation of the ZmFIE-A gene would interfere with endosperm development.

Example 10

Isolation and Identification of the Promoter Regions of FIE-A and FIE-B 5.5 kb of the FIE-A upstream region and 6.0 kb of the ZmFIE-B upstream region were sequenced from the BAC genomic clones (Example 6).

ZmFIE-A 5' Upstream Region (SEQ ID NO: 73)

The 5' upstream region of the ZmFIE-A gene shares sequence homology with the 5' LTR (long terminal repeat) of the retrotransposon RIRE-1 (GenBank accession # D85597), at positions 2984-3378. Retrotransposable elements are landmarks of the intragenic regions in the maize genome (SanMiguel et al. (1996) Science 274:765-768). Sequence homology to retrotransposons indicates the border of the gene-specific region. According to this definition, the sequence downstream of 3378 nt (nucleotide/s) may be considered as a part of the ZmFIE-A gene. The RNA startpoint is at 4159, as shown by an alignment with the longest EST, cgamg48. Taking these reference points, the basal promoter is located between 3378-4159 nt and is 781 nt long. No repeats or secondary structures are found in the ZmFIE-A basal promoter. There is an intron 386 nt long at position 4319-4705. The intron sequence is present in genomic DNA, but is absent in the cDNA (cgamg48). The intron is positioned just 6 nt upstream from the translation start codon ATG at 4712 nt. This intron may play a regulatory role in ZmFIE-A gene expression, for example, providing the properly spliced RNA only in kernels after fertilization.

ZmFIE-B 5' Upstream Region (SEQ ID NO: 74)

The size of the ZmFIE-B promoter is estimated to be about 6 kb from the translation start codon ATG to the point of homology with the retrotransposon Milt1 that might be considered as a landmark of the intragenic region. This 6 kb region is a unique sequence with no known homology in the published databases and shows a pattern of repetitive sequences.

The sequence from 2919 to 5237 nt (nucleotides) consists of two types of repeats, named A and B, and a spacer (see FIG. 1). Repeats are organized in the following order: $A_1$-$B_1$ spacer $B_2$-$A_2$. Repeats $A_1$ and $A_2$ are 583 nt long and share 95% homology. Repeats $B_1$ and $B_2$ are 348 nt long and share 93% homology. The spacer size is 410 nt. Repeats and a spacer form the 2.3 kb region. The $B_1$ spacer sequence, C, is repeated again from 321 to 1070 nt of the 5' upstream region of ZmFIE-B.

A pattern of perfect direct repeats argues for their functional significance. Expression of ZmFIE-B is constitutive and not tissue-specific. The only specific feature of this gene is the repression of the paternal allele during early kernel development (Example 11; also see Lai J. and Messing J., 2001, 43$^{rd}$ Maize Genetics Conference, Abstract P39, page 57). This phenomenon is termed parental imprinting and has been shown for the *Arabidopsis* FIE gene (Ohad et al., PNAS 93:5319-5324 (1996); Luo et al., PNAS 97:10637-10642 (2000)). In mammals, the imprinting control region (ICR) has been identified as a 2 kb region located from −2 to −4 kb relative to the transcription start of the imprinted genes (Thorvaldsen et al. (1998) Genes and Development 12:3693-3702). The ICR (or the DMD, the differentially methylated domain) regulates imprinting by DNA methylation.

The repetitive structure found upstream of the ZmFIE-B gene may be responsible for imprinting of the ZmFIE-B gene and is being termed the ICE (Imprinting Control Element, to distinguish from the animal ICR). To determine whether the ICE is required for imprinted expression of ZmFIE-B gene, expression cassettes can be constructed directing expression of the reporter genes with and without fusion with the ICE. If the ICE is required for imprinting, the parent-of-origin expression of the reporter constructs will be observed.

One of skill in the art would recognize that the ICE may provide a tool for the modification of gene expression in developing kernels and could be used as a tool in modifying or controlling imprinting. The ICE may be a target for DNA methylation like the DMD (ICR) in mammals, or the ICE may be a binding site for specific proteins. Protein-mediated mechanism of the imprinting seems more likely, because frequency of the DNA methylation sites CpG and CpNpG is reduced to about 0.5-1% in the ICE and overall 5' upstream region of the ZmFIE-B gene; equal distribution of di- and tri-nucleotides along DNA sequences predicts a frequency of 6%. The ICE may be used as a binding target for proteins regulating gene expression by imprinting.

Example 11

Monitoring of Parent-of-Origin Expression by Allele-Specific Primers

As described in Example 10, ZmFIE-B expression varies with the parent of origin. Only the maternal allele is expressed immediately following pollination; expression of the paternal allele resumes after 10 DAP. This phenomenon, termed imprinting, is mediated by direct repeats (the ICE, Imprinting Control Element) positioned upstream of the ZmFIE-B coding region (Example 10).

Inbreds B73 and Mo17 comprise polymorphisms which aid in monitoring parent-of-origin expression. The differences lie in the genomic fragments in the vicinity of the stop codon of the ZmFIE-B gene.

The B73 genomic sequence (SEQ ID NO: 75) contains a 185-nt insertion with 13-nt terminal inverted repeats. The insertion is flanked by 5-nt direct repeats, which result from a target duplication, providing strong evidence for the transposition origin of the insertion. The insertion is a typical example of so-called MITE elements, which are very abundant components of the maize genome (Wessler, S. R. Plant Physiol. (2001) 125(1):149-151). In the B73 background, ZmFIE-B polyA transcripts are terminated in the middle of the MITE element.

In the Mo17 background, ZmFIE-B polyA transcripts are terminated within genomic sequence with no homology to the MITE element.

Thus, the MITE element was used to design primers specific for B73 or Mo17 ZmFIE-B transcripts. The forward primer, CGTGMGGCAAAATCTACGTGTGG (SEQ ID NO: 76), is common to both genotypes. The reverse primers are genotype specific. A reverse primer CATTACGTTA-CAAATATGTGMCCAAACG (SEQ ID NO: 77) amplifies transcripts only from the B73 gene in an RT-PCR reaction. A reverse primer CAGMCAAACAGATGACMCGGTTC-CCAAAG (SEQ ID NO: 78) amplifies transcripts only from the Mo17 gene in an RT-PCR reaction. This primer combination allows monitoring of the paternal and maternal ZmFIE-B allele expression. RT-PCR reactions were conducted at various DAP time intervals in B73/Mo17 reciprocal crosses. The maternal ZmFIE-B allele (either B73 or Mo17) is expressed immediately following pollination and continuing through the full 16 days tested. Whereas the paternal ZmFIE-B allele (either Mo17 or B73) is expressed beginning at approximately 10 days after pollination and continuing through the full 16 days tested.

Example 12

Construction of FIE-Null Genetic Backgrounds and Inactivation of ZmFIE Genes by the Mutator Transposon Insertions (TUSC)

Gene inactivation can be used to determine the function of ZmFIE genes in the regulation of endosperm development. When fertilization is prevented in *Arabidopsis* plants heterozygous for fie mutant alleles, siliques nevertheless elongate and contain seed-like structures due to partial endosperm development. No embryo development is observed (Ohad, Yadegari et al.,(1999) Plant Cell 11:407-415). Maize fie mutants would be expected to develop endosperm (or kernels) in the absence of fertilization (i.e. when immature ears are protected from pollination by bags).

The Pioneer proprietary system TUSC (Trait Utility System for Corn) was used to screen for FIE genes disrupted by Mutator transposable element insertion. $F_2$ families segregating for the Mutator insertions were screened by PCR with the Mu-specific primer (SEQ ID NO: 79) and FIE-A or FIE-B gene-specific primers (SEQ ID NOS: 80-82). No positive signals were found for the Mutator insertions in the ZmFIE-A gene. However, six Mu insertions were identified in the ZmFIE-B gene. The Mu insertion sites were sequenced. Data are shown in the following table:

TABLE 4

| | | Mu insertion sites | |
|---|---|---|---|
| Allele # | Allele name | Individual plants in TUSC pools | Site of Mu insertion |
| 1 | fieb::Mu61E09 | PV03 61 E-09 | 234 nt upstream of ATG |
| 2 | fieb::Mu25C04 | BT94 25 C-04 | 188 bp upstream of ATG |
| 3 | fieb::Mu57B12 | PV03 57 B12 | 183 bp upstream of ATG |
| 4 | fieb::Mu217 | I6A89718 B217 | 138 bp upstream of ATG |
| 5 | fieb::Mu203 | I6A80321 B203 | 138 bp upstream of ATG |
| 6 | fieb::Mu29A08 | BT94 29 A08 | 4 bp of $1^{st}$ exon/intron junction |

All Mu insertions occurred in non-coding regions of ZmFIE-B. Alleles #1-5 represent the Mu insertions in the 5' UTR at distances of 138 to 234 bp upstream of the translation start codon ATG. Allele #6 carries the Mu insertion in the first intron, 4 nucleotides past the exon/intron junction.

Homozygous plants were obtained for alleles #1-5. Transcription of ZmFIE-B is not affected in the Mu homozygous plants as has been shown by RT-PCR. Those plants do not demonstrate the expected phenotype of developing endosperm (or kernels) in the absence of fertilization. One of the possible explanations for the normal function of ZmFIE-B with the Mu upstream insertions is the outward reading promoter in the end of Mu (Barkan and Martienssen (1991) Proc. Natl. Acad. Sci. USA 88:3502-3506). This promoter may support transcription of the fieb::Mu alleles. No changes in phenotype were seen as a result of these Mu insertions.

To isolate derivative alleles at the ZmFIE-B locus that no longer require Mutator activity and are stable null alleles, the site-selected transposon mutagenesis (SSTM) method was used (Plant Cell 7:287-294, 1995). The Mu element generates the flanking deletions resulting in null alleles at frequencies approaching 1% (Taylor and Walbot (1985) EMBO J. 4:869-876). To generate flanking deletions at the ZmFIE-B locus, plants homozygous for fieb::Mu alleles were crossed with the Mu active line les22 (wherein white necrotic lesions are a marker for the presence of the active Mutator; Hu, Yalpani, et al. (1998) Plant Cell 10:1095-1105). The progeny of this cross, Mu-active fieb::Mu/+, were crossed to Mo17 inbred to produce seed with the potential Mu-flanking deletions. Screening of the flanking deletions was performed by PCR with the Mu- and fieb-specific primers (see above). DNA was isolated from seedling leaf punches using Puregene kit (Gentra System, Minneapolis, Minn.) according to the manufacturer's protocol. Initially, four deletions, 100-200 nt long, were identified from the fieb::Mu allele #2.

SSTM represents an efficient way to generate stable null alleles from the original TUSC material in those cases when Mu insertions occur in "non-coding" neutral regions of the genes. These derivative deletions provide the genetic material for phenotypic and cytological analysis to determine the role of the FIE gene in controlling endosperm development in maize.

Example 13

Use of ZmFIE Mutants with Maize CHD to Induce Apomixis

A "CHD polypeptide" refers to a polypeptide containing 3 domains: a chromatin organization modifier, a helicase SNF-2 related/ATP domain, and a DNA binding domain. Down-regulation of CHD in transformed maize is expected to result in a more embryogenic callus phenotype. (See pending U.S. patent application Ser. No. 60/251,555, filed Dec. 6, 2000.)

Maize expression cassettes down-regulating CHD expression (CHD-DR) in the inner integument or nucellus can easily be constructed. An expression cassette directing expression of the CHD-DR polynucleotide to the nucellus is made using the barley Nuc1 promoter (See pending U.S. patent application Ser. No. 09/703,754, filed Nov. 1, 2000). Embryos are co-bombarded with the selectable marker PAT fused to the GFP gene (UBI::moPAT~moGFP) along with the nucellus specific CHD-DR expression cassette described above. Both inbred (P38) and GS3 transformants are obtained and regenerated as described in Example 14.

When such nuc1:CHD-DR transformation is accomplished in a mutant fie background, both de novo embryo development and endosperm development without fertilization could occur. (see Ohad et al. 1999 The Plant Cell 11:407-415). Upon microscopic examination of the developing embryos it will be apparent that apomixis has occurred by the presence of embryos budding off the nucellus.

Example 14

Expression of Chimeric Genes in Monocot Cells

A chimeric gene is constructed which comprises a cDNA encoding the instant polypeptides in sense orientation with respect to the maize 27 kD zein promoter located 5' to the cDNA fragment, and the 10 kD zein 3' end located 3' to the cDNA fragment. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML1 03 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue®; Stratagene). Bacterial transformants can be screened by restriction enzyme digestion of plasmid DNA and limited nucleotide sequence analysis using the dideoxy chain termination method (Sequenase® DNA Sequencing Kit; U.S. Biochemical). The resulting plasmid construct comprises a chimeric gene encoding, in the 5' to 3' direction, the maize 27 kD zein promoter, a cDNA fragment encoding the instant polypeptides, and the 10 kD zein 3' region.

The chimeric gene described above can then be introduced into maize cells by the following procedure. Immature maize embryos can be dissected from developing caryopses derived from crosses of the inbred maize lines H99 and LH132. The embryos are isolated 10 to 11 days after pollination when they are 1.0 to 1.5 mm long. The embryos are then placed in contact with agarose-solidified N6 medium (Chu et al. (1975) *Sci. Sin. Peking* 18:659-668), axis-side down. The embryos are kept in the dark at 27° C. Friable embryogenic callus, consisting of undifferentiated masses of cells with somatic proembryoids and embryoids borne on suspensor structures, proliferates from the scutellum of these immature embryos. The embryogenic callus isolated from the primary explant can be cultured on N6 medium and sub-cultured on this medium every 2 to 3 weeks.

The plasmid p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique: Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton® flying disc (Bio-Rad Labs). The particles are then accelerated into the maize tissue with a Biolistic® PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn covering a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment, the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833-839).

Example 15

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic® PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al.,(1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension are added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 16

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125-135; see also www.novagen.com) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase® (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

---

What is claimed is:

1. An isolated promoter which drives transcription in a seed-preferred manner, wherein the promoter comprises the nucleotide sequence set forth as SEQ ID NO: 73.

2. An expression cassette comprising a promoter of claim 1 and a second nucleotide sequence operably linked to the promoter.

3. A transformation vector comprising the expression cassette of claim 2.

4. A plant stably transformed with the expression cassette of claim 2.

5. The plant of claim 4, wherein the plant is a monocot.

6. The plant of claim 5, wherein the monocot is maize, wheat, rice, barley, sorghum, or rye.

7. Seed of the plant of claim 4 comprising within their genome said expression cassette.

8. A method for selectively expressing a nucleotide sequence in a plant cell, the method comprising transforming a plant cell with the transformation vector of claim 3.

9. The method of claim 8 further comprising regenerating a stably transformed plant from the transformed plant cell, wherein expression of the second nucleotide sequence alters the phenotype of the plant seed.

10. The method of claim 8, wherein the second nucleotide sequence encodes a gene involved in fatty acid synthesis.

11. The method of claim 8, wherein the second nucleotide sequence encodes a gene providing enhanced amino acid content.

12. A plant cell stably transformed with the expression cassette of claim 2.

13. The plant cell of claim 12, wherein the plant cell is from a monocotyledonous plant.

14. The plant cell of claim 13, wherein the plant is maize, wheat, rice, barley, sorghum, or rye.

* * * * *